US012570745B2

(12) United States Patent
Chen et al.

(10) Patent No.: US 12,570,745 B2
(45) Date of Patent: \*Mar. 10, 2026

(54) BIOMARKERS AND METHODS OF TREATING PD-1 AND PD-L1 RELATED CONDITIONS

(71) Applicant: Genentech, Inc., South San Francisco, CA (US)

(72) Inventors: Daniel Shin-Yu Chen, Burlingame, CA (US); Priti Hegde, San Mateo, CA (US); Hartmut Koeppen, San Mateo, CA (US); Marcin Kowanetz, San Francisco, CA (US)

(73) Assignee: Genentech, Inc., South San Francisco, CA (US)

( \* ) Notice: Subject to any disclaimer, the term of this patent is extended or adjusted under 35 U.S.C. 154(b) by 735 days.

This patent is subject to a terminal disclaimer.

(21) Appl. No.: 17/686,628

(22) Filed: Mar. 4, 2022

(65) Prior Publication Data

US 2022/0363764 A1 Nov. 17, 2022

Related U.S. Application Data

(63) Continuation of application No. 14/850,462, filed on Sep. 10, 2015, now Pat. No. 11,299,544, which is a continuation of application No. PCT/US2014/024746, filed on Mar. 12, 2014.

(60) Provisional application No. 61/883,186, filed on Sep. 26, 2013, provisional application No. 61/829,236, filed on May 30, 2013, provisional application No. 61/812,678, filed on Apr. 16, 2013, provisional application No. 61/802,296, filed on Mar. 15, 2013.

(51) Int. Cl.
| | |
|---|---|
| *A61K 39/00* | (2006.01) |
| *C07K 16/28* | (2006.01) |
| *C12Q 1/6886* | (2018.01) |
| *G01N 33/574* | (2006.01) |
| *G01N 33/68* | (2006.01) |
| *G06Q 30/0251* | (2023.01) |

(52) U.S. Cl.
CPC ........ *C07K 16/2827* (2013.01); *C12Q 1/6886* (2013.01); *G01N 33/57484* (2013.01); *G01N 33/57492* (2013.01); *G01N 33/6854* (2013.01); *G01N 33/6869* (2013.01); *G06Q 30/0251* (2013.01); *A61K 2039/505* (2013.01); *C07K 2317/24* (2013.01); *C07K 2317/76* (2013.01); *G01N 2333/5412* (2013.01); *G01N 2333/70532* (2013.01); *G01N 2800/52* (2013.01)

(58) Field of Classification Search
CPC ......... C07K 16/2827; G01N 33/57484; G01N 33/57492; G01N 33/6854; A61K 39/00
See application file for complete search history.

(56) References Cited

U.S. PATENT DOCUMENTS

| | | | |
|---|---|---|---|
| 5,922,855 | A | 7/1999 | Liskay et al. |
| 6,803,192 | B1 | 10/2004 | Chen |
| 7,635,757 | B2 | 12/2009 | Freeman et al. |
| 7,754,208 | B2 | 7/2010 | Ledbetter et al. |
| 7,892,540 | B2 | 2/2011 | Chen et al. |
| 7,895,540 | B2 | 2/2011 | Engin et al. |
| 8,217,149 | B2 | 7/2012 | Irving et al. |
| 8,552,154 | B2 | 10/2013 | Freeman et al. |
| 8,981,063 | B2 | 3/2015 | Chen |
| 10,689,445 | B2 | 6/2020 | Kowanetz et al. |
| 2002/0028487 | A1 | 3/2002 | La Thangue et al. |
| 2006/0083744 | A1 | 4/2006 | Chen et al. |
| 2008/0299555 | A1 | 12/2008 | Nitta et al. |
| 2009/0055944 | A1 | 2/2009 | Korman et al. |
| 2009/0215084 | A1 | 8/2009 | Kwon et al. |
| 2009/0317368 | A1 | 12/2009 | Chen |
| 2010/0015642 | A1 | 1/2010 | Kwon et al. |
| 2010/0203056 | A1 | 8/2010 | Irving et al. |
| 2011/0200620 | A1 | 8/2011 | Chen et al. |
| 2011/0318839 | A1 | 12/2011 | Shiku et al. |
| 2012/0010230 | A1 | 1/2012 | MacDougall et al. |
| 2012/0039906 | A1 | 2/2012 | Olive |
| 2013/0034559 | A1 | 2/2013 | Queva et al. |
| 2013/0195854 | A1 | 8/2013 | Gerdes et al. |
| 2013/0260379 | A1 | 10/2013 | Alexander et al. |
| 2013/0309250 | A1 | 11/2013 | Cogswell et al. |
| 2014/0341917 | A1 | 11/2014 | Nastri et al. |

(Continued)

FOREIGN PATENT DOCUMENTS

| | | |
|---|---|---|
| AU | 2012211347 A1 | 8/2012 |
| CN | 101084438 A | 12/2007 |

(Continued)

OTHER PUBLICATIONS

Spigel et al., "Clinical activity, safety, and biomarkers of MPDL3280A, an engineered PD-L1 antibody in patients with locally advanced or metastatic non-small cell lung cancer (NSCLC)," Journal of Clinical Oncology. 31(15_suppl):8008 (May 2013) (2 pages).

(Continued)

*Primary Examiner* — Lei Yao
(74) *Attorney, Agent, or Firm* — Clark & Elbing LLP; Thomas J. Takara

(57) ABSTRACT

Provided herein are biomarkers for the treatment of pathological conditions, such as cancer, and method of using PD-1/PD-L1 pathway antagonists. In particular, provided are biomarkers for patient selection and prognosis in cancer, as well as methods of therapeutic treatment, articles of manufacture and methods for making them, diagnostic kits, methods of detection and methods of advertising related thereto.

15 Claims, 31 Drawing Sheets
(22 of 31 Drawing Sheet(s) Filed in Color)
Specification includes a Sequence Listing.

(56) References Cited

U.S. PATENT DOCUMENTS

| | | |
|---|---|---|
| 2014/0356353 A1 | 12/2014 | Queva et al. |
| 2014/0357509 A1 | 12/2014 | Ma et al. |
| 2015/0045251 A1 | 2/2015 | Wang et al. |
| 2015/0071910 A1 | 3/2015 | Kowanetz et al. |
| 2015/0148585 A1 | 5/2015 | Das et al. |
| 2015/0309035 A1 | 10/2015 | Tacha |
| 2015/0346208 A1 | 12/2015 | Couto et al. |
| 2015/0346210 A1 | 12/2015 | Nitta et al. |
| 2016/0009805 A1 | 1/2016 | Kowanetz et al. |
| 2016/0272712 A1 | 9/2016 | Freeman et al. |
| 2016/0333085 A1 | 11/2016 | Tacha et al. |
| 2016/0333414 A1 | 11/2016 | Belousov et al. |
| 2016/0370370 A1 | 12/2016 | Qi et al. |
| 2017/0023579 A1 | 1/2017 | Nitta et al. |
| 2017/0052188 A1 | 2/2017 | Kowanetz et al. |
| 2017/0082627 A1 | 3/2017 | Dennis et al. |
| 2017/0101672 A1 | 4/2017 | Luo et al. |
| 2017/0212122 A1 | 7/2017 | Alexander et al. |
| 2018/0022809 A1 | 1/2018 | Kowanetz et al. |
| 2018/0031567 A1 | 2/2018 | Dennis et al. |
| 2018/0274038 A1 | 9/2018 | Belousov et al. |
| 2018/0372747 A1 | 12/2018 | Birch |

FOREIGN PATENT DOCUMENTS

| | | | |
|---|---|---|---|
| CN | 101104640 A | 1/2008 |
| CN | 101248089 A | 8/2008 |
| CN | 101355965 A | 1/2009 |
| CN | 101622540 A | 1/2010 |
| CN | 102250911 A | 11/2011 |
| CN | 102428179 A | 4/2012 |
| CN | 102740887 A | 10/2012 |
| CN | 104470949 A | 3/2015 |
| EP | 2420839 A2 | 2/2012 |
| EP | 2926142 B1 | 7/2018 |
| JP | 2006-340714 A | 12/2006 |
| JP | 2008-544755 A | 12/2008 |
| JP | 2012-503984 A | 2/2012 |
| JP | 2017-514966 A | 6/2017 |
| JP | 2017-514967 A | 6/2017 |
| RU | 2315312 C2 | 1/2008 |
| RU | 2395090 C2 | 7/2010 |
| WO | WO-01/039722 A2 | 6/2001 |
| WO | WO-2004/013632 A1 | 2/2004 |
| WO | WO-2006/042237 A2 | 4/2006 |
| WO | WO-2006/121168 A1 | 11/2006 |
| WO | WO-2006/133396 A2 | 12/2006 |
| WO | WO-2007/005874 A2 | 1/2007 |
| WO | WO-2007/047955 A2 | 4/2007 |
| WO | WO-2007/082154 A2 | 7/2007 |
| WO | WO-2008/104953 A2 | 9/2008 |
| WO | WO-2010/036959 A2 | 4/2010 |
| WO | WO-2010/056735 A1 | 5/2010 |
| WO | WO-2010/077634 A1 | 7/2010 |
| WO | WO-2011/041613 A2 | 4/2011 |
| WO | WO-2011/041613 A3 | 4/2011 |
| WO | WO-2011/066389 A1 | 6/2011 |
| WO | WO-2012/003476 A2 | 1/2012 |
| WO | WO-2012/031027 A1 | 3/2012 |
| WO | WO-2012/037378 A2 | 3/2012 |
| WO | WO-2012/145493 A1 | 10/2012 |
| WO | WO-2013/079174 A1 | 6/2013 |
| WO | WO-2013/148498 A1 | 10/2013 |
| WO | WO-2013/172926 A1 | 11/2013 |
| WO | WO-2013/173223 A1 | 11/2013 |
| WO | WO-2013/173233 A1 | 11/2013 |
| WO | WO-2014/022758 A1 | 2/2014 |
| WO | WO-2013/019906 A9 | 3/2014 |
| WO | WO-2014/100079 A1 | 6/2014 |
| WO | WO-2014/165082 A2 | 10/2014 |
| WO | WO-2014/165422 A1 | 10/2014 |
| WO | WO-2014/194293 A1 | 12/2014 |
| WO | WO-2015/013388 A2 | 1/2015 |
| WO | WO-2015/033172 A1 | 3/2015 |
| WO | WO-2015/033173 A1 | 3/2015 |
| WO | WO-2015/036499 A1 | 3/2015 |
| WO | WO-2015/038538 A1 | 3/2015 |
| WO | WO-2015/061668 A1 | 4/2015 |
| WO | WO-2015/088930 A1 | 6/2015 |
| WO | WO-2015/124703 A1 | 8/2015 |
| WO | WO-2015/171588 A1 | 11/2015 |
| WO | WO-2015/172284 A1 | 11/2015 |
| WO | WO-2015/181342 A1 | 12/2015 |
| WO | WO-2015/181343 A2 | 12/2015 |
| WO | WO-2016/007235 A1 | 1/2016 |
| WO | WO-2017/196867 A1 | 11/2017 |

OTHER PUBLICATIONS

Extended European Search Report for European Patent Application No. 23217779.0, dated Jun. 6, 2024 (12 pages).

"A Global Study to Assess the Effects of MEDI4736 Following Concurrent Chemoradiation in Patients With Stage III Unresectable Non-Small Cell Lung Cancer (PACIFIC)," U.S. National Institutes of Health, <https://clinicaltrials.gov/ct2/show/record/NCT02125461?term=medi4736+nsclc>, last updated May 1, 2017, retrieved on May 3, 2017 (7 pages).

"A Global Study to Assess the Effects of MEDI4736 Following Concurrent Chemoradiation in Patients With Stage III Unresectable Non-Small Cell Lung Cancer (PACIFIC)," U.S. National Institutes of Health, <https://www.clinicaltrials.gov/ct2/show/NCT02125461>, last updated Mar. 25, 2015, retrieved on May 21, 2015 (4 pages).

"A Global Study to Assess the Effects of MEDI4736 Following Concurrent Chemoradition in Patients With Stage III Unresectable Non-Small Cell Lung Cancer (PACIFIC)", <https://clinicaltrials.gov/ct2/show/NCT02125461?term=medi4736+nsclc&rank=3>, dated Feb. 13, 2017, retrieved Nov. 11, 2020 (11 pages).

"Assessment Run 36 2012, Cytokeratin, pan-(CK-PAN)," NordiQC, <https://www.nordiqc.org/downloads/assessments/36_85.pdf> last accessed Nov. 16, 2020, (6 pages).

"A Study of Atezolizumab (an Engineered Anti-Programmed Death-Ligand 1 [PDL1] Antibody) to Evaluate Safety, Tolerability and Pharmacokinetics in Participants With Locally Advanced or Metastatic Solid Tumors," retrieved on Jan. 8, 2018, from <https://clinicaltrials.gov/ct2/show/NCT01375842> (12 pages).

"About HCDM," Human Cell Differentiation Molecules, <http://www.hcdm.org/index.php/about-hcdm>, retrieved Nov. 16, 2020 (5 pages).

"Breast Cancer," Wikipedia, <https://en.wikipedia.org/w/index.php?title=Brea%20st%20cancer&oldid=525497239>, retrieved on Jul. 23, 2019 (19 pages).

"Cancer Immunology: Pivotal Cancer Immunology Targets", <http://www.cellsignal.com/contents/science-cancer-research/pivotal-tumor-immunology-targets-pd-l1/pd-li-signaling>, published in 2017, retrieved Nov. 11, 2020 (5 pages).

"Catalogue d'anticorps 2011," AbD Serotec, <www.abdserotec.com/france> (2 pages).

"CD274 CD274 molecule [*Homo sapiens* (human)]," NCBI, <https://www.ncbi.nlm.nih.gov/gene/29126>, published 2015, retrieved Nov. 25, 2020 (10 pages).

"CD Marker Handbook," BD Biosciences, <https://www.bdbiosciences.com/documents/cd_marker_handbook.pdf>, last accessed Nov. 16, 2020 (56 pages).

"Estrogen Receptor," Wikipedia, <https://en.wikipedia.org/w/index.php?title=Estrogen_receptor&oldid=517956676>, retrieved Jul. 23, 2019 (7 pages).

"HER2/neu," Wikipedia, <https://en.wikipedia.org/w/index.php?title=HER2/neu&oldid=519951136>, retrieved on Jul. 23, 2019 (8 pages).

"History of Changes for Study: NCT01772004", submitted Jan. 16, 2013 (v1), <https://www.clinicaltrials.gov/ct2/history/NCT01772004?V_1=View#StudyPageTop>, retrieved Aug. 12, 2020 (5 pages).

*Immunohistochemical Staining Methods: IHC Guidebook, Sixth Edition.* Dako Denmark A/S, (2013) (218 pages).

"Investigational Immunotherapy Anti-PDL1 (MPDL3280A) Shrank Tumors in 43 Percent of People With a Specific Type of Metastatic Bladder Cancer in a Genentech Study", Roche, <www.gene.com/

(56)                References Cited

OTHER PUBLICATIONS media/press-releases/14566/2014-05-31/investigational-immunotherapy-anti-pdl1>, published May 31, 2014, retrieved Nov. 25, 2020 (5 pages).

"Merck Serono Initiates Phase II Study of Anti-PD-L1 Antibody MSB0010718C in Metastatic Merkel Cell Carcinoma", retrieved Nov. 25, 2020, published in 2017 at <http://www.fiercebiotech.com/press-releases/merck-serono-initiates-phase-ii-study-anti-pd-l1-antibody-msb0010718c-metas> (5 pages).

"Multiplex Tissue Biomarkers in Context," PerkinElmer, Inc. (2014) (2 pages).

"NCI Drug Dictionary", National Cancer Institute, 2015, at <http://www.cancer.gov/publications/dictionaries>, retrieved Nov. 25, 2020 (33 pages).

"NCI Drug Dictionary: pembrolizumab," National Cancer Institute, published 2017 at <http:www.cancer.gov/drugdictionary?cdrid=695789> retrieved Nov. 25, 2020 (1 page).

"OptiView Detection Chemistry," Ventana Medical Systems, Inc. (2011) (4 pages).

"Pan Cytokeratin (pan CK) Monoclonal Antibody (AE1+AE3), TrueMAB™, " Thermofisher Scientific, <https://www.thermofisher.com/antibody/product/pan-Cytokeratin-pan-CK-Antibody-clone-AE1-AE3-Monoclonal/CF190321>, retrieved on May 28, 2021 (7 pages).

"PD-L1," Wikipedia, <https://en.wikipedia.org/w/index.php?title=PD-L1&oldid=451891615>, retrieved on Jul. 23, 2019 (5 pages).

"PD-L1 (E1L3N®) XP® Rabbit mAb #13684," Cell Signaling Technology, <http://www.cellsignal.com/products/primary-antibodies/13684id=proteomics&utm_source=SalesFlyer&utm_medium=offline&utm_campaign=NPI&utm_content=PDL 1>, retrieved on May 3, 2017 (12 pages).

"Pivotal Cancer Immunology Targets: New Rabbit mAbs for B7-H3 and B7-H4," Cell Signaling Technology, <http://www.cellsignal.com/contents/science-cancer-research/pivotal-tumor-immunology-targets-pdl1/pd-li-signaling>, retrieved on Dec. 1, 2020, printed May 21, 2015 (5 pages).

"Programmed Cell Death Protein 1," Wikipedia, <https:en.wikipedia.org/w/index.php?title=Programmed_cell_death_protein_l&oldid=519305474>, retrieved Jul. 24, 2019 (6 pages).

"Q9NZQ7—PD1L1_HUMAN," UniProt, <http://www.uniprot.org/uniprot/Q9NZQ7>, retrieved on May 21, 2015 (9 pages).

"Ruo Discovery Universal Staining procedure for Discovery Ultra Research Instrument," Ventana Medical Systems, Inc. (Nov. 2014) (3 pages).

"Spring Bioscience launches highly sensitive PD-L1 (SP142) antibody for immunotherapy research," Spring Bioscience, dated Aug. 25, 2014 (3 pages).

"Targeted Therapy," Wikipedia, <https://en.wikipedia.org/w/index.php?title=Targeted_therapy&oldid=522675520>, retrieved Aug. 2, 2019 (4 pages).

"Trastuzumab," Wikipedia, <https://en.wikipedia.org/w/index.php?title=Trastuzumab&oldid=525138397>, retrieved Jul. 23, 2019 (9 pages).

"UniProtKB—Q9NZQ7 (PD1L1_HUMAN)," UniProt, <http://www.uniprot.org/uniprot/Q9NZQ7>, retrieved on Jul. 22, 2015 (6 pages).

"Ventana Medical Systems, Inc. and MedImmune collaborate to develop a custom PD-L1 Assay for immunotherapy clincial trials," Ventana Medical Systems, Inc., dated Jun. 4, 2014 (2 pages).

Afanasiev et al., "Merkel polyomavirus-specific T cells fluctuate with Merkel cell carcinoma burden and express therapeutically targetable PD-1 and Tim-3 exhaustion markers," Clin Cancer Res. 19(19):5351-5360 (2013) (11 pages).

Ali et al., "PD-L1 protein expression in breast cancer is rare, enriched in basal-like tumours and associated with infiltrating lymphocytes," Annals of Oncology. 26(7):1488-1493 (2015).

Almagro et al., "Humanization of antibodies," Front Biosci. 13:1619-33 (2008).

Altree-Tacha et al., "Multiplex Cocktails for Immunotherapy Targets: PD-L1 with Tumor Specific Transcription Factors," Biocare Medical. Presented at USCAP 2017, Poster #297 (2017) (4 pages).

Bendig, Mary M., "Humanization of Rodent Monoclonal Antibodies by CDR Grafting," Methods: A Companion to Methods in Enzymology. 8:83-93 (1995).

Berglund et al., "The Epitope space of the human proteome," Protein Science. 17(4):606-613 (2008).

Bontkes et al., "Assessment of cytotoxic T-lymphocyte phenotype using the specific markers granzyme B and TIA-1 in cervical neoplastic lesions," Br J Cancer. 76(10):1353-60 (1997).

Brahmer et al., "Safety and Activity of Anti-PD-L1 Antibody in Patients with Advanced Cancer," N Engl J Med. 366(26):2455-65 (2012).

Brodská et al., "Correlation of PD-L1 Surface Expression on Leukemia Cells with the Ratio of PD-L1 mRNA Variants and with Electrophoretic Mobility," Cancer Immunol Res. 4(10):815-9 (2016) (6 pages).

Brown et al., "Blockade of programmed death-1 ligands on dendritic cells enhances T cell activation and cytokine production," J Immunol. 170(3):1257-66 (2003).

Brown et al., "Tolerance of single, but not multiple, amino acid replacements in antibody VH CDR2: a means of minimizing B cell wastage from somatic hypermutation?" J Immunol. 156(9):3285-91 (1996).

Butte et al., "Programmed Death-1 Ligand 1 Interacts Specifically with the B7-1 Costimulatory Molecule to Inhibit T Cell Responses," Immunity. 27(1):111-122 (2007).

Calles et al., "Differential expression of LKB1, PD-L1, and PD-L2 in KRAS-mutant non-small cell lung cancer in never-smokers," J Clin Oncol. 32(15 suppl):8032 (Abstract) (2014).

Capelozzi et al., "Role of Immunohistochemistry in the diagnosis of lung cancer," J Bras Pneumol. 35(4):375-382 (2009).

Carter et al., "PD-1/PD-L inhibitory pathway affects both CD4 and CD8 T cells and is overcome by IL-2," Eur J Immunol. 32(3):634-643 (2002).

Chakravarti et al., "Predictive factors of activity of anti-programmed death-1/programmed death ligand-1 drugs: immunohistochemistry analysis," Trans Lung Cancer Res. 4(6):743-751 (2015).

Chen et al., "Molecular pathways: next-generation immunotherapy—inhibiting programmed death-ligand 1 and programmed death-1," Clin Cancer Res. 18(24):6580-7 (2012).

Chen et al., "PD-L1 expression is characteristic of a subset of aggressive B-cell lymphomas and virus-associated malignancies," Clin Cancer Res. 19(13):3462-73 (2013).

Cheong et al., "Unexpected Epithelial Membrane Antigen (EMA) and Cytokeratin Expression in a Case of Infantile Acute Monoblastic Leukaemia," Hematology. 1(3):223-5 (1996).

Choueiri et al., "Correlation of PD-L1 Tumor Expression and Treatment Outcomes in Patients with Renal Cell Carcinoma Receiving Sunitinib or Pazopanib: Results from COMPARZ, a Randomized Controlled Trial," Clin Cancer Res. 21(5):1071-7 (2015).

Colman, "Effects of amino acid sequence changes on antibody-antigen interactions," Research in Immunology. 145:33-36 (1994).

Corada et al., "Monoclonal antibodies directed to different regions of vascular endothelial cadherin extracellular domain affect adhesion and clustering of the protein and modulate endothelial permeability," Blood. 97(6):1679-84 (2001) (7 pages).

Cunha et al., "Infiltration of a mixture of different immune cells may be related to molecular profile of differentiated thyroid cancer," Endocr Relat Cancer. 19(3):L31-6 (2012).

Curiel et al., "Blockade of B7-H1 improves myeloid dendritic cell-mediated antitumor immunity," Nat Med. 9(5):562-7 (2003).

Day et al., "Covalently deposited dyes: a new chromogen paradigm that facilitates analysis of multiple biomarkers in situ," Lab Invest. 97(1):104-13 (2017).

Daoud et al., "The value of triple antibody (34betaE12+p63+ AMACR) cocktail stain in radical prostatectomy specimens with crushed surgical margins," J Clin Pathol. 65(5):437-40 (2012) (5 pages).

D'Angelo et al., "Prevalence of tumor infiltrating lymphocytes and PD-L1 expression in the soft tissue sarcoma microenvironment," available in PMC Jul. 11, 2017, published in final edited form as: Hum Pathol. 46(3):357-65 (2015) (19 pages).

(56) References Cited

OTHER PUBLICATIONS

D'Eliseo et al., "Granzyme B is expressed in urothelial carcinoma and promotes cancer cell invasion," Int J Cancer. 127(6):1283-94 (2010).

De Genst et al., "Antibody repertoire development in camelids," Dev Comp Immunol. 30(1-2):187-98 (2006).

Dong et al., "Tumor-associated B7-H1 promotes T-cell apoptosis: a potential mechanism of immune evasion," Nat Med. 8(8): 793-800 (2002).

Esteva et al., "CD40 signaling predicts response to preoperative trastuzumab and concomitant paclitaxel followed by 5-fluorouracil, epirubicin, and cyclophosphamide in HER-2-overexpressing breast cancer," Breast Cancer Res. 9(6):R87 (2007) (9 pages).

Freeman et al., "Engagement of the PD-1 Immunoinhibitory Receptor by a Novel B7 Family Member Leads to Negative Regulation of Lymphocyte Activation," J of Exp Med. 192(7):1027-1034 (2000).

Gaiser et al., "Tyramide signal amplification: an enhanced method for immunohistochemistry on methyl-methacrylate-embedded bone marrow trephine sections," Acta Haematol. 117(2):122-7 (2007).

Geng et al., "B7-H1 up-regulated expression in human pancreatic carcinoma tissue associates with tumor progression," J Cancer Res Clin Oncol. 134(9):1021-7 (2008).

Ghebeh et al., "FOXP3+ Tregs and B7-H1+/PD-1+ T lymphocytes co-infiltrate the tumor tissues of high-risk breast cancer patients: Implication for immunotherapy," BMC Cancer. 8:57 (2008) (12 pages).

Ghebeh et al., "The B7-H1 (PD-L1) lymphocyte-inhibitory molecule is expressed in breast cancer patients with infiltrating ductal carcinoma: correlation with important high-risk prognostic factors," Neoplasia. 8(3):190-8 (2006).

Ginter et al., "The Minimal Carcinoma Triple Stain Is Superior to Commercially Available Multiplex Immunohistochemical Stains," Am J Clin Pathol. 144(6):869-79 (2015).

Gustmann et al., "Cytokeratin expression and vimentin content in large cell anaplastic lymphomas and other non-Hodgkin's lymphomas," Am J Pathol. 138(6):1413-22 (1991).

Hamanishi et al., "Programmed cell death 1 ligand 1 and tumor-infiltrating CD8+ T lymphocytes are prognostic factors of human ovarian cancer," Proc Natl Acad Sci U S A. 104(9):3360-5 (2007).

Hamid et al., "Anti-programmed death-1 and anti-programmed death-ligand 1 antibodies in cancer therapy," Expert Opin Biol Ther. 13(6):847-61 (2013).

Hawes et al., "Chapter 5: Immunohistochemistry," *Modern Surgical Pathology* (*Second Edition*). Noel Weidner, Richard J. Cote, Saul Suster, and Lawrence M. Weiss. 1:48-70 (2009).

Herawi et al., "Immunohistochemical Antibody Cocktail Staining (p63/HMWCK/AMACR) of Ductal Adenocarcinoma and Gleason Pattern 4 Cribriform and Noncribriform Acinar Adenocarcinomas of the Prostate," Am J Surg Pathol. 31(6):889-94 (2007) (7 pages).

Hirsch et al., "PD-L1 Immunohistochemistry Assays for Lung Cancer: Results from Phase 1 of the Blueprint PD-L1 IHC Assay Comparison Project," J Thorac Oncol. 12(2):208-22 (2017).

Huang et al., "Detecting cell-in-cell structures in human tumor samples by E-cadherin/CD68/CD45 triple staining," Oncotarget. 6(24):20278-87 (2015).

Iwai et al., "Involvement of PD-L1 on tumor cells in the escape from host immune system and tumor immunotherapy by PD-L1 blockade," PNAS. 99(19):12293-12297 (2002).

Iwai et al., "PD-1 blockade inhibits hematogenous spread of poorly immunogenic tumor cells by enhanced recruitment of effector T cells," Int Immunol. 17(2):133-44 (2004).

Kalra et al., "Multiplex Immunohistochemistry for Mapping the Tumor Microenvironment," *Signal Transduction Immunohistochemistry: Methods and Protocols*, Methods in Molecular Biology, vol. 1554. Springer Science+Business Media LLC, 237-51 (2017).

Kohrt et al., "Intratumoral characteristics of tumor and immune cells at baseline and on-treatment correlated with clinical responses to MPDL3280A, an engineered antibody against PD-L1," J Immunotherapy Cancer. 1(Suppl 1):012 (2013) (1 page).

Konishi et al., "B7-H1 expression on non-small cell lung cancer cells and its relationship with tumor-infiltrating lymphocytes and their PD-1 expression," Clin Cancer Res. 10(15):5094-100 (2004) (8 pages).

Kreienberg et al., "Interdisciplinary GoR level III Guidelines for the Diagnosis, Therapy and Follow-up Care of Breast Cancer: Short version—AWMF Registry No. 032-045OL," Geburtshilfe Frauenheilkd. 73(6):556-583 (2013) (28 pages).

Kwak et al., "A convenient method for epitope competition analysis of two monoclonal antibodies for their antigen binding," J Immunol Methods. 191(1):49-54 (1996).

Latchman et al., "PD-L2 is a second ligand for PD-1 and inhibits T cell activation," Nature Immunology. 2(3):261-268 (2001).

Lee et al., "Immunofluorescent Triple-Staining Technique to Identify Sensory Nerve Endings in Human Thumb Ligaments," Cells Tissues Organs. 195(5):456-64 (2012) (10 pages).

Lehr et al., "Complete Chromogen Separation and Analysis in Double Immunohistochemical Stains Using Photoshop-based Image Analysis," J Histochem Cytochem. 47(1):119-25 (1999).

Levenson et al., "Immunohistochemistry and mass spectrometry for highly multiplexed cellular molecular imaging," Lab Invest. 95(4):397-405 (2015).

Lloyd et al., "Phenotyping immune cells in-situ. An investigation of the spatial heterogeneity of specific immune cell phenotypes in the tumour microenvironment," Perkin Elmer University of Manchester. (2014) (1 page).

Lyford-Pike et al., "Evidence for a Role of the PD-1:PD-L1 Pathway in Immune Resistance of HPV-Associated Head and Neck Squamous Cell Carcinoma," Cancer Res. 73(6):1733-41 (2013).

Mahoney et al., "Antibodies to the cytoplasmic domain of PD-L1 most clearly delineate cell membranes in immunohistochemical staining," available in PMC Dec. 1, 2016, pusblished in final edited form as: Cancer Immunol Res. 3(12):1308-15 (2015) (16 pages).

McLaughlin et al., "Domain-specific PD-L1 protein measurement in non-small cell lung cancer (NSCLC)," 2014 ASCO Annual Meeting. J Clin Oncol. 32(15 suppl): Abstract 8064 (2014) (2 pages).

McLaughlin et al., "Domain-specific PD-L1 protein measurement in non-small cell lung cancer (NSCLC)," Journal of Clinical Oncology. 32(15_suppl):8064, Abstract 8064 (May 20, 2014) (1 page) (Abstract only).

Melero et al., "Clinical Development of Immunostimulatory Monoclonal Antibodies and Opportunities for Combination," Clin Cancer Res. 19(5): 997-1008 (2013).

Miller, "Cytokeratin AE1/AE3," ProPath. Last revised Nov. 2003, <https://propath.com/cytokeratin-ae1-ae3/>, accessed May 27, 2021 (3 pages).

Mitchell, "Combinations of anticancer drugs and immunotherapy," Cancer Immunol Immunother. 52(11):686-92 (2003).

Molina et al., "Trastuzumab (herceptin), a humanized anti-Her2 receptor monoclonal antibody, inhibits basal and activated Her2 ectodomain cleavage in breast cancer cells," Cancer Res. 61(12):4744-9 (2001).

Mu et al., "High expression of PD-L1 in lung cancer may contribute to poor prognosis and tumor cells immune escape through suppressing tumor infiltrating dendritic cells maturation," Med Oncol. 28(3):682-8 (2011).

Mullane et al., "PD-L1 expression in mononuclear cells and not in tumor cells, correlated with prognosis in metastatic urothelial carcinoma," <http://meetinglibrary.asco.org/print/1736722>, retrieved on Sep. 8, 2015 (2 pages).

Nelson et al., "Automated prognostic pattern detection shows favorable diffuse pattern of FOXP3+ Tregs in follicular lymphoma," Br J Cancer. 113(8):1197-205 (2015).

Ogata et al., "Differences in blast immunophenotypes among disease types in myelodysplastic syndromes: a multicenter validation study," Leuk Res. 36(10):1229-36 (2012).

Ohigashi et al., "Clinical Significance of Programmed Death-1 Ligand-1 and Programmed Death-1 Ligand-2 Expression in Human Esophageal Cancer," Clin Cancer Res. 11(8):2947-2953 (2005) (8 pages).

Padlan, "X-ray crystallography of antibodies," Adv Protein Chem. 49:57-133 (1996).

(56) References Cited

OTHER PUBLICATIONS

Park et al., "V-ets erythroblastosis virus E26 oncogene homolog (avian)/Trefoil factor 3/high-molecular-weight cytokeratin triple immunostain: a novel tissue-based biomarker in prostate cancer with potential clinical application," Hum Pathol. 44:2282-92 (May 17, 2013).
Paul, Chapter 9: Structure and Function of Immunoglobulins. Fundamental Immunology, Third Edition. Raven Press, 292-295 (1993) (6 pages).
Peng et al., "PD-1 blockade enhances T-cell migration to tumors by elevating IFN-gamma inducible chemokines," Cancer Res. 72(20):5209-18 (2012).
Powderly et al., "Biomarkers and associations with the clinical activity of PD-L1 blockade in a MPDL3280A study," <https://meetinglibrary.asco.org/record/83742/abstract>, retrieved May 2, 2018 (21 pages).
Ramos-Vara, "Technical Aspects of Immunohistochemistry," Vet Pathol. 42(4):405-26 (2005).
Rebelatto et al., "Development of a PD-L1 companion diagnostic assay for treatment with MEDI4736 in NSCLC and SCCHN patients," J Clin Oncol. 33(15):1-3 (2015).
Ribas et al., "The Future of Cancer Therapy: Selecting Patients Likely to Respond to PD1/L1 Blockade," Clin Cancer Res. 20(19):4982-4 (2014).
Rosenblatt et al., "Targetting the PD-L1/PD-1 axis holds promise in the treatment of malignancy," Transl Cancer Res. 1(4):283-6 (2012).
Ross et al., "The Diagnostic Utility of the Minimal Carcinoma Triple Stain in Breast Carcinomas," Am J Clin Pathol. 139(1):62-70 (Jan. 2013).
Rudikoff et al., "Single amino acid substitution altering antigen-binding specificity," Proc Natl Acad Sci U S A. 79(6):1979-83 (1982).
Sasaki et al., "PD-L1 gene expression in Japanese lung cancer patients," Biomed Rep. 1(1):93-96 (2013).
Shen et al., "Impaired ICOSL in human myeloid dendritic cells promotes Th2 responses in patients with allergic rhinitis and asthma," Clin Exp Allergy. 44(6):831-41 (Feb. 27, 2014).
Sung et al., "Alpha-methylacyl-CoA racemase (P504S)/34betaE12/p63 triple cocktail stain in prostatic adenocarcinoma after hormonal therapy," Hum Pathol. 38(2):332-41 (2007).
Stack et al., "Multiplexed immunohistochemistry, imaging, and quantification: A review, with an assessment of Tyramide signal amplification, multispectral imaging and multiplex analysis," Methods. 70(1):46-58 (Aug. 29, 2014).
Stagg et al., "Anti-ErbB-2 mAb therapy requires type I and II interferons and synergizes with anti-PD-1 or anti-CD137 mAb therapy," Proc Natl Acad Sci USA. 108(17):7142-7 (2011).
Stagg et al., "Supporting Information," Proc Natl Acad Sci USA. doi: 10.1073/pnas.1016569108 (2011) (5 pages).
Sznol et al., "Antagonist antibodies to PD-1 and B7-H1 (PD-L1) in the treatment of advanced human cancer," Clin Cancer Res. 19(5):1021-34 (2013).
Taube et al., "Colocalization of inflammatory response with B7-h1 expression in human melanocytic lesions supports an adaptive resistance mechanism of immune escape," available in PMC Feb. 10, 2013, published in final edited form as: Sci Transl Med. 4(127):127ra37 (2012) (22 pages).
Taube et al., "Association of PD-1, PD-1 Ligands, and Other Features of the Tumor Immune Microenvironment with Response to Anti-PD-1 Therapy," Clin Cancer Res. 20(19):5064-74 (2014) (12 pages).
Takada et al., "An Immunohistochemical Analysis of PD-L1 Protein Expression in Surgically Resected Small Cell Lung Cancer Using Different Antibodies and Criteria," Anticancer Res. 36(7):3409-12 (2016).
Topalian et al., "Safety, Activity, and Immune Correlates of Anti-PD-1 Antibody in Cancer," N Engl J Med. 366(26):2443-54 (2012).

Topalian et al., "Targeting the PD-1/B7-H1(PD-L1) pathway to activate anti-tumor immunity," available in PMC Apr. 1, 2013, published in final edited form as: Curr Opin Immunol. 24(2):207-12 (2012) (11 pages).
Tóth et al., "Simultaneous Visualization of Multiple Antigens With Tyramide Signal Amplification Using Antibodies From the Same Species," J Histochem Cytochem. 55(6):545-54 (2007).
Tumeh et al., "PD-1 blockade induces responses by inhibiting adaptive immune resistance," Nature. 515(7528):568-571 (2014).
Tzartos, "Epitope Mapping by Antibody Competition: Methodology and Evaluation of the Validity of the Technique." Methods in Molecular Biology, Vol. 66. Epitope Mapping Protocols. Humana Press, Inc., 55-66 (1996).
Untch et al., "Neoadjuvant treatment with trastuzumab in HER2-positive breast cancer: results from the GeparQuattro study," J Clin Oncol. 28(12):2024-31 (2010).
Van der Loos, "Chromogens in Multiple Immunohistochemical Staining Used for Visual Assessment and Spectral Imaging: The Colorful Future," The Journal of Histotechnology. 33(1):31-40 (2010) (11 pages).
Van der Loos, "Multiple Immunoenzyme Staining: Methods and Visualizations for the Obersevation With Spectral Imaging," J Histochem Cytochem. 56(4):313-28 (2008).
Vanneman et al., "Combining immunotherapy and targeted therapies in cancer treatment," Nat Rev Cancer. 12(4):237-51 (2012).
Velcheti et al., "Programmed death ligand-1 expression in non-small cell lung cancer," Lab Invest. 94(1):107-16 (2014).
Warford et al., "Antigen retrieval, blocking, detection and visualisation systems in immunohistochemistry: a review and practical evaluation of tyramide and rolling circle amplification systems," Methods. 70(1):28-33 (2014).
Weber et al., "Safety, Efficacy, and Biomarkers of Nivolumab With Vaccine in Ipilimumab-Refractory or -Naive Melanoma," J Clin Oncol. 31(34):4311-4318 (2013) (10 pages).
Weber, "Immune checkpoint proteins: a new therapeutic paradigm for cancer—preclinical background: CTLA-4 and PD-1 blockade," Semin Oncol. 37(5):430-9 (2010).
Willis et al., "SOX10: A Useful Marker for Identifying Metastatic Melanoma in Sentinel Lymph Nodes," Appl Immunohistochem Mol Morphol. 23(2):109-12 (2015) (5 pages).
Xu et al., "Loss of Lkb1 and Pten leads to lung squamous cell carcinoma with elevated PD-L1 expression," Cancer Cell. 25(5):590-604 and supplemental information (2014) (39 pages).
Yan et al., "MYC Expression in Concert with BCL2 and BCL6 Expression Predicts Outcome in Chinese Patients with Diffuse Large B-Cell Lymphoma, Not Otherwise Specified," PLoS One. 9(8):e104068 (Aug. 4, 2014) (16 pages).
Yanagita et al., "Rapid Multiplex Immunohistochemistry Using the 4-antibody Cocktail YANA-4 in Differentiating Primary Adenocarcinoma From Squamous Cell Carcinoma of the Lung," Appl Immunohistochem Mol Morphol. 19(6):509-13 (2011) (6 pages).
Yunmei et al., "VSIG4 expression on macrophages facilitates lung cancer development," Lab Invest. 94(7):706-715 (2014).
Zhang et al., "Chemopreventive agents induce programmed death-1-ligand 1 (PD-L1) surface expression in breast cancer cells and promote PD-L1-mediated T cell apoptosis," Mol Immunol. 45(5):1470-6 (2008).
Zhang et al., "PD-1/PD-L1 interactions inhibit antitumor immune responses in a murine acute myeloid leukemia model," Blood. 114(8):1545-52 (2009).
Certified U.S. Appl. No. 61/895,543, filed Oct. 25, 2013, received by the International Bureau on Dec. 21, 2014 in connection to International Application No. PCT/US2014/062149 (98 pages).
Communication pursuant to Article 94(3) EPC for European Patent Application No. 14714119.6, dated Aug. 7, 2018 (7 pages).
Communication pursuant to Article 94(3) EPC for European Patent Application No. 14714119.6, dated Nov. 30, 2017 (9 pages).
Communication pursuant to Article 94(3) for European Patent Application No. 14714119.6, dated Feb. 17, 2017 (7 pages).
Communication pursuant to Article 94(3) for European Patent Application No. 19191154.4, dated Mar. 29, 2021 (7 pages).

(56)                References Cited

OTHER PUBLICATIONS

Decision of Rejection for Japanese Patent Application No. 2016-501626, issued Jul. 17, 2018 (4 pages).
English Translation of Search Report and Written Opinion for Brazilian Patent Application No. BR112015023120-9, dated Aug. 27, 2019 (4 pages).
English Translation of Second Office Action for Chinese Patent Application No. 201480027406.7, dated Mar. 13, 2017 (12 pages).
English Translation of Third Office Action for Chinese Patent Application No. 201480027406.7, dated Nov. 3, 2017 (9 pages).
Examination Report for Australian Patent Application No. 2017225061, dated Nov. 7, 2018 (4 pages).
Examination Report for New Zealand Patent Application No. 751260, dated Jul. 17, 2020 (8 pages).
Examination Report No. 1 for Australian Patent Application No. 2019271922, dated Mar. 29, 2021 (4 pages).
Examination Report No. 2 for Australian Patent Application No. 2014235453, dated Sep. 8, 2017 (4 pages).
Examination Report No. 2 for Australian Patent Application No. 2017225061, dated Oct. 17, 2019 (4 pages).
Extended European Search Report for European Patent Application No. 19191154.4, dated Feb. 13, 2020 (11 pages).
First Office Action for Chinese Patent Application No. 201480027406.7, dated May 20, 2016 (19 pages).
International Preliminary Report on Patentability for International Patent Application No. PCT/US2014/024746, issued Sep. 15, 2015 (13 pages).
International Preliminary Report on Patentability for International Patent Application No. PCT/US2015/033395, issued Jan. 17, 2017 (8 pages).
International Preliminary Report on Patentability for PCT/EP2015/061922, issued Dec. 6, 2016 (9 pages).
International Preliminary Report on Patentability for PCT/EP2016/052107, issued on Aug. 8, 2017 (8 pages).
International Search Report and Written Opinion for International Patent Application No. PCT/US2015/033395, mailed Aug. 5, 2015 (15 pages).
International Search Report and Written Opinion for PCT/EP2015/061922, mailed Dec. 22, 2015 (13 pages).
International Search Report and Written Opinion for PCT/EP2016/052107, mailed on Apr. 5, 2016, (7 pages).
International Search Report for International Patent Application No. PCT/US2014/024746, mailed Sep. 29, 2014 (8 pages).
International Search Report for PCT/US2014/062149, issued Feb. 23, 2015, (3 pages).
Notice of Final Rejection for Korean Patent Application No. 10-2015-7029278, dated Feb. 28, 2018 (12 pages).
Notice of Final Rejection for Korean Patent Application No. 10-2018-7026186, dated Feb. 24, 2020 (7 Pages).
Notice of Preliminary Rejection for Korean Patent Application No. 10-2018-7026186, dated Apr. 16, 2019 (45 pages).
Notice of Preliminary Rejection for Korean Patent Application No. 10-2020-7026646, dated Nov. 24, 2020, (45 pages).
Notice of Reasons for Rejection for Japanese Patent Application No. 2016-501626, dated Oct. 4, 2016 (8 pages).
Notice of Reasons for Rejection for Japanese Patent Application No. 2016-501626, dated Sep. 12, 2017 (9 pages).
Notice of Reasons for Rejection for Japanese Patent Application No. 2018-216412, dated Nov. 5, 2019 (2 pages).
Notice of Reasons for Rejection for Japanese Patent Application No. 2018-216412, dated Sep. 8, 2020 (6 pages).
Notification of Defects for Israeli Patent Application No. 241309, dated Dec. 27, 2018 (5 pages).
Office Action for Canadian Patent Application No. 2,905,798, dated Dec. 19, 2019 (7 pages).

Office Action for Canadian Patent Application No. 2,905,798, dated Apr. 24, 2018 (6 pages).
Office Action for Russian Patent Application No. 2015139224, dated Mar. 12, 2018 (20 pages).
Office Action for Russian Patent Application No. 2015139224, dated Nov. 6, 2018 (7 pages).
Office Action for U.S. Appl. No. 14/725,288, mailed Apr. 6, 2017 (32 pages).
Office Action for Mexican Patent Application No. MX/a/2017/000419, dated Jan. 22, 2021 (8 pages).
Patent Examination Report 2 for New Zealand Patent Application No. 712314, dated Mar. 4, 2021 (6 pages).
Patent Examination Report 2 for New Zealand Patent Application No. 751260, dated Mar. 4, 2021 (6 pages).
Patent Examination Report 2 for New Zealand Patent Application No. 751264, dated Mar. 4, 2021 (7 pages).
Search Report for Chinese Patent Application No. 201480027406.7, dated May 11, 2016 (5 pages).
Search Report for Singaporean Patent Application No. 11201507333X, dated Jul. 8, 2016 (5 pages).
Substantive Examination for Malaysian Patent Application No. PI 2017000043, dated Feb. 18, 2020, (5 pages).
Written Opinion for Singaporean Patent Application No. 11201507333X, dated Sep. 6, 2016 (8 pages).
Written Opinion for Singaporean Patent Application No. 11201700207W, dated Nov. 6, 2017 (8 pages).
Broderick, "Avelumab Fails to Improve OS in Phase III Gastric Cancer Trial," Targeted Onc., <https://www.targetedonc.com/view/avelumab-fails-to-improve-os-in-phase-iii-gastric-cancer-trial> dated Nov. 29, 2017, retrieved May 24, 2023 (3 pages).
Holets et al., "Differentiation-Induced Post-Transcriptional Control of B7-H1 in Human Trophoblast Cells" Placenta, Jan. 31, 2009 vol. 30, No. 1, p. 48-55, retrieved on Dec. 21, 2021, from <https://www.sciencedirect.com/science/article/abs/pii/S0143400408003354>, (7 pages).
Naidoo et al., "Toxicities of the anti-PD-1 and anti-PD-L1 immune checkpoint antibodies," Annals of Oncology. 26(12):2365-91 (Dec. 2015) (17 pages).
Ohaegbulam et al., "Human cancer immunotherapy with antibodies to the PD-1 and PD-L1 pathway," available in PMC Jan. 1, 2016, published in final edited form as: Trends Mol Med. 21(1):24-33 (Jan. 2015) (23 pages).
Shi et al., "Effect of soluble PD-L1 released by lung cancer cells in regulating the function of T lymphocytes" Chin J Oncol, Feb. 23, 2013, vol. 35, No. 2, p. 85-88 (8 pages).
First Office Action and Search Report for Chinese Patent Application No. 201910113951.2 dated Nov. 23, 2022 (24 pages).
Office Action and Search Report for Russian Patent Application No. 2019129671 dated Mar. 24, 2023 (8 pages).
Fehrenbacher et al., "Atezolizumab versus docetaxel for patients with previously treated non- small-cell lung cancer (POPLAR): a multicentre, open-label, phase 2 randomised controlled trial" Lancet. 387: 1837-46 (Mar. 2016).
Felip et al., "Adjuvant atezolizumab after adjuvant chemotherapy in resected stage IB-IIIA non-small-cell lung cancer (IMpower010): a randomised, multicentre, open-label, phase 3 trial," The Lancet. 398: 1344-1357 (Oct. 2021) (14 pages).
Rittmeyer et al., "Atezolizumab versus docetaxel in patients with previously treated non-small-cell lung cancer (OAK): a phase 3, open-label, multicentre randomised controlled trial," Lancet. 389(10066): 255-265 (Jan. 2017).
West et al., "Atezolizumab in combination with carboplatin plus nab-paclitaxel chemotherapy compared with chemotherapy alone as first-line treatment for metastatic non-squamous non-small-cell lung cancer (IMpower130): a multicentre, randomised, open-label, phase 3 trial," Lancet Oncol. 20(7):924-937 (Jul. 2019).
Zitvogel et al., "Targeting PD-1/PD-L1 interactions for cancer immunotherapy," Oncoimmunology 1(8):1223-1225 (Nov. 2012).

NSCLC, adenocarcinoma

Malignant Melanoma

Triple-Negative Breast Cancer

Only Pts with samples available before 11/1/12

Only Pts with samples available before 11/1/12

Only Pts with samples available before 11/1/12

| Paired Serial Biopsy Tumor Samples* | N = 26 |
| --- | --- |
| Max SLD decrease† | |
| >30% reduction | 4 |
| 0-30% reduction | 6 |
| 0-20% increase | 10 |
| >20% increase | 4 |
| Unevaluable SLD due to tumor excision | 2 |
| Indications | |
| Melanoma | 15 |
| RCC | 4 |
| NSCLC | 2 |
| H&N | 2 |
| Other (CRC, gastric, breast) | 1 each |

*paired tumor samples that contained tumor tissue
†at any time point in study

Figure 9

Summary of responses to anti-PD-L1 antibody in paired biopsies

| Max SLD Decrease[†] | Increase in tumor PD-L1* |
|---|---|
| >30% reduction | 4/4 (100%) |
| 0-30% reduction | 2/6 (33%) |
| 0-20% increase | 1/10 (10%) |
| >20% increase | 0/4 (0%) |
| Unevaluable SLD (due to tumor excision**) | 2/2 (100%) |

\* # of patients with increased PD-L1 expression following Tx with anti-PD-L1 antibody, including sterilized tumor with PD-L1+ immune cells; increase in tumor PD-L1 as measured by PD-L1 IHC
[†] at any time point in study
\*\* excision of responding tumor for purposes of biomarker analysis rendered the patient UE for max SLD change Figure 10
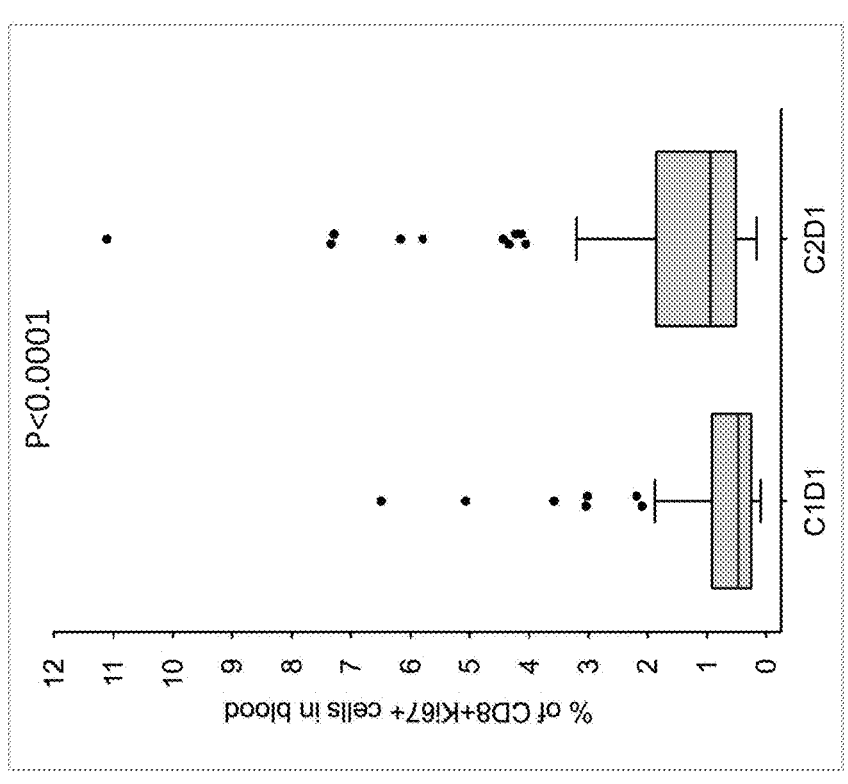

(b)

Figure 13
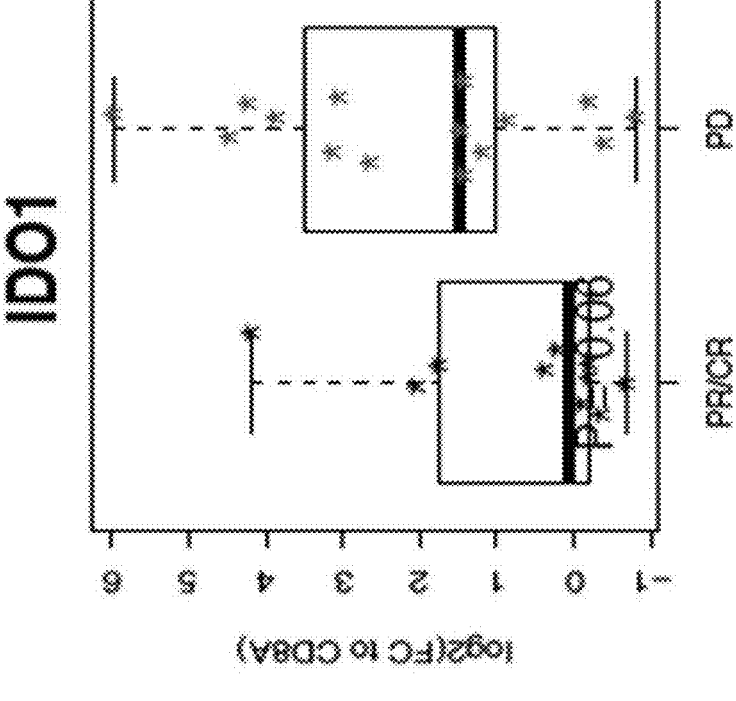
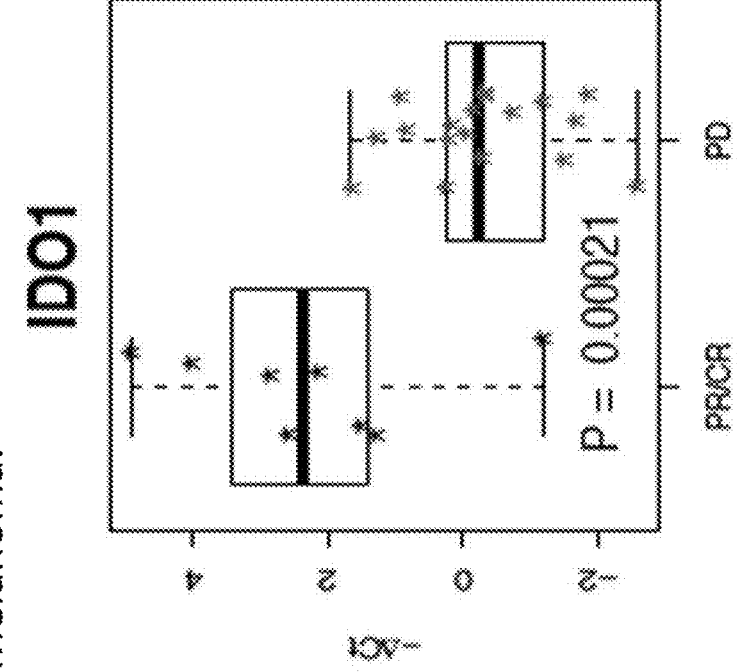

Figure 14

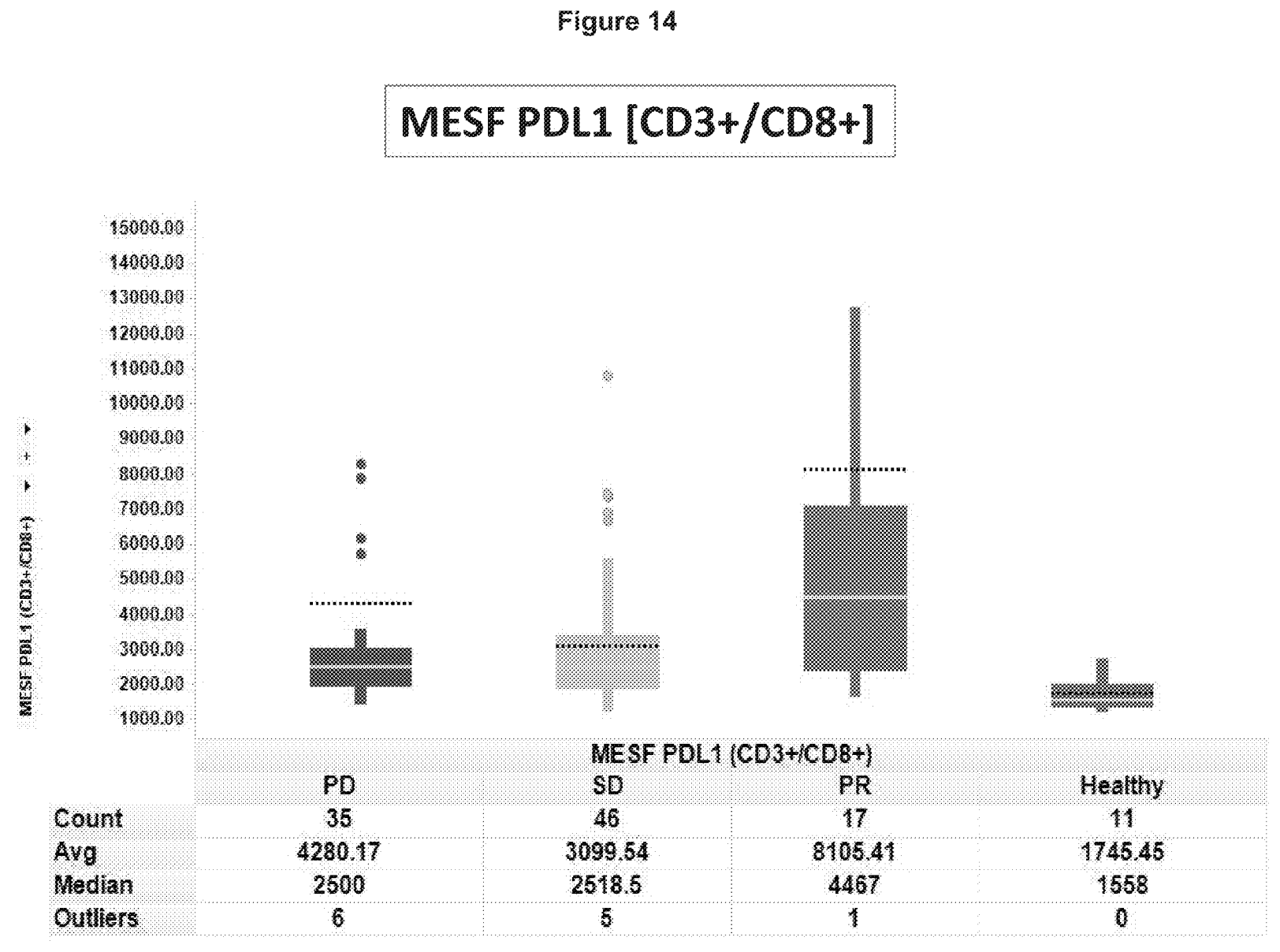

MESF PDL1 [CD3+/CD8+]

| | PD | SD | PR | Healthy |
|---|---|---|---|---|
| MESF PDL1 (CD3+/CD8+) | | | | |
| Count | 35 | 46 | 17 | 11 |
| Avg | 4280.17 | 3099.54 | 8105.41 | 1745.45 |
| Median | 2500 | 2518.5 | 4467 | 1558 |
| Outliers | 6 | 5 | 1 | 0 |

*P < 0.0001 for C2D1 vs baseline. For patients who had C1D1 data, C1D1 data were used for baseline. For patients who did not have C1D1 data, screening data were used for baseline.*

Figure 20

Summary of Responses to MPDL3280A in Paired Biopsies

| Maximum SLD Decrease[a] | Increase in Tumor Cell PD-L1[b] n/N (%) | Increase in Immune Cell PD-L1[b] n/N (%) |
|---|---|---|
| > 30% reduction | 4/6 (66%) | 5/6 (83%) |
| 0%-30% reduction | 4/9 (44%) | 2/9 (22%) |
| 0%-20% increase | 2/10 (20%) | 2/10 (20%) |
| > 20% increase | 0/4 (0%) | 1/4 (25%) |
| Unevaluable SLD (due to tumor excision[c]) | 1/1 (100%) | 1/1 (100%) |

[a] At any time point in study.
[b] Number of patients with increased PD-L1 expression in tumor or tumor infiltrating immune cells following treatment with MPDL3280A; increase in PD-L1 expression defined by increase of ≥ 5% PD-L1 + cells as measured by Genentech/Roche PD-L1 IHC.
[c] Excision of responding tumor for purposes of biomarker analysis rendered the patient unevaluable for maximum SLD change.

Figure 22
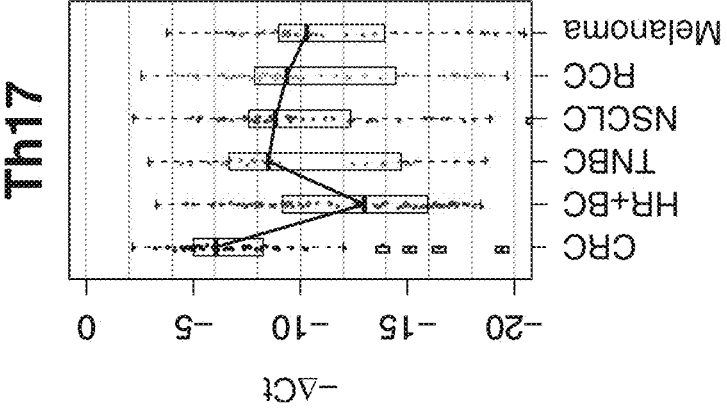
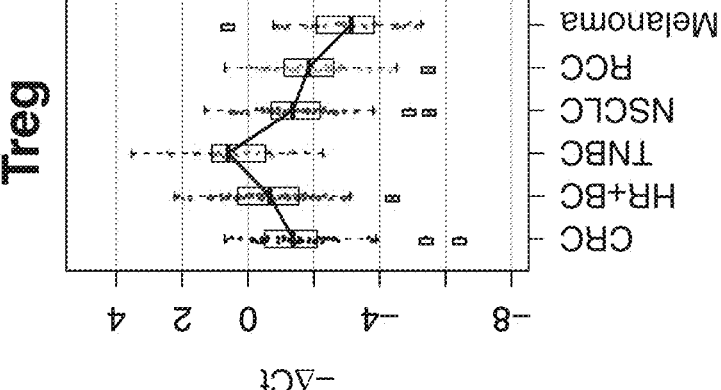
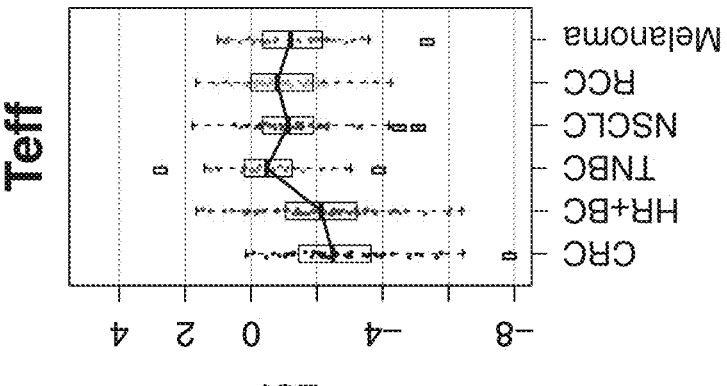

Figure 23
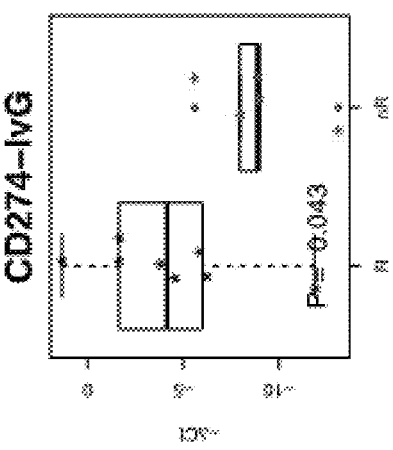
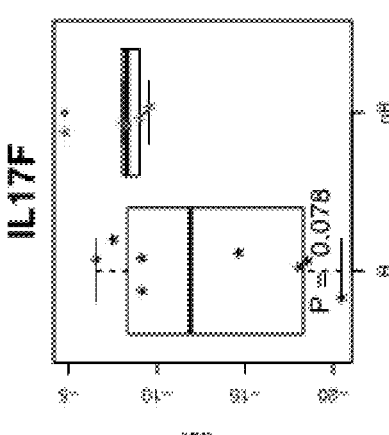
(8 Rs vs 5 nRs)

(14 Early Rs, 11 Late Rs)

Figure 25
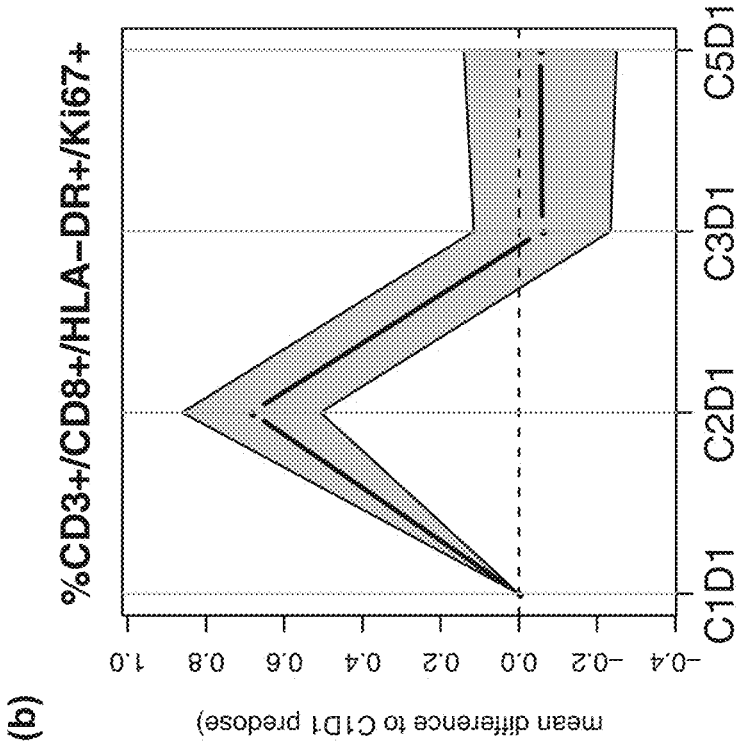
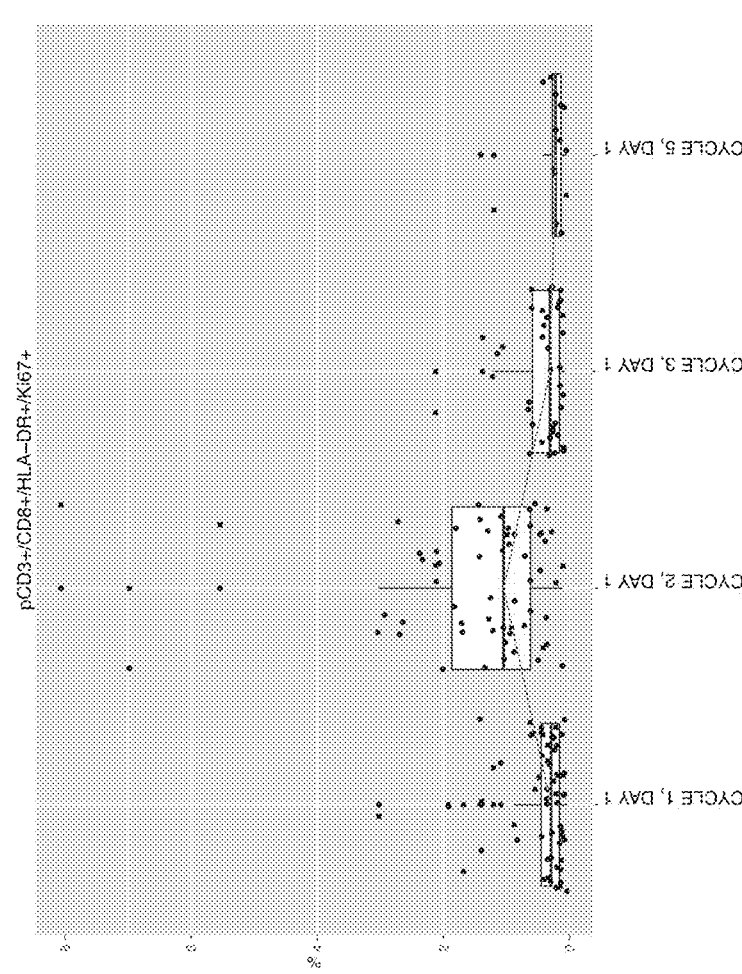

Figure 29
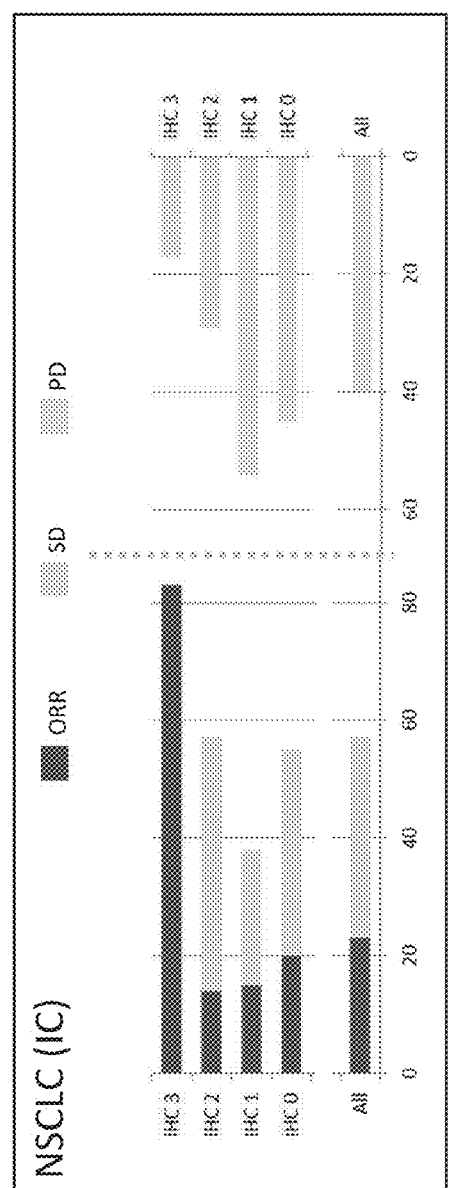
(a)
IHC, immunohistochemistry; ORR, overall response rate; PD, progressive disease; SD, stable disease.
Patient's tumor assessment not done: 0% IHC 0, 8% IHC 1, 14% IHC 2, 0% IHC 3, 0% unknown, 3% All.
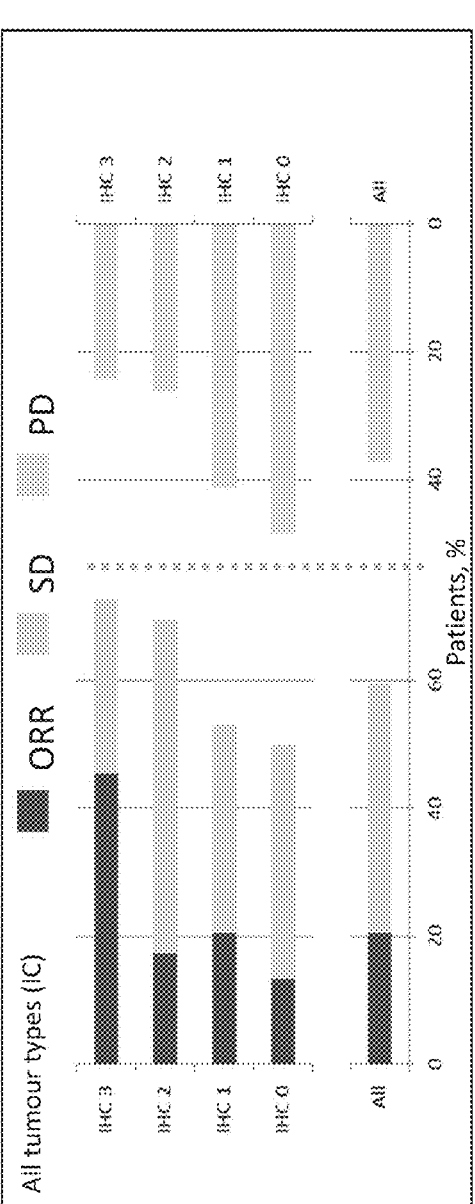
(b)
IHC, immunohistochemistry; ORR, overall response rate; PD, progressive disease; SD, stable disease.
Patient's tumor assessment not done: 1.6% IHC 0, 5.9% IHC 1, 4.3% IHC 2, 3% IHC 3, 4% unknown, 3.4% All.

BIOMARKERS AND METHODS OF TREATING PD-1 AND PD-L1 RELATED CONDITIONS

CROSS REFERENCE TO RELATED APPLICATIONS

The instant application is a divisional of U.S. patent application Ser. No. 14/850,462, filed 10 Sep. 2015, which is a continuation of PCT Application No. PCT/US2014/024746, filed 12 Mar. 2014, which claims the benefit of priority of U.S. Provisional Patent Application Nos. 61/802,296, filed 15 Mar. 2013; 61/812,678, filed 16 Apr. 2013; 61/829,236, filed 30 May 2013; and 61/883,186, filed 26 Sep. 2013, the contents of all of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Mar. 3, 2022, is named 50474-1470014_Sequence_Listing_3_3_22_ST25 and is 8,962 bytes in size.

FIELD

Provided herein are biomarkers for the treatment of pathological conditions, such as cancer, and methods of using PD-L1/PD-1 pathway antagonists. In particular, provided biomarkers for patient selection and prognosis in cancer, as well as methods of therapeutic treatment, articles of manufacture and methods for making them, diagnostic kits, methods of detection and methods of advertising related thereto.

BACKGROUND

Cancer remains to be one of the most deadly threats to human health. In the U.S., cancer affects nearly 1.3 million new patients each year, and is the second leading cause of death after heart disease, accounting for approximately 1 in 4 deaths. For example, lung cancer is the most common form of cancer and the leading cancer killer among American women. It is also predicted that cancer may surpass cardiovascular diseases as the number one cause of death within 5 years. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making timely detection and treatment extremely difficult.

Despite the significant advancement in the treatment of cancer, improved therapies are still being sought.

All references cited herein, including patent applications and publications, are incorporated by reference in their entirety.

SUMMARY

Provided herein are methods identifying an individual with a disease or disorder who is more likely to respond to treatment with a PD-L1 axis binding antagonist, the method comprising: determining the presence of a PD-L1 biomarker in a sample from the individual, wherein the presence of a PD-L1 biomarker in the sample indicates that the individual is more likely to respond to treatment with the PD-L1 axis binding antagonist, and providing a recommendation that the individual will be more likely to respond to treatment with a PD-L1 axis binding antagonist.

Provided herein are methods for predicting responsiveness of an individual with a disease or disorder to treatment with a PD-L1 axis binding antagonist, the method comprising: determining the presence of a PD-L1 biomarker in a sample from the individual, wherein the presence of a PD-L1 biomarker in the sample indicates that the individual is more likely to be responsive to treatment with the PD-L1 axis binding antagonist, and providing a recommendation that the individual will have an increased likelihood of being responsive to treatment with a PD-L1 axis binding antagonist.

Provided herein are methods for determining likelihood that an individual with a disease or disorder will exhibit benefit from treatment with a PD-L1 axis binding antagonist, the method comprising: determining the presence of a PD-L1 biomarker in a sample from the individual, wherein the presence of a PD-L1 biomarker in the sample indicates that the individual has an increased likelihood of benefit from treatment with the PD-L1 axis binding antagonist, and providing a recommendation that the individual will have an increased likelihood of benefit from treatment with a PD-L1 axis binding antagonist.

Provided herein are methods for selecting a therapy for an individual with a disease or disorder, the method comprising: determining the presence of a PD-L1 biomarker in a sample from the individual, and providing a recommendation that the therapy selected for the individual comprise treatment with a PD-L1 axis binding antagonist based on the presence of a PD-L1 biomarker in the sample.

In some embodiments, the methods further comprise administering an effective amount of the PD-L1 axis binding antagonist to the individual.

Provided herein are methods for treating a disease or disorder in an individual, the method comprising: determining the presence of a PD-L1 biomarker in a sample from the individual, and administering an effective amount of a PD-L1 axis binding antagonist to the individual.

Provided herein are methods of treating a disease or disorder in an individual comprising administering to the individual an effective amount of a PD-L1 axis binding antagonist, wherein treatment is based upon the presence of a PD-L1 biomarker in a sample from the individual.

Provided herein are methods for advertising a PD-L1 axis binding antagonist comprising promoting, to a target audience, the use of the PD-L1 axis binding antagonist for treating an individual with a disease or disorder based on the presence of a PD-L1 biomarker.

Provided herein are assays for identifying an individual with a disease or disorder to receive a PD-L1 axis binding antagonist, the method comprising: determining the presence of a PD-L1 biomarker in a sample from the individual, and recommending a PD-L1 axis binding antagonist based on the presence of a PD-L1 biomarker.

Provided herein are diagnostic kits comprising one or more reagent for determining the presence of a PD-L1 biomarker in a sample from an individual with a disease or disorder, wherein the presence of a PD-L1 biomarker means a higher likelihood of efficacy when the individual is treated with a PD-L1 axis binding antagonist, and wherein the absence of a PD-L1 biomarker means a less likelihood of efficacy when the individual with the disease is treated with the PD-L1 axis binding antagonist.

Provided herein are also articles of manufacture comprising, packaged together, a PD-L1 axis binding antagonist, in a pharmaceutically acceptable carrier and a package insert indicating that the PD-L1 axis binding antagonist is for treating a patient with a disease or disorder based on expression of a PD-L1 biomarker. Treatment methods include any of the treatment methods disclosed herein. Further provided are methods for manufacturing an article of manufacture comprising combining in a package a pharmaceutical composition comprising a PD-L1 axis binding antagonist and a package insert indicating that the pharmaceutical composition is for treating a patient with a disease or disorder based on expression of a PD-L1 biomarker.

In some embodiments of any of the methods, assays and/or kits, the PD-L1 biomarker is selected from the group consisting of PD-L1, PD-1, PD-L2 and any combinations thereof.

In some embodiments of any of the methods, assays and/or kits, the PD-L1 biomarker is an immune-related marker. In some embodiments, the immune-related marker is a T-cell related marker. In some embodiments, the T-cell related marker is selected from the group consisting of CD8A, IFN-g, EOMES, Granzyme-A, CXCL9 and any combinations thereof. In some embodiments, the immune-related marker is selected from the group consisting of CX3CL1, CD45RO, IDO1, Galectin 9, MIC-A, MIC-B, CTLA-4 and any combinations thereof.

In some embodiments of any of the methods, assays and/or kits, the disease or disorder is a proliferative disease or disorder. In some embodiments of any of the methods, assays and/or kits, the disease or disorder is an immune-related disease or disorder. In some embodiments of any of the methods, assays and/or kits, the disease or disorder is cancer. In some embodiments, the cancer is selected from the group consisting of non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, merkel cell cancer, and other hematologic malignancies.

In some embodiments of any of the methods, assays and/or kits, wherein the sample obtained from the individual is selected from the group consisting of tissue, whole blood, plasma, serum and combinations thereof. In some embodiments, the tissue sample is a tumor tissue sample. In some embodiments, the tumor tissue sample comprises tumor cells, tumor infiltrating immune cells, stromal cells and any combinations thereof. In some embodiments, the tissue sample is formalin fixed and paraffin embedded, archival, fresh or frozen. In some embodiments, the sample is whole blood. In some embodiments, the whole blood comprises immune cells, circulating tumor cells and any combinations thereof.

In some embodiments of any of the methods, assays and/or kits, the sample is obtained prior to treatment with a PD-L1 axis binding antagonist.

In some embodiments of any of the methods, assays and/or kits, the presence of a PD-L1 biomarker indicates that the individual is likely to have increased clinical benefit when the individual is treated with the PD-L1 axis binding antagonist. In some embodiments, the increased clinical benefit comprises a relative increase in one or more of the following: overall survival (OS), progression free survival (PFS), complete response (CR), partial response (PR) and combinations thereof.

In some embodiments of any of the methods, assays and/or kits, the PD-L1 biomarker is absent from the sample when it comprises 0% of the sample.

In some embodiments of any of the methods, assays and/or kits, the PD-L1 biomarker is present in the sample when it comprises more than 0% of the sample. In some embodiments, the PD-L1 biomarker is present in at least 1% of the sample. In some embodiments, the PD-L1 biomarker is present in at least 5% of the sample. In some embodiments, the PD-L1 biomarker is present in at least 10% of the sample.

In some embodiments of any of the methods, assays and/or kits, the PD-L1 biomarker is detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometery, HPLC, qPCR, RT-qPCR, multiplex qPCR or RT-qPCR, RNA-seq, microarray analysis, SAGE, MassARRAY technique, and FISH, and combinations thereof.

In some embodiments of any of the methods, assays and/or kits, the PD-L1 biomarker is detected in the sample by protein expression. In some embodiments, protein expression is determined by immunohistochemistry (IHC). In some embodiments, the PD-L1 biomarker is detected using an anti-PD-L1 antibody. In some embodiments, the PD-L1 biomarker is detected as a weak staining intensity by IHC. In some embodiments, the PD-L1 biomarker is detected as a moderate staining intensity by IHC. In some embodiments, the PD-L1 biomarker is detected as a strong staining intensity by IHC. In some embodiments, the PD-L1 biomarker is detected on tumor cells, tumor infiltrating immune cells, stromal cells and any combinations thereof. In some embodiments, the staining is membrane staining, cytoplasmic staining or combinations thereof.

In some embodiments of any of the methods, assays and/or kits, the absence of the PD-L1 biomarker is detected as absent or no staining in the sample. In some embodiments of any of the methods, assays and/or kits, the presence of the PD-L1 biomarker is detected as any staining in the sample.

In some embodiments of any of the methods, assays and/or kits, the PD-L1 biomarker is detected in the sample by nucleic acid expression. In some embodiments, the nucleic acid expression is determined using qPCR, RT-qPCR, multiplex qPCR or RT-qPCR, RNA-seq, microarray analysis, SAGE, MassARRAY technique, or FISH. In some embodiments, the PD-L1 biomarker is detected on tumor cells, tumor infiltrating immune cells, stromal cells and any combinations thereof.

In some embodiments of any of the methods, assays and/or kits, the PD-L1 axis binding antagonist is selected from the group consisting of a PD-L1 binding antagonist and a PD-1 binding antagonist.

In some embodiments of any of the methods, assays and/or kits, the PD-L1 axis binding antagonist is a PD-L1 binding antagonist. In some embodiments of any of the methods, assays and/or kits, the PD-L1 binding antagonist inhibits the binding of PD-L1 to its ligand binding partners. In some embodiments of any of the methods, assays and/or kits, the PD-L1 binding antagonist inhibits the binding of PD-L1 to PD-1. In some embodiments of any of the methods, assays and/or kits, the PD-L1 binding antagonist inhibits the binding of PD-L1 to B7-1. In some embodiments of any of the methods, assays and/or kits, the PD-L1 binding antagonist inhibits the binding of PD-L1 to both PD-1 and B7-1.

In some embodiments of any of the methods, assays and/or kits, the PD-L1 binding antagonist is an antibody. In some embodiments of any of the methods, assays and/or kits, the antibody is a monoclonal antibody. In some embodiments of any of the methods, assays and/or kits, the antibody is a human, humanized or chimeric antibody.

In some embodiments of any of the methods, assays and/or kits, the PD-L1 axis binding antagonist is a PD-1 binding antagonist. In some embodiments of any of the methods, assays and/or kits, the PD-1 binding antagonist inhibits the binding of PD-1 to its ligand binding partners. In some embodiments of any of the methods, assays and/or kits, the PD-1 binding antagonist inhibits the binding of PD-1 to PD-L1. In some embodiments of any of the methods, assays and/or kits, the PD-1 binding antagonist inhibits the binding of PD-1 to PD-L2. In some embodiments of any of the methods, assays and/or kits, the PD-1 binding antagonist inhibits the binding of PD-1 to both PD-L1 and PD-L2.

In some embodiments of any of the methods, assays and/or kits, the PD-1 binding antagonist is an antibody. In some embodiments of any of the methods, assays and/or kits, the antibody is a monoclonal antibody. In some embodiments of any of the methods, assays and/or kits, the antibody is a human, humanized or chimeric antibody.

In some embodiments of any of the methods, assays and/or kits, further comprising an effective amount of a second therapeutic selected from the group consisting of cytotoxic agent, a chemotherapeutic agent, a growth inhibitory agent, a radiation therapy agent, and anti-angiogenic agent, and combinations thereof.

Provided herein are methods for assessing a treatment response of an individual with a PD-L1 axis binding antagonist, the method comprising: (a) determining the level(s) of one or more biomarkers in a biological sample derived from the individual at a time point during or after administration of the PD-L1 axis binding antagonist; and (b) maintaining, adjusting, or stopping the treatment of the individual based on a comparison of the level(s) of one or more biomarkers in the biological sample with reference levels, wherein a change in the level(s) of one or more biomarkers in the biological sample compared to the reference levels is indicative of a response to treatment with the PD-L1 axis binding antagonist.

Provided herein are methods for monitoring the response of an individual treated with a PD-L1 axis binding antagonist, said method comprising: (a) determining the level(s) of one or more biomarkers in a biological sample derived from the individual at a time point during or after administration of the PD-L1 axis binding antagonist; and (b) comparing the level(s) of one or more biomarkers in the biological sample with reference levels in order to monitor the response in the individuals undergoing treatment with the PD-L1 axis binding antagonist.

In some embodiments, the reference levels of the one or more biomarkers is selected from the group consisting of (1) the level of the one or more biomarkers from the individual prior to administration of the PD-L1 axis binding antagonist; (2) the level of the one or more biomarkers from a reference population; (3) a pre-assigned level for the one or more biomarkers; and (4) the level of the one or more biomarkers from the individual at a second time point prior to the first time point.

In some embodiments, the change in the level(s) of one or more biomarkers in the biological sample compared to the reference levels is an increase in the levels.

In some embodiments, the change in the level(s) of one or more biomarkers in the biological sample compared to the reference levels is a decrease in the levels.

In some embodiments, the one or more biomarkers is selected from the group consisting of PD-L1, PD-1, PD-L2 and any combinations thereof.

In some embodiments, the one or more biomarkers selected from the group consisting of PD-L1, PD-1, PD-L2 and any combinations thereof is increased in the biological sample compared to the reference levels. In some embodiments, an increase in one or more biomarkers selected from the group consisting of PD-L1, PD-1, PD-L2 and any combinations thereof in the biological sample compared to the reference levels is indicative of a positive response to treatment.

In some embodiments, the one or more biomarkers is an immune related marker. In some embodiments, the one or more biomarkers is a T-cell related marker.

In some embodiments, the one or more biomarkers is a T-cell activation marker.

In some embodiments, the T-cell activation marker is increased in the biological sample compared to the reference levels.

In some embodiments, the T-cell activation marker is selected from the group consisting of an CD8, IFN-g, Granzyme-A, TNF-a, perforin and any combinations thereof. In some embodiments, an increase in the T-cell activation marker selected from the group consisting of CD8, IFN-g, Granzyme-A, TNF-a, perforin and any combinations thereof in the biological sample compared to the reference levels is indicative of a positive response to treatment.

In some embodiments, the one or more biomarkers is an activated proliferating T cell.

In some embodiments, the activated proliferating T cell is increased in the biological sample compared to the reference levels.

In some embodiments, the activated proliferating T cell is a CD8+/Ki67+ cell, CD8+/HLA-DR+/Ki67+ cell and any combinations thereof.

In some embodiments, the one or more biomarkers is IL-6. In some embodiments, the IL-6 level is decreased in the biological sample compared to the reference levels. In some embodiments, a decrease in the IL-6 level in the biological sample compared to the reference levels is indicative of a positive response to treatment. In some embodiments, the IL-6 level is increased in the biological sample compared to the reference levels. In some embodiments, an increase in the IL-6 level in the biological sample compared to the reference levels is indicative of a negative response to treatment.

In some embodiments, the biological sample derived from the individual is selected from the group consisting of a cell, a tissue, a tissue culture, a tumor, a biological fluid and combinations thereof.

In some embodiments, the biological fluid is selected from the group consisting of plasma, serum, whole blood, PBMCs and combinations thereof.

In some embodiments, the tissue is a tumor tissue. In some embodiments, the tumor tissue is selected from the group consisting of tumor cells, tumor infiltrating cells, stromal cells and any combinations thereof.

In some embodiments, the cell is a circulating tumor cell (CTC).

In some embodiments, the individual suffers from a proliferative disease or disorder.

In some embodiments, the individual suffers from cancer or malignancy. In some embodiments, the cancer or malignancy is selected from non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, merkel cell cancer, and other hematologic malignancies.

In some embodiments, the individual suffers from an immune-related disease or disorder.

In some embodiments, the PD-L1 axis binding antagonist is a PD-L1 binding antagonist.

In some embodiments, the PD-L1 binding antagonist inhibits the binding of PD-L1 to its ligand binding partners.

In some embodiments, the PD-L1 binding antagonist inhibits the binding of PD-L1 to PD-1. In some embodiments, the PD-L1 binding antagonist inhibits the binding of PD-L1 to B7-1. In some embodiments, the PD-L1 binding antagonist inhibits the binding of PD-L1 to both PD-1 and B7-1.

In some embodiments, the PD-L1 binding antagonist is an antibody. In some embodiments, the antibody is a monoclonal antibody. In some embodiments, the antibody is a human, humanized or chimeric antibody.

In some embodiments, the PD-L1 axis binding antagonist is a PD-1 binding antagonist.

In some embodiments, the PD-1 binding antagonist inhibits the binding of PD-1 to its ligand binding partners.

In some embodiments, the PD-1 binding antagonist inhibits the binding of PD-1 to PD-L1. In some embodiments, the PD-1 binding antagonist inhibits the binding of PD-1 to PD-L2. In some embodiments, the PD-1 binding antagonist inhibits the binding of PD-1 to both PD-L1 and PD-L2.

In some embodiments, the PD-1 binding antagonist is an antibody. In some embodiments, the antibody is a monoclonal antibody. In some embodiments, the antibody is a human, humanized or chimeric antibody.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 9 summarizes changes in PD-L1 expression in patients undergoing anti-PD-L1 antibody treatment.

FIG. 13 shows the correlation of IDO1 gene expressions in tumor samples from either melanoma or NSCLC with either PD or PR/CR response to anti-PD-L1 treatment in cancer patients. PD=progressive disease; PR=partial response; CR=complete response.

FIG. 14 shows an increase in PD-L1 expression on circulating T cells in blood collected from patients responding to treatment with anti-PD-L1 antibody. PD=progressive disease; PR=partial response; CR=complete response.

FIG. 20 shows the adaptive increase in PD-L1 expression is prominent in patients responding to treatment with anti-PD-L1 antibody.

FIG. 22 shows the correlation of gene signatures associated with Teff (T-effector) cells, Treg (T-regulatory) cells, and Th17 cells across six cancer indications.

FIG. 23 shows a trend toward higher tumor gene expression of IL17F in patients who do not respond to anti-PD-L1 treatment. R=Responders; nR=Non-responders.

FIG. 25 shows transient increase in circulating CD8+/HLA-DR+/Ki67+ cells in patients undergoing treatment with anti-PD-L1 antibody. (a) in UBC patients, (b) in all patients.

FIG. 29 shows the association between of PD-L1 expression in tumor infiltrating immune cells (IC) and response to anti-PD-L1 treatment. (a) in NSCLC, (b) in all tumors.

DETAILED DESCRIPTION

Definitions

Figure 1:
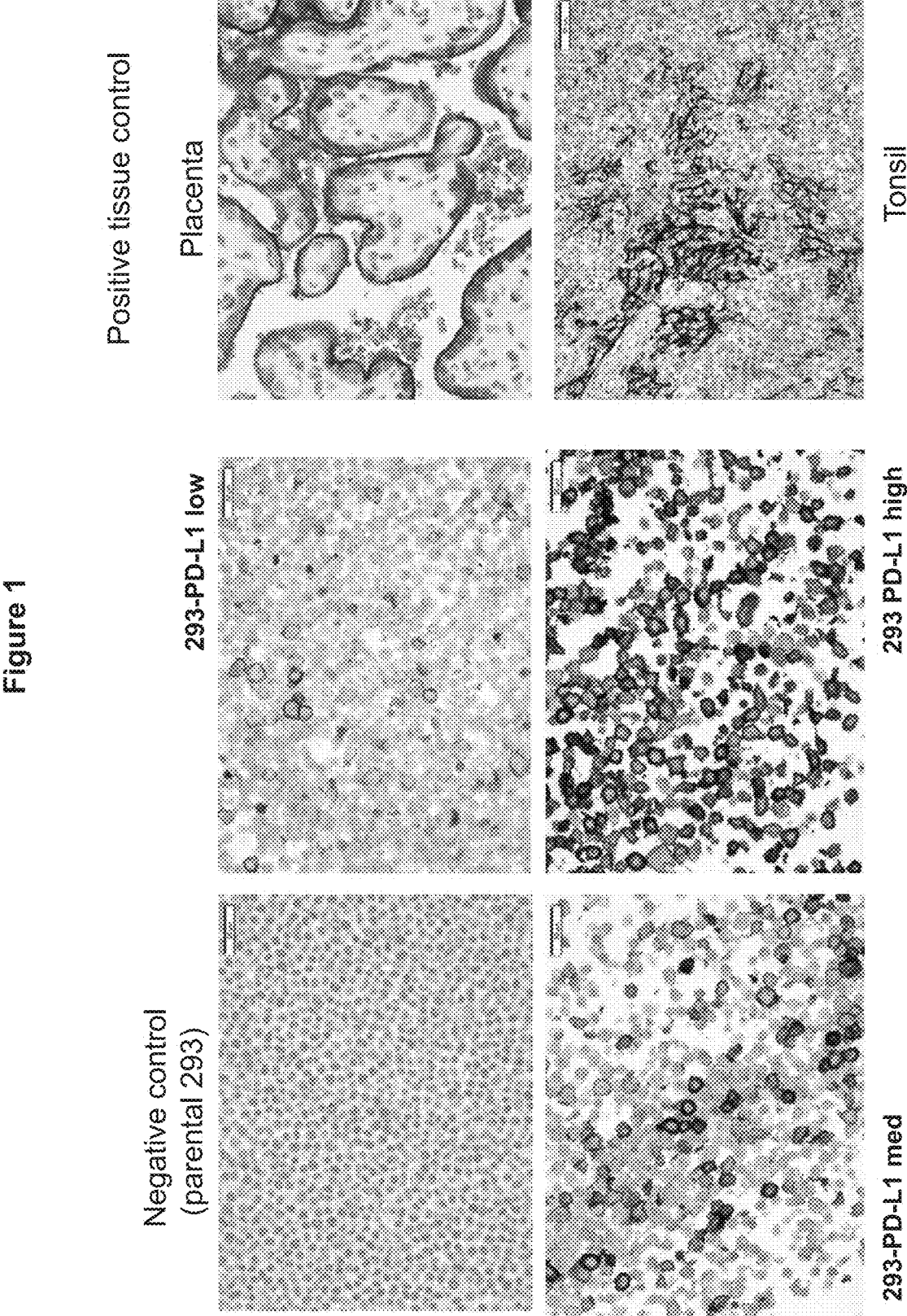
FIG. 1 shows exemplary IHC analysis of control cell samples. (A) Negative control IHC staining of parental HEK-293 cells; (B) IHC staining of HEK-293 cells transfected with recombinant human PD-L1 with weak staining intensity; (C) IHC staining of HEK-293 cells transfected with recombinant human PD-L1 with moderate staining intensity; (D) IHC staining of HEK-293 cells transfected with recombinant human PD-L1 with strong staining intensity; (E) Positive tissue control IHC staining of placental tissue sample; (F) Positive tissue control IHC staining of tonsil tissue sample. All IHC staining were performed using a proprietary anti-PD-L1 antibody.

The term "PD-L1 axis binding antagonist" is a molecule that inhibits the interaction of a PD-L1 axis binding partner with either one or more of its binding partner, so as to remove T-cell dysfunction resulting from signaling on the PD-1 signaling axis—with a result being to restore or enhance T-cell function. As used herein, a PD-L1 axis binding antagonist includes a PD-L1 binding antagonist and a PD-1 binding antagonist as well as molecules that interfere with the interaction between PD-L1 and PD-1 (e.g., PD-L2-Fc fusion).

The term "PD-L1 binding antagonists" is a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative signal mediated by or through cell surface proteins expressed on T lymphocytes, and other cells, mediated signaling through PD-L1 or PD-1 so as render a dysfunctional T-cell less non-dysfunctional.

The term "PD-1 binding antagonists" is a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative signal mediated by or through cell surface proteins expressed on T lymphocytes, and other cells, mediated signaling through PD-1 or PD-L1 so as render a dysfunctional T-cell less non-dysfunctional.

The terms "Programmed Death Ligand 1" and "PD-L1" refer herein to a native sequence PD-L1 polypeptide, polypeptide variants and fragments of a native sequence polypeptide and polypeptide variants (which are further defined herein). The PD-L1 polypeptide described herein may be that which is isolated from a variety of sources, such as from human tissue types or from another source, or prepared by recombinant or synthetic methods.

A "native sequence PD-L1 polypeptide" comprises a polypeptide having the same amino acid sequence as the corresponding PD-L1 polypeptide derived from nature.

"PD-L1 polypeptide variant", or variations thereof, means a PD-L1 polypeptide, generally an active PD-L1 polypeptide, as defined herein having at least about 80% amino acid sequence identity with any of the native sequence PD-L1 polypeptide sequences as disclosed herein. Such PD-L1 polypeptide variants include, for instance, PD-L1 polypeptides wherein one or more amino acid residues are added, or deleted, at the N- or C-terminus of a native amino acid sequence. Ordinarily, a PD-L1 polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a native sequence PD-L1 polypeptide sequence as disclosed herein. Ordinarily, PD-L1 variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 281, 282, 283, 284, 285, 286, 287, 288, 289 amino acids in length, or more. Optionally, PD-L1 variant polypeptides will have no more than one conservative amino acid substitution as compared to a native PD-L1 polypeptide sequence, alternatively no more than 2, 3, 4, 5, 6, 7, 8, 9, or 10 conservative amino acid substitution as compared to the native PD-L1 polypeptide sequence.

The term "PD-L1 antagonist" as defined herein is any molecule that partially or fully blocks, inhibits, or neutralizes a biological activity and/or function mediated by a native sequence PD-L1. In certain embodiments such antagonist binds to PD-L1. According to one embodiment, the antagonist is a polypeptide. According to another embodiment, the antagonist is an anti-PD-L1 antibody. According to another embodiment, the antagonist is a small molecule antagonist. According to another embodiment, the antagonist is a polynucleotide antagonist.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azidoribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, single stranded, polynucleotides that are, but not necessarily, less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "primer" refers to a single stranded polynucleotide that is capable of hybridizing to a nucleic acid and following polymerization of a complementary nucleic acid, generally by providing a free 3'-OH group.

The term "small molecule" refers to any molecule with a molecular weight of about 2000 daltons or less, preferably of about 500 daltons or less.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The terms "anti-PD-L1 antibody" and "an antibody that binds to PD-L1" refer to an antibody that is capable of binding PD-L1 with sufficient affinity such that the antibody is useful as a diagnostic and/or therapeutic agent in targeting PD-L1. In one embodiment, the extent of binding of an anti-PD-L1 antibody to an unrelated, non-PD-L1 protein is less than about 10% of the binding of the antibody to PD-L1 as measured, e.g., by a radioimmunoassay (RIA). In certain embodiments, an anti-PD-L1 antibody binds to an epitope of PD-L1 that is conserved among PD-L1 from different species.

A "blocking" antibody or an "antagonist" antibody is one which inhibits or reduces biological activity of the antigen it binds. Preferred blocking antibodies or antagonist antibodies substantially or completely inhibit the biological activity of the antigen.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called $\alpha$, $\delta$, $\epsilon$, $\gamma$, and $\mu$, respectively.

The terms "full length antibody," "intact antibody," and "whole antibody" are used herein interchangeably to refer to an antibody having a structure substantially similar to a native antibody structure or having heavy chains that contain an Fc region as defined herein.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "immunoconjugate" is an antibody conjugated to one or more heterologous molecule(s), including but not limited to a cytotoxic agent.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "detection" includes any means of detecting, including direct and indirect detection.

The term "biomarker" as used herein refers to an indicator, e.g., predictive, diagnostic, and/or prognostic, which can be detected in a sample. The biomarker may serve as an indicator of a particular subtype of a disease or disorder (e.g., cancer) characterized by certain, molecular, pathological, histological, and/or clinical features. In some embodiments, a biomarker is a gene. Biomarkers include, but are not limited to, polynucleotides (e.g., DNA, and/or RNA), polynucleotide copy number alterations (e.g., DNA copy numbers), polypeptides, polypeptide and polynucleotide modifications (e.g. posttranslational modifications), carbohydrates, and/or glycolipid-based molecular markers.

The terms "biomarker signature," "signature," "biomarker expression signature," or "expression signature" are used interchangeably herein and refer to one or a combination of biomarkers whose expression is an indicator, e.g., predictive, diagnostic, and/or prognostic. The biomarker signature may serve as an indicator of a particular subtype of a disease or disorder (e.g., cancer) characterized by certain molecular, pathological, histological, and/or clinical features. In some embodiments, the biomarker signature is a "gene signature." The term "gene signature" is used interchangeably with "gene expression signature" and refers to one or a combination of polynucleotides whose expression is an indicator, e.g., predictive, diagnostic, and/or prognostic. In some embodiments, the biomarker signature is a "protein signature." The term "protein signature" is used interchangeably with "protein expression signature" and refers to one or a combination of polypeptides whose expression is an indicator, e.g., predictive, diagnostic, and/or prognostic.

The "amount" or "level" of a biomarker associated with an increased clinical benefit to an individual is a detectable level in a biological sample. These can be measured by methods known to one skilled in the art and also disclosed herein. The expression level or amount of biomarker assessed can be used to determine the response to the treatment.

The terms "level of expression" or "expression level" in general are used interchangeably and generally refer to the amount of a biomarker in a biological sample. "Expression" generally refers to the process by which information (e.g., gene-encoded and/or epigenetic) is converted into the structures present and operating in the cell. Therefore, as used herein, "expression" may refer to transcription into a polynucleotide, translation into a polypeptide, or even polynucleotide and/or polypeptide modifications (e.g., posttranslational modification of a polypeptide). Fragments of the transcribed polynucleotide, the translated polypeptide, or polynucleotide and/or polypeptide modifications (e.g., post-translational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs).

"Elevated expression," "elevated expression levels," or "elevated levels" refers to an increased expression or increased levels of a biomarker in an individual relative to a control, such as an individual or individuals who are not suffering from the disease or disorder (e.g., cancer) or an internal control (e.g., housekeeping biomarker).

"Reduced expression," "reduced expression levels," or "reduced levels" refers to a decrease expression or decreased levels of a biomarker in an individual relative to a control, such as an individual or individuals who are not suffering from the disease or disorder (e.g., cancer) or an internal control (e.g., housekeeping biomarker). In some embodiments, reduced expression is little or no expression.

The term "housekeeping biomarker" refers to a biomarker or group of biomarkers (e.g., polynucleotides and/or polypeptides) which are typically similarly present in all cell types. In some embodiments, the housekeeping biomarker is a "housekeeping gene." A "housekeeping gene" refers herein to a gene or group of genes which encode proteins whose activities are essential for the maintenance of cell function and which are typically similarly present in all cell types.

"Amplification," as used herein generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The term "multiplex-PCR" refers to a single PCR reaction carried out on nucleic acid obtained from a single source (e.g., an individual) using more than one primer set for the purpose of amplifying two or more DNA sequences in a single reaction.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, can be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" can be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The technique of "polymerase chain reaction" or "PCR" as used herein generally refers to a procedure wherein minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51: 263 (1987); Erlich, ed., PCR Technology, (Stockton Press, N Y, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

"Quantitative real time polymerase chain reaction" or "qRT-PCR" refers to a form of PCR wherein the amount of PCR product is measured at each step in a PCR reaction. This technique has been described in various publications including Cronin et al., *Am. J. Pathol.* 164(1):35-42 (2004); and Ma et al., *Cancer Cell* 5:607-616 (2004).

The term "microarray" refers to an ordered arrangement of hybridizable array elements, preferably polynucleotide probes, on a substrate.

The term "polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The term "diagnosis" is used herein to refer to the identification or classification of a molecular or pathological state, disease or condition (e.g., cancer). For example, "diagnosis" may refer to identification of a particular type of cancer. "Diagnosis" may also refer to the classification of a particular subtype of cancer, e.g., by histopathological criteria, or by molecular features (e.g., a subtype characterized by expression of one or a combination of biomarkers (e.g., particular genes or proteins encoded by said genes)).

The term "aiding diagnosis" is used herein to refer to methods that assist in making a clinical determination regarding the presence, or nature, of a particular type of symptom or condition of a disease or disorder (e.g., cancer). For example, a method of aiding diagnosis of a disease or condition (e.g., cancer) can comprise measuring certain biomarkers in a biological sample from an individual.

The term "sample," as used herein, refers to a composition that is obtained or derived from a subject and/or individual of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. Samples include, but are not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebrospinal fluid, saliva, sputum, tears, perspiration, mucus, tumor lysates, and tissue culture medium, tissue extracts such as homogenized tissue, tumor tissue, cellular extracts, and combinations thereof.

By "tissue sample" or "cell sample" is meant a collection of similar cells obtained from a tissue of a subject or individual. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

A "reference sample", "reference cell", "reference tissue", "control sample", "control cell", or "control tissue", as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis, provided that it is understood that the same section of tissue sample may be analyzed at both morphological and molecular levels, or analyzed with respect to both polypeptides and polynucleotides.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

"Individual response" or "response" can be assessed using any endPoint indicating a benefit to the individual, including, without limitation, (1) inhibition, to some extent, of disease progression (e.g., cancer progression), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e. reduction, slowing down or complete stopping) of metatasis; (5) relief, to some extent, of one or more symptoms associated with the disease or disorder (e.g., cancer); (6) increase or extend in the length of survival, including overall survival and progression free survival; and/or (9) decreased mortality at a given Point of time following treatment.

An "effective response" of a patient or a patient's "responsiveness" to treatment with a medicament and similar wording refers to the clinical or therapeutic benefit imparted to a patient at risk for, or suffering from, a disease or disorder, such as cancer. In one embodiment, such benefit includes any one or more of: extending survival (including overall survival and progression free survival); resulting in an objective response (including a complete response or a partial response); or improving signs or symptoms of cancer. In one embodiment, the biomarker (e.g., PD-L1 expression, for example, as determined using IHC) is used to identify the patient who is predicted to have an increase likelihood of being responsive to treatment with a medicament (e.g., anti-PD-L1 antibody), relative to a patient who does not express the biomarker. In one embodiment, the biomarker (e.g., PD-L1 expression, for example, as determined using IHC) is used to identify the patient who is predicted to have an increase likelihood of being responsive to treatment with a medicament (e.g., anti-PD-L1 antibody), relative to a patient who does not express the biomarker at the same level. In one embodiment, the presence of the biomarker is used to identify a patient who is more likely to respond to treatment with a medicament, relative to a patient that does not have the presence of the biomarker. In another embodiment, the presence of the biomarker is used to determine that a patient will have an increase likelihood of benefit from treatment with a medicament, relative to a patient that does not have the presence of the biomarker.

Survival" refers to the patient remaining alive, and includes overall survival as well as progression free survival.

Overall survival refers to the patient remaining alive for a defined period of time, such as 1 year, 5 years, etc from the time of diagnosis or treatment.

Progression free survival refers to the patient remaining alive, without the cancer progressing or getting worse.

By "extending survival" is meant increasing overall or progression free survival in a treated patient relative to an untreated patient (i.e. relative to a patient not treated with the medicament), or relative to a patient who does not express a biomarker at the designated level, and/or relative to a patient treated with an approved anti-tumor agent. An objective response refers to a measurable response, including complete response (CR) or partial response (PR).

By complete response or "CR" is intended the disappearance of all signs of cancer in response to treatment. This does not always mean the cancer has been cured.

Partial response or "PR" refers to a decrease in the size of one or more tumors or lesions, or in the extent of cancer in the body, in response to treatment.

The term "substantially the same," as used herein, denotes a sufficiently high degree of similarity between two numeric values, such that one of skill in the art would consider the difference between the two values to be of little or no biological and/or statistical significance within the context of the biological characteristic measured by said values (e.g., Kd values or expression). The difference between said two values is, for example, less than about 50%, less than about 40%, less than about 30%, less than about 20%, and/or less than about 10% as a function of the reference/comparator value.

The phrase "substantially different," as used herein, denotes a sufficiently high degree of difference between two numeric values such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The word "label" when used herein refers to a detectable compound or composition. The label is typically conjugated or fused directly or indirectly to a reagent, such as a polynucleotide probe or an antibody, and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which results in a detectable product.

An "effective amount" of an agent refers to an amount effective, at dosages and for periods of time necessary, to achieve the desired therapeutic or prophylactic result.

A "therapeutically effective amount" refers to an amount of a therapeutic agent to treat or prevent a disease or disorder in a mammal. In the case of cancers, the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "cancer" and "cancerous" refer to or describe the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, I, or II cancer. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, merkel cell cancer, mycoses fungoids, testicular cancer, esophageal cancer, tumors of the biliary tract, as well as head and neck cancer and hematological malignancies. In some embodiments, the cancer is triple-negative metastatic breast cancer, including any histologically confirmed triple-negative (ER−, PR−, HER2−) adenocarcinoma of the breast with locally recurrent or metastatic disease (where the locally recurrent disease is not amenable to resection with curative intent).

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject, A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies are used to delay development of a disease or to slow the progression of a disease.

The term "anti-cancer therapy" refers to a therapy useful in treating cancer. Examples of anti-cancer therapeutic agents include, but are limited to, e.g., chemotherapeutic agents, growth inhibitory agents, cytotoxic agents, agents used in radiation therapy, anti-angiogenesis agents, apoptotic agents, anti-tubulin agents, and other agents to treat cancer, anti-CD20 antibodies, platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets PDGFR-beta, BlyS, APRIL, BCMA receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" refers to a chemical compound useful in the treatment of cancer. Examples of chemotherapeutic agents include alkylating agents such as thiotepa and cyclophosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e. g., calicheamicin, especially calicheamicin gamma1I and calicheamicin omega1 (see, e.g., Nicolaou et al., *Angew. Chem Intl. Ed. Engl.,* 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyano-morpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMI-DEX®), letrozole (FEMARA®) and aminoglutethimide, and other aromatase inhibitors include vorozole (RIVI-SOR®), megestrol acetate (MEGASE®), fadrozole, and 4(5)-imidazoles; lutenizing hormone-releaseing hormone agonists, including leuprolide (LUPRON® and ELI-GARD®), goserelin, buserelin, and tripterelin; sex steroids, including progestines such as megestrol acetate and medroxyprogesterone acetate, estrogens such as diethylstil-bestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery,* Borchardt et al., (ed.), pp. 247-267, Humana Press (1985). The prodrugs of this invention include, but are not limited to, phosphate-containing prodrugs, thiophos-phate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "growth inhibitory agent" when used herein refers to a compound or composition which inhibits growth of a cell (e.g., a cell whose growth is dependent upon PD-L1 expression either in vitro or in vivo). Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The *Molecular Basis of Cancer,* Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent (s).

By "reduce or inhibit" is meant the ability to cause an overall decrease of 20%, 30%, 40%, 50%, 60%, 70%, 75%, 80%, 85%, 90%, 95%, or greater. Reduce or inhibit can refer to the symptoms of the disorder being treated, the presence or size of metastases, or the size of the primary tumor.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (e.g., a package or container) or kit comprising at least one reagent, e.g., a medicament for treatment of a disease or disorder (e.g., cancer), or a probe for specifically detecting a biomarker described herein. In certain embodiments, the manufacture or kit is promoted, distributed, or sold as a unit for performing the methods described herein.

A "target audience" is a group of people or an institution to whom or to which a particular medicament is being promoted or intended to be promoted, as by marketing or advertising, especially for particular uses, treatments, or indications, such as individuals, populations, readers of newspapers, medical literature, and magazines, television or internet viewers, radio or internet listeners, physicians, drug companies, etc.

The phrase "based on" when used herein means that the information about one or more biomarkers is used to inform a treatment decision, information provided on a package insert, or marketing/promotional guidance, etc.

As is understood by one skilled in the art, reference to "about" a value or parameter herein includes (and describes) embodiments that are directed to that value or parameter per se. For example, description referring to "about X" includes description of "X".

It is understood that aspect and embodiments described herein include "consisting" and/or "consisting essentially of" aspects and embodiments. As used herein, the singular form "a", "an", and "the" includes plural references unless indicated otherwise.

I. Methods and Uses

Provided herein are methods utilizing PD-L1 biomarkers. In particular, methods utilizing a PD-L1 axis binding antagonist and a PD-L1 biomarker are provided.

Diagnostic Methods

Provided herein are methods for identifying an individual with a disease or disorder who is more likely to respond to treatment with a PD-L1 axis binding antagonist, the method comprising: determining the presence of a PD-L1 biomarker in a sample from the individual, wherein the presence of a PD-L1 biomarker in the sample indicates that the individual is more likely to respond to treatment with the PD-L1 axis binding antagonist, and providing a recommendation that the individual will be more likely to respond to treatment with a PD-L1 axis binding antagonist.

Further provided herein methods for predicting responsiveness of an individual with a disease or disorder to treatment with a PD-L1 axis binding antagonist, the method comprising: determining the presence of a PD-L1 biomarker in a sample from the individual, wherein the presence of a PD-L1 biomarker in the sample indicates that the individual is more likely to be responsive to treatment with the PD-L1 axis binding antagonist, and providing a recommendation that the individual will have an increased likelihood of being responsive to treatment with a PD-L1 axis binding antagonist.

Further provided herein are methods for determining likelihood that an individual with a disease or disorder will exhibit benefit from treatment with a PD-L1 axis binding antagonist, the method comprising: determining the presence of a PD-L1 biomarker in a sample from the individual, wherein the presence of a PD-L1 biomarker in the sample indicates that the individual has an increased likelihood of benefit from treatment with the PD-L1 axis binding antagonist, and providing a recommendation that the individual will have an increased likelihood of benefit from treatment with a PD-L1 axis binding antagonist.

Further provided are methods for selecting a therapy for an individual with a disease or disorder, the method comprising: determining the presence of a PD-L1 biomarker in a sample from the individual, and providing a recommendation that the therapy selected for the individual comprise treatment with a PD-L1 axis binding antagonist based on the presence of a PD-L1 biomarker in the sample.

In some embodiments, the methods further comprise administering an effective amount of the PD-L1 axis binding antagonist to the individual.

In some embodiments, the PD-L1 biomarker is selected from the group consisting of PD-L1, PD-1, PD-L2 and any combinations thereof.

In some embodiments, the PD-L1 biomarker is an immune-related marker. An immune-related marker refers to a marker that is expressed by immune cells, or by other cells (e.g. tumor cells, endothelial cells, fibroblasts or other stromal cells). If expressed by other than immune cells, the marker may be involved in regulation of immune cell biology and function, such as activation, priming, antigen recognition and presentation, cytokine and chemokine production, proliferation, migration, survival, antibody production and other. In some embodiments, the immune-related marker is a T-cell related marker. In some embodiments, the T-cell related marker is selected from the group consisting of CD8A, IFN-g, EOMES, Granzyme-A, CXCL9 and any combinations thereof. In some embodiments, the immune-related marker is selected from the group consisting of CX3CL1, CD45RO, IDOL Galectin 9, MIC-A, MIC-B, CTLA-4 and any combinations thereof.

In some embodiments, the presence of a PD-L1 biomarker indicates that the individual is likely to have increased clinical benefit when the individual is treated with the PD-L1 axis binding antagonist. In some embodiments, the increased clinical benefit comprises a relative increase in one or more of the following: overall survival (OS), progression free survival (PFS), complete response (CR), partial response (PR) and combinations thereof.

In some embodiments, the PD-L1 biomarker is absent from the sample when it comprises 0% of the sample. In some embodiments, the PD-L1 biomarker is present in the sample when it comprises more than 0% of the sample. In some embodiments, the PD-L1 biomarker is present in at least 1% of the sample. In some embodiments, the PD-L1 biomarker is present in at least 5% of the sample. In some embodiments, the PD-L1 biomarker is present in at least 10% of the sample.

In some embodiments, the PD-L1 biomarker is detected in the sample using a method selected from the group consisting of FACS, Western blot, ELISA, immunoprecipitation, immunohistochemistry, immunofluorescence, radio-immunoassay, dot blotting, immunodetection methods, HPLC, surface plasmon resonance, optical spectroscopy, mass spectrometery, HPLC, qPCR, RT-qPCR, multiplex qPCR or RT-qPCR, RNA-seq, microarray analysis, SAGE, MassARRAY technique, and FISH, and combinations thereof. In some embodiments, the PD-L1 biomarker is detected in the sample by protein expression. In some embodiments, protein expression is determined by immunohistochemistry (IHC). In some embodiments, PD-L1 biomarker is detected using an anti-PD-L1 antibody.

In some embodiments, the PD-L1 biomarker is detected as a weak staining intensity by IHC. In some embodiments, the PD-L1 biomarker is detected as a moderate staining intensity by IHC. In some embodiments, the PD-L1 biomarker is detected as a strong staining intensity by IHC.

In some embodiments, the PD-L1 biomarker is detected on tumor cells, tumor infiltrating immune cells or combinations thereof using protein expression analysis such as IHC analysis. Tumor infiltrating immune cells include, but is not limited to, intratumoral immune cells, peritumoral immune cells or any combinations thereof, other tumor stroma cells (e.g. fibroblasts). Such tumor infiltrating immune cells can be T lymphocytes (such as CD8+ T lymphocytes and/or CD4+ T lymphocytes), B lymphocytes, or other bone marrow-lineage cells including granulocytes (neutrophils, eosinophils, basophils), monocytes, macrophages, dendritic cells (i.e., interdigitating dendritic cells), histiocytes, and natural killer cells.

In some embodiments, the staining for the PD-L1 biomarker is detected as membrane staining, cytoplasmic staining and combinations thereof. In other embodiments, the absence of the PD-L1 biomarker is detected as absent or no staining in the sample.

In some embodiments, the PD-L1 biomarker is detected in the sample by nucleic acid expression. In some embodiments, the nucleic acid expression is determined using qPCR, rtPCR, RNA-seq, multiplex qPCR or RT-qPCR, microarray analysis, SAGE, MassARRAY technique, or FISH.

In some embodiments, the PD-L1 biomarker is detected on tumor cells, tumor infiltrating immune cells, stromal cells and combinations thereof using nucleic acid expression such as qPCR analysis.

In some embodiments of any of the methods, assays and/or kits, the PD-L1 axis binding antagonist is selected from the group consisting of a PD-L1 binding antagonist and a PD-1 binding antagonist.

In some embodiments of any of the methods, assays and/or kits, the PD-L1 axis binding antagonist is a PD-L1 binding antagonist. In some embodiments of any of the methods, assays and/or kits, the PD-L1 binding antagonist inhibits the binding of PD-L1 to its ligand binding partners. In some embodiments of any of the methods, assays and/or kits, the PD-L1 binding antagonist inhibits the binding of PD-L1 to PD-1. In some embodiments of any of the methods, assays and/or kits, the PD-L1 binding antagonist inhibits the binding of PD-L1 to B7-1. In some embodiments of any of the methods, assays and/or kits, the PD-L1 binding antagonist inhibits the binding of PD-L1 to both PD-1 and B7-1.

In some embodiments of any of the methods, assays and/or kits, the PD-L1 binding antagonist is an antibody. In some embodiments of any of the methods, assays and/or kits, the antibody is a monoclonal antibody. In some embodiments of any of the methods, assays and/or kits, the antibody is a human, humanized or chimeric antibody.

In some embodiments of any of the methods, assays and/or kits, the PD-L1 axis binding antagonist is a PD-1 binding antagonist. In some embodiments of any of the methods, assays and/or kits, the PD-1 binding antagonist inhibits the binding of PD-1 to its ligand binding partners. In some embodiments of any of the methods, assays and/or kits, the PD-1 binding antagonist inhibits the binding of PD-1 to PD-L1. In some embodiments of any of the methods, assays and/or kits, the PD-1 binding antagonist inhibits the binding of PD-1 to PD-L2. In some embodiments of any of the methods, assays and/or kits, the PD-1 binding antagonist inhibits the binding of PD-1 to both PD-L1 and PD-L2.

In some embodiments, the sample obtained from the individual is selected from the group consisting of tissue, whole blood, plasma, serum and combinations thereof. In some embodiments, the sample is a tissue sample. In some embodiments, the sample is a tumor tissue sample. In some embodiments, the tumor tissue sample comprises tumor cells, tumor infiltrating immune cells, stromal cells or any combinations thereof.

In some embodiments, the sample is obtained prior to treatment with a PD-L1 axis binding antagonist. In some embodiments, the tissue sample is formalin fixed and paraffin embedded, archival, fresh or frozen In some embodiments, the sample is whole blood. In some embodiments, the whole blood comprises immune cells, circulating tumor cells and any combinations thereof.

In some embodiments, the disease or disorder is a proliferative disease or disorder. In some embodiments, the disease or disorder is an immune-related disease or disorder. In some embodiments, the disease or disorder is cancer. In some embodiments, the cancer is non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, merkel cell cancer, and other hematologic malignancies.

Presence and/or expression levels/amount of a biomarker (e.g., PD-L1) can be determined qualitatively and/or quantitatively based on any suitable criterion known in the art, including but not limited to DNA, mRNA, cDNA, proteins, protein fragments and/or gene copy number. In certain embodiments, presence and/or expression levels/amount of a biomarker in a first sample is increased or elevated as compared to presence/absence and/or expression levels/amount in a second sample. In certain embodiments, presence/absence and/or expression levels/amount of a biomarker in a first sample is decreased or reduced as compared to presence and/or expression levels/amount in a second sample. In certain embodiments, the second sample is a reference sample, reference cell, reference tissue, control sample, control cell, or control tissue. Additional disclosures for determining presence/absence and/or expression levels/amount of a gene are described herein.

In some embodiments of any of the methods, elevated expression refers to an overall increase of about any of 10%, 20%, 30%, 40%, 50%, 60%, 70%, 80%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, the elevated expression refers to the increase in expression level/amount of a biomarker in the sample wherein the increase is at least about any of 1.5×, 1.75×, 2×, 3×, 4×, 5×, 6×, 7×, 8×, 9×, 10×, 25×, 50×, 75×, or 100× the expression level/amount of the respective biomarker in a reference sample, reference cell, reference tissue, control sample, control cell, or control tissue. In some embodiments, elevated expression refers to an overall increase of greater than about 1.5 fold, about 1.75 fold, about 2 fold, about 2.25 fold, about 2.5 fold, about 2.75 fold, about 3.0 fold, or about 3.25 fold as compared to a reference sample, reference cell, reference tissue, control sample, control cell, control tissue, or internal control (e.g., housekeeping gene).

In some embodiments of any of the methods, reduced expression refers to an overall reduction of about any of 10%, 20%, 30%, 40%, 50%, 60%, 70%, 80%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, reduced expression refers to the decrease in expression level/amount of a biomarker in the sample wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference sample, reference cell, reference tissue, control sample, control cell, or control tissue.

Presence and/or expression level/amount of various biomarkers in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (as for example Serum ELISA), biochemical enzymatic activity assays, in situ hybridization, Southern analysis, Northern analysis, whole genome sequencing, polymerase chain reaction ("PCR") including quantitative real time PCR ("qRT-PCR") and other amplification type detection methods, such as, for example, branched DNA, SISBA, TMA and the like), RNA-Seq, FISH, microarray analysis, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

In some embodiments, presence and/or expression level/amount of a biomarker is determined using a method comprising: (a) performing gene expression profiling, PCR (such as rtPCR or qRT-PCR), RNA-seq, microarray analysis, SAGE, MassARRAY technique, or FISH on a sample (such as a subject cancer sample); and b) determining presence and/or expression level/amount of a biomarker in the sample. In some embodiments, the microarray method comprises the use of a microarray chip having one or more nucleic acid molecules that can hybridize under stringent conditions to a nucleic acid molecule encoding a gene mentioned above or having one or more polypeptides (such as peptides or antibodies) that can bind to one or more of the proteins encoded by the genes mentioned above. In one embodiment, the PCR method is qRT-PCR. In one embodiment, the PCR method is multiplex-PCR. In some embodiments, gene expression is measured by microarray. In some embodiments, gene expression is measured by qRT-PCR. In some embodiments, expression is measured by multiplex-PCR.

Methods for the evaluation of mRNAs in cells are well known and include, for example, hybridization assays using complementary DNA probes (such as in situ hybridization using labeled riboprobes specific for the one or more genes, Northern blot and related techniques) and various nucleic acid amplification assays (such as RT-PCR using complementary primers specific for one or more of the genes, and other amplification type detection methods, such as, for example, branched DNA, SISBA, TMA and the like).

Samples from mammals can be conveniently assayed for mRNAs using Northern, dot blot or PCR analysis. In addition, such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined.

Optional methods include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes whose expression correlates with increased or reduced clinical benefit of anti-angiogenic therapy may be arrayed on a solid support. Hybridization of a labeled probe with a particular array member indicates that the sample from which the probe was derived expresses that gene.

According to some embodiments, presence and/or expression level/amount is measured by observing protein expression levels of an aforementioned gene. In certain embodiments, the method comprises contacting the biological sample with antibodies to a biomarker (e.g., anti-PD-L1 antibodies) described herein under conditions permissive for binding of the biomarker, and detecting whether a complex is formed between the antibodies and biomarker. Such method may be an in vitro or in vivo method. In one embodiment, an antibody is used to select subjects eligible for therapy with PD-L1 axis binding antagonist e.g., a biomarker for selection of individuals.

In certain embodiments, the presence and/or expression level/amount of biomarker proteins in a sample is examined using IHC and staining protocols. IHC staining of tissue sections has been shown to be a reliable method of determining or detecting presence of proteins in a sample. In some embodiments of any of the methods, assays and/or kits, the PD-L1 biomarker is PD-L1. In some embodiments, PD-L1 is detected by immunohistochemistry. In some embodiments, elevated expression of a PD-L1 biomarker in a sample from an individual is elevated protein expression and, in further embodiments, is determined using IHC. In one embodiment, expression level of biomarker is determined using a method comprising: (a) performing IHC analysis of a sample (such as a subject cancer sample) with an antibody; and b) determining expression level of a biomarker in the sample. In some embodiments, IHC staining intensity is determined relative to a reference. In some embodiments, the reference is a reference value. In some embodiments, the reference is a reference sample (e.g., control cell line staining sample or tissue sample from non-cancerous patient).

IHC may be performed in combination with additional techniques such as morphological staining and/or fluorescence in-situ hybridization. Two general methods of IHC are available; direct and indirect assays. According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for IHC typically will be labeled with a detectable moiety. Numerous labels are available which can be generally grouped into the following categories: (a) Radioisotopes, such as $^{35}$S, $^{14}$C, $^{125}$I, $^{3}$H, and $^{131}$I; (b) colloidal gold particles; (c) fluorescent labels including, but are not limited to, rare earth chelates (europium chelates), Texas Red, rhodamine, fluorescein, dansyl, Lissamine, umbelliferone, phycocrytherin, phycocyanin, or commercially available fluorophores such SPECTRUM ORANGE7 and SPECTRUM GREEN7 and/or derivatives of any one or more of the above; (d) various enzyme-substrate labels are available and U.S. Pat. No. 4,275,149 provides a review of some of these. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations include, for example, horseradish peroxidase (HRPO) with hydrogen peroxidase as a substrate; alkaline phosphatase (AP) with para-Nitrophenyl phosphate as chromogenic substrate; and β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase). For a general review of these, see U.S. Pat. Nos. 4,275,149 and 4,318,980.

In some embodiments of any of the methods, PD-L1 is detected by immunohistochemistry using an anti-PD-L1 diagnostic antibody (i.e., primary antibody). In some embodiments, the PD-L1 diagnostic antibody specifically binds human PD-L1. In some embodiments, the PD-L1 diagnostic antibody is a nonhuman antibody. In some embodiments, the PD-L1 diagnostic antibody is a rat, mouse, or rabbit antibody. In some embodiments, the PD-L1 diagnostic antibody is a monoclonal antibody. In some embodiments, the PD-L1 diagnostic antibody is directly labeled.

Specimens thus prepared may be mounted and coverslipped. Slide evaluation is then determined, e.g., using a microscope, and staining intensity criteria, routinely used in the art, may be employed. In one embodiment, it is understood that when cells and/or tissue from a tumor is examined using IHC, staining is generally determined or assessed in tumor cell and/or tissue (as opposed to stromal or surrounding tissue that may be present in the sample). In some embodiments, it is understood that when cells and/or tissue from a tumor is examined using IHC, staining includes determining or assessing in tumor infiltrating immune cells, including intratumoral or peritumoral immune cells. In some embodiments, the presence of a PD-L1 biomarker is detected by IHC in >0% of the sample, in at least 1% of the sample, in at least 5% of the sample, in at least 10% of the sample.

In some embodiments of any of the methods, assays, and/or kits, the presence of a PD-L1 biomarker is detected by IHC with PD-L1 staining of any intensity. In some embodiments, the PD-L1 biomarker is detected by IHC as a weak staining intensity. In some embodiments, the PD-L1 biomarker is detected by IHC as a moderate staining intensity. In some embodiments, the PD-L1 biomarker is detected by IHC as a strong staining intensity.

In some embodiments, the PD-L1 biomarker is detected by IHC in tumor cells, tumor infiltrating immune cells and combinations thereof.

Anti-PD-L1 antibodies suitable for use in IHC are well known in the art. One of ordinary skill understands that additional suitable anti-PD-L1 antibodies may be identified and characterized by comparing with anti-PD-L1 antibodies using the IHC protocol disclosed herein, for example.

Positive tissue controls are exemplified using placenta and tonsil tissues (strong PD-L1 staining intensity); HEK-293 cells transfected with recombinant human PD-L1 (varying degrees of PD-L1 staining intensity from weak, moderate and strong intensity). The following may be referred to for exemplary PD-L1 IHC criteria.

| PD-L1 Status | Staining criteria |
|---|---|
| Negative | 0% membrane staining or cytoplasmic staining or combinations of both at ANY staining intensity |
| Positive | >0% membrane staining or cytoplasmic staining or combinations of both at ANY staining intensity |
| | ≥1% membrane staining or cytoplasmic staining or combinations of both at ANY staining intensity |
| | ≥5% membrane staining or cytoplasmic staining or combinations of both at ANY staining intensity |

-continued

| PD-L1 Status | Staining criteria |
|---|---|
| | ≥10% membrane staining or cytoplasmic staining or combinations of both at ANY staining intensity |

In some embodiments, the criteria for PD-L1 IHC diagnostic assessment is provided as follows:

| PD-L1 Diagnostic Assessment | IHC Scores |
|---|---|
| Absence of any discernible PD-L1 staining OR Presence of discernible PD-L1 staining of any intensity in tumor-infiltrating immune cells covering <1% of tumor area occupied by tumor cells, associated intratumoral, and contiguous peri-tumoral desmoplastic stroma | IHC 0 |
| Presence of discernible PD-L1 staining of any intensity in tumor-infiltrating immune cells covering between ≥1% to <5% of tumor area occupied by tumor cells, associated intratumoral, and contiguous peri-tumoral desmoplastic stroma | IHC 1 |
| Presence of discernible PD-L1 staining of any intensity in tumor infiltrating immune cells covering between ≥5% to <10% of tumor area occupied by tumor cells, associated intratumoral, and contiguous peri-tumoral desmoplastic stroma | IHC 2 |
| Presence of discernible PD-L1 staining of any intensity in tumor infiltrating immune cells covering ≥10% of tumor area occupied by tumor cells, associated intratumoral, and contiguous peri-tumoral desmoplastic stroma | IHC 3 |

In alternative methods, the sample may be contacted with an antibody specific for said biomarker under conditions sufficient for an antibody-biomarker complex to form, and then detecting said complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

Presence and/or expression level/amount of a selected biomarker in a tissue or cell sample may also be examined by way of functional or activity-based assays. For instance, if the biomarker is an enzyme, one may conduct assays known in the art to determine or detect the presence of the given enzymatic activity in the tissue or cell sample.

In certain embodiments, the samples are normalized for both differences in the amount of the biomarker assayed and variability in the quality of the samples used, and variability between assay runs. Such normalization may be accomplished by detecting and incorporating the expression of certain normalizing biomarkers, including well known housekeeping genes. Alternatively, normalization can be based on the mean or median signal of all of the assayed genes or a large subset thereof (global normalization approach). On a gene-by-gene basis, measured normalized amount of a subject tumor mRNA or protein is compared to the amount found in a reference set. Normalized expression levels for each mRNA or protein per tested tumor per subject can be expressed as a percentage of the expression level measured in the reference set. The presence and/or expression level/amount measured in a particular subject sample to be analyzed will fall at some percentile within this range, which can be determined by methods well known in the art.

In one embodiment, the sample is a clinical sample. In another embodiment, the sample is used in a diagnostic assay. In some embodiments, the sample is obtained from a primary or metastatic tumor. Tissue biopsy is often used to obtain a representative piece of tumor tissue. Alternatively, tumor cells can be obtained indirectly in the form of tissues or fluids that are known or thought to contain the tumor cells of interest. For instance, samples of lung cancer lesions may be obtained by resection, bronchoscopy, fine needle aspiration, bronchial brushings, or from sputum, pleural fluid or blood. Genes or gene products can be detected from cancer or tumor tissue or from other body samples such as urine, sputum, serum or plasma. The same techniques discussed above for detection of target genes or gene products in cancerous samples can be applied to other body samples. Cancer cells may be sloughed off from cancer lesions and appear in such body samples. By screening such body samples, a simple early diagnosis can be achieved for these cancers. In addition, the progress of therapy can be monitored more easily by testing such body samples for target genes or gene products.

In certain embodiments, a reference sample, reference cell, reference tissue, control sample, control cell, or control tissue is a single sample or combined multiple samples from the same subject or individual that are obtained at one or more different time points than when the test sample is obtained. For example, a reference sample, reference cell, reference tissue, control sample, control cell, or control tissue is obtained at an earlier time point from the same subject or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic.

In certain embodiments, a reference sample, reference cell, reference tissue, control sample, control cell, or control tissue is a combined multiple samples from one or more healthy individuals who are not the subject or individual. In certain embodiments, a reference sample, reference cell, reference tissue, control sample, control cell, or control tissue is a combined multiple samples from one or more individuals with a disease or disorder (e.g., cancer) who are not the subject or individual. In certain embodiments, a reference sample, reference cell, reference tissue, control sample, control cell, or control tissue is pooled RNA samples from normal tissues or pooled plasma or serum samples from one or more individuals who are not the subject or individual. In certain embodiments, a reference sample, reference cell, reference tissue, control sample, control cell, or control tissue is pooled RNA samples from tumor tissues or pooled plasma or serum samples from one or more individuals with a disease or disorder (e.g., cancer) who are not the subject or individual.

In some embodiments, the sample is a tissue sample from the individual. In some embodiments, the tissue sample is a tumor tissue sample (e.g., biopsy tissue). In some embodiments, the tissue sample is lung tissue. In some embodiments, the tissue sample is renal tissue. In some embodiments, the tissue sample is skin tissue. In some embodiments, the tissue sample is pancreatic tissue. In some embodiments, the tissue sample is gastric tissue. In some embodiments, the tissue sample is bladder tissue. In some embodiments, the tissue sample is esophageal tissue. In some embodiments, the tissue sample is mesothelial tissue.

In some embodiments, the tissue sample is breast tissue. In some embodiments, the tissue sample is thyroid tissue. In some embodiments, the tissue sample is colorectal tissue. In some embodiments, the tissue sample is head and neck tissue. In some embodiments, the tissue sample is osteosarcoma tissue. In some embodiments, the tissue sample is prostate tissue. In some embodiments, the tissue sample is ovarian tissue, HCC (liver), blood cells, lymph nodes, bone/bone marrow.

In some embodiments of any of the methods, the disease or disorder is a tumor. In some embodiments, the tumor is a malignant cancerous tumor (i.e., cancer). In some embodiments, the tumor and/or cancer is a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, polymphocytic leukemia, or hairy cell leukemia) or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further divided into those of epithelial cell origin and those of non-epithelial cell origin. Examples of epithelial cell solid tumors include tumors of the gastrointestinal tract, colon, colorectal (e.g., basaloid colorectal carcinoma), breast, prostate, lung, kidney, liver, pancreas, ovary (e.g., endometrioid ovarian carcinoma), head and neck, oral cavity, stomach, duodenum, small intestine, large intestine, anus, gall bladder, labium, nasopharynx, skin, uterus, male genital organ, urinary organs (e.g., urothelium carcinoma, dysplastic urothelium carcinoma, transitional cell carcinoma), bladder, and skin. Solid tumors of non-epithelial origin include sarcomas, brain tumors, and bone tumors. In some embodiments, the cancer is non-small cell lung cancer (NSCLC). In some embodiments, the cancer is second-line or third-line locally advanced or metastatic non-small cell lung cancer. In some embodiments, the cancer is adenocarcinoma. In some embodiments, the cancer is squamous cell carcinoma.

In some embodiments, the PD-L1 biomarker is detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometery, HPLC, qPCR, RT-qPCR, multiplex qPCR or RT-qPCR, RNA-seq, microarray analysis, SAGE, MassARRAY technique, and FISH, and combinations thereof. In some embodiments, the PD-L1 biomarker is detected using FACS analysis. In some embodiments, the PD-L1 biomarker is PD-L1. In some embodiments, the PD-L1 expression is detected in blood samples. In some embodiments, the PD-L1 expression is detected on circulating immune cells in blood samples. In some embodiments, the circulating immune cell is a CD3+/CD8+ T cell. In some embodiments, prior to analysis, the immune cells are isolated from the blood samples. Any suitable method to isolate/enrich such population of cells may be used including, but not limited to, cell sorting. In some embodiments, the PD-L1 expression is elevated in samples from individuals that respond to treatment with an inhibitor of the PD-L1/PD-1 axis pathway, such as an anti-PD-L1 antibody. In some embodiments, the PD-L1 expression is elevated on the circulating immune cells, such as the CD3+/CD8+ T cells, in blood samples.

Therapeutic Methods

Provided are methods for treating a disease or disorder in an individual, the method comprising: determining the presence of a PD-L1 biomarker in a sample from the individual, and administering an effective amount of a PD-L1 axis binding antagonist to the individual.

Further provided herein are treating a disease or disorder in an individual comprising administering to the individual an effective amount of a PD-L1 axis binding antagonist, wherein treatment is based upon the presence of a PD-L1 biomarker in a sample from the individual.

In some embodiments, the PD-L1 biomarker is selected from the group consisting of PD-L1, PD-1, PD-L2 and any combinations thereof.

In some embodiments, the PD-L1 biomarker is an immune-related marker. An immune-related marker refers to a marker that is expressed by immune cells, or by other cells (e.g., tumor cells, endothelial cells, fibroblasts or other stromal cells). If expressed by other than immune cells, the marker may be involved in regulation of immune cell biology and function, such as activation, priming, antigen recognition and presentation, cytokine and chemokine production, proliferation, migration, survival, antibody production and other. In some embodiments, the immune-related marker is a T-cell related marker. In some embodiments, the T-cell related marker is selected from the group consisting of CD8A, IFN-g, EOMES, Granzyme-A, CXCL9 and any combination thereof. In some embodiments, the immune-related marker is selected from the group consisting of CX3CL1, CD45RO, IDO1, Galectin 9, MIC-A, MIC-B, CTLA-4 and any combinations thereof.

In some embodiments, the presence of a PD-L1 biomarker indicates that the individual is likely to have increased clinical benefit when the individual is treated with the PD-L1 axis binding antagonist. In some embodiments, the increased clinical benefit comprises a relative increase in one or more of the following: overall survival (OS), progression free survival (PFS), complete response (CR), partial response (PR) and combinations thereof.

In some embodiments, the PD-L1 biomarker is absent from the sample when it comprises 0% of the sample. In some embodiments, the PD-L1 biomarker is present in the sample when it comprises more than 0% of the sample. In some embodiments, the PD-L1 biomarker is present in at least 1% of the sample. In some embodiments, the PD-L1 biomarker is present in at least 5% of the sample. In some embodiments, the PD-L1 biomarker is present in at least 10% of the sample.

In some embodiments, the PD-L1 biomarker is detected in the sample using a method selected from the group consisting of FACS, Western blot, ELISA, immunoprecipitation, immunohistochemistry, immunofluorescence, radio-immunoassay, dot blotting, immunodetection methods, HPLC, surface plasmon resonance, optical spectroscopy, mass spectrometery, HPLC, qPCR, RT-qPCR, multiplex qPCR or RT-qPCR, RNA-seq, microarray analysis, SAGE, MassARRAY technique, and FISH, and combinations thereof.

In some embodiments, the PD-L1 biomarker is detected in the sample by protein expression. In some embodiments, protein expression is determined by immunohistochemistry (IHC). In some embodiments, PD-L1 biomarker is detected using an anti-PD-L1 antibody.

In some embodiments, the PD-L1 biomarker is detected as a weak staining intensity by IHC. In some embodiments, the PD-L1 biomarker is detected as a moderate staining intensity by IHC. In some embodiments, the PD-L1 biomarker is detected as a strong staining intensity by IHC.

In some embodiments, the PD-L1 biomarker is detected on tumor cells, tumor infiltrating immune cells or combinations thereof using protein expression analysis such as IHC analysis. Tumor infiltrating immune cells include, but is not limited to, intratumoral immune cells, peritumoral immune cells or any combinations thereof, other tumor stroma cells (e.g. fibroblasts). Such tumor infiltrating immune cells can be T lymphocytes (such as CD8+ T lymphocytes and/or CD4+ T lymphocytes), B lymphocytes, or other bone marrow-lineage cells including granulocytes (neutrophils, eosinophils, basophils), monocytes, macrophages, dendritic cells (i.e., interdigitating dendritic cells), histiocytes, and natural killer cells.

In some embodiments, the staining for the PD-L1 biomarker is detected as membrane staining, cytoplasmic staining and combinations thereof. In other embodiments, the absence of the PD-L1 biomarker is detected as absent or no staining in the sample.

In some embodiments, the PD-L1 biomarker is detected in the sample by nucleic acid expression. In some embodiments, the nucleic acid expression is determined using qPCR, rtPCR, RNA-seq, multiplex qPCR or RT-qPCR, microarray analysis, SAGE, MassARRAY technique, or FISH.

In some embodiments, the PD-L1 biomarker is detected on tumor cells, tumor infiltrating immune cells, stromal cells and combinations thereof using nucleic acid expression such as qPCR analysis.

In some embodiments of any of the methods, assays and/or kits, the PD-L1 axis binding antagonist is selected from the group consisting of a PD-L1 binding antagonist and a PD-1 binding antagonist.

In some embodiments of any of the methods, assays and/or kits, the PD-L1 axis binding antagonist is a PD-L1 binding antagonist. In some embodiments of any of the methods, assays and/or kits, the PD-L1 binding antagonist inhibits the binding of PD-L1 to its ligand binding partners. In some embodiments of any of the methods, assays and/or kits, the PD-L1 binding antagonist inhibits the binding of PD-L1 to PD-1. In some embodiments of any of the methods, assays and/or kits, the PD-L1 binding antagonist inhibits the binding of PD-L1 to B7-1. In some embodiments of any of the methods, assays and/or kits, the PD-L1 binding antagonist inhibits the binding of PD-L1 to both PD-1 and B7-1.

In some embodiments of any of the methods, assays and/or kits, the PD-L1 binding antagonist is an antibody. In some embodiments of any of the methods, assays and/or kits, the antibody is a monoclonal antibody. In some embodiments of any of the methods, assays and/or kits, the antibody is a human, humanized or chimeric antibody.

In some embodiments of any of the methods, assays and/or kits, the PD-L1 axis binding antagonist is a PD-1 binding antagonist. In some embodiments of any of the methods, assays and/or kits, the PD-1 binding antagonist inhibits the binding of PD-1 to its ligand binding partners. In some embodiments of any of the methods, assays and/or kits, the PD-1 binding antagonist inhibits the binding of PD-1 to PD-L1. In some embodiments of any of the methods, assays and/or kits, the PD-1 binding antagonist inhibits the binding of PD-1 to PD-L2. In some embodiments of any of the methods, assays and/or kits, the PD-1 binding antagonist inhibits the binding of PD-1 to both PD-L1 and PD-L2.

Examples of anti-PD-L1 antibodies useful for the methods of this invention, and methods for making thereof are described in PCT patent application WO 2010/077634 A1, which are incorporated herein by reference.

In some embodiments, the anti-PD-L1 antibody is capable of inhibiting binding between PD-L1 and PD-1 and/or between PD-L1 and B7-1. In some embodiments, the anti-PD-L1 antibody is a monoclonal antibody. In some embodiments, the anti-PD-L1 antibody is an antibody fragment selected from the group consisting of Fab, Fab'-SH, Fv, scFv, and (Fab')2 fragments. In some embodiments, the anti-PD-L1 antibody is a humanized antibody. In some embodiments, the anti-PD-L1 antibody is a human antibody.

In one embodiment, the anti-PD-L1 antibody contains a heavy chain variable region polypeptide comprising an HVR-H1, HVR-H2 and HVR-H3 sequence, wherein:

```
(a) the HVR-H1 sequence is
                               (SEQ ID NO: 1)
GFTFSX1SWIH;

(b) the HVR-H2 sequence is
                               (SEQ ID NO: 2)
AWIX2PYGGSX3YYADSVKG;

(c) the HVR-H3 sequence is
                               (SEQ ID NO: 3)
RHWPGGFDY;
``` further wherein: X1 is D or G; X2 is S or L; X3 is T or S.

In one specific aspect, X1 is D; X2 is S and X3 is T. In another aspect, the polypeptide further comprises variable region heavy chain framework sequences juxtaposed between the HVRs according to the formula: (HC-FR1)-(HVR-H1)-(HC-FR2)-(HVR-H2)-(HC-FR3)-(HVR-H3)-(HC-FR4). In yet another aspect, the framework sequences are derived from human consensus framework sequences. In a further aspect, the framework sequences are VH subgroup III consensus framework. In a still further aspect, at least one of the framework sequences is the following:

```
HC-FR1 is
                               (SEQ ID NO: 4)
EVQLVESGGGLVQPGGSLRLSCAAS

HC-FR2 is
                               (SEQ ID NO: 5)
WVRQAPGKGLEWV

HC-FR3 is
                               (SEQ ID NO: 6)
RFTISADTSKNTAYLQMNSLRAEDTAVYYCAR

HC-FR4 is
                               (SEQ ID NO: 7)
WGQGTLVTVSA.
```

In a still further aspect, the heavy chain polypeptide is further combined with a variable region light chain comprising an HVR-L1, HVR-L2 and HVR-L3, wherein:

```
(a) the HVR-L1 sequence is
                               (SEQ ID NO: 8)
RASQX4X5X6TX7X8A;

(b) the HVR-L2 sequence is
                               (SEQ ID NO: 9)
SASX9LX10S;

(c) the HVR-L3 sequence is
                               (SEQ ID NO: 10)
QQX11X12X13X14PX15T;
``` further wherein: X4 is D or V; X5 is V or I; X6 is S or N; X7 is A or F; X8 is V or L; X9 is F or T; X10 is Y or A; X11 is Y, G, F, or S; X12 is L, Y, F or W; X13 is Y, N, A, T, G, F or I; X14 is H, V, P, T or I; X15 is A, W, R, P or T.

In a still further aspect, X4 is D; X5 is V; X6 is S; X7 is A; X8 is V; X9 is F; X10 is Y; X11 is Y; X12 is L; X13 is Y; X14 is H; X15 is A. In a still further aspect, the light chain further comprises variable region light chain framework sequences juxtaposed between the HVRs according to the formula: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the framework sequences are VL kappa I consensus framework. In a still further aspect, at least one of the framework sequence is the following:

```
LC-FR1 is
                               (SEQ ID NO: 11)
DIQMTQSPSSLSASVGDRVTITC

LC-FR2 is
                               (SEQ ID NO: 12)
WYQQKPGKAPKLLIY

LC-FR3 is
                               (SEQ ID NO: 13)
GVPSRFSGSGSGTDFTLTISSLQPEDFATYYC

LC-FR4 is
                               (SEQ ID NO: 14)
FGQGTKVEIKR
```

In another embodiment, provided is an isolated anti-PD-L1 antibody or antigen binding fragment comprising a heavy chain and a light chain variable region sequence, wherein:

```
(a) the heavy chain comprises and HVR-H1, HVR-H2
and HVR-H3, wherein further:
(i) the HVR-H1 sequence is
                               (SEQ ID NO: 1)
GFTFSX1SWIH;

(ii) the HVR-H2 sequence is
                               (SEQ ID NO: 2)
AWIX2PYGGSX3YYADSVKG (iii) the HVR-H3 sequence is
                               (SEQ ID NO: 3)
RHWPGGFDY,
and (b) the light chain comprises and HVR-L1,
HVR-L2 and HVR-L3, wherein further:
(i) the HVR-L1 sequence is
                               (SEQ ID NOs: 8)
RASQX4X5X6TX7X8A (ii) the HVR-L2 sequence is
                               (SEQ ID NOs: 9)
SASX9LX10S;
and (iii) the HVR-L3 sequence is
                               (SEQ ID NOs: 10)
QQX11X12X13X14PX15T;
```

Further wherein: X1 is D or G; X2 is S or L; X3 is T or S; X4 is D or V; X5 is V or I; X6 is S or N; X7 is A or F; X8 is V or L; X9 is F or T; X10 is Y or A; X11 is Y, G, F, or S; X12 is L, Y, F or W; X13 is Y, N, A, T, G, F or I; X14 is H, V, P, T or I; X15 is A, W, R, P or T.

In a specific aspect, X1 is D; X2 is S and X3 is T. In another aspect, X4 is D; X5 is V; X6 is S; X7 is A; X8 is V;

X9 is F; X10 is Y; X11 is Y; X12 is L; X13 is Y; X14 is H; X15 is A. In yet another aspect, X1 is D; X2 is S and X3 is T, X4 is D; X5 is V; X6 is S; X7 is A; X8 is V; X9 is F; X10 is Y; X11 is Y; X12 is L; X13 is Y; X14 is H and X15 is A.

In a further aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                    (SEQ ID NO:  4)
EVQLVESGGGLVQPGGSLRLSCAAS

HC-FR2
                                    (SEQ ID NO:  5)
WVRQAPGKGLEWV

HC-FR3
                                    (SEQ ID NO:  6)
RFTISADTSKNTAYLQMNSLRAEDTAVYYCAR

HC-FR4
                                    (SEQ ID NO:  7)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                    (SEQ ID NO:  11)
DIQMTQSPSSLSASVGDRVTITC

LC-FR2
                                    (SEQ ID NO:  12)
WYQQKPGKAPKLLIY

LC-FR3
                                    (SEQ ID NO:  13)
GVPSRFSGSGSGTDFTLTISSLQPEDFATYYC

LC-FR4
                                    (SEQ ID NO:  14)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, provided is an anti-PD-L1 antibody comprising a heavy chain and a light chain variable region sequence, wherein:

(a) the heavy chain further comprises and HVR-H1, HVR-H2 and an HVR-H3 sequence having at least 85% sequence identity to GFTFSDSWIH (SEQ ID NO:15), AWISPYGGSTYYADSVKG (SEQ ID NO:16) and RHWPGGFDY (SEQ ID NO:3), respectively, or (b) the light chain further comprises an HVR-L1, HVR-L2 and an HVR-L3 sequence having at least 85% sequence identity to RASQDVSTAVA (SEQ ID NO:17), SASFLYS (SEQ ID NO:18) and QQYLYH-PAT (SEQ ID NO:19), respectively.

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                    (SEQ ID NO:  4)
EVQLVESGGGLVQPGGSLRLSCAAS

HC-FR2
                                    (SEQ ID NO:  5)
WVRQAPGKGLEWV

HC-FR3
                                    (SEQ ID NO:  6)
RFTISADTSKNTAYLQMNSLRAEDTAVYYCAR

HC-FR4
                                    (SEQ ID NO:  7)
WGQGTLVTVSA .
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                    (SEQ ID NO:  11)
DIQMTQSPSSLSASVGDRVTITC

LC-FR2
                                    (SEQ ID NO:  12)
WYQQKPGKAPKLLIY

LC-FR3
                                    (SEQ ID NO:  13)
GVPSRFSGSGSGTDFTLTISSLQPEDFATYYC
```

-continued

```
LC-FR4
                              (SEQ ID NO: 14)
FGQGTKVEIKR
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, provided is an isolated anti-PD-L1 antibody comprising a heavy chain and a light chain variable region sequence, wherein:

```
(a) the heavy chain sequence has at least 85%
sequence identity to the heavy chain
sequence:
                              (SEQ ID NO: 20)
EVQLVESGGGLVQPGGSLRLSCAASGFTFSDSWIHWVRQAPGKGL

EWVAWISPYGGSTYYADSVKGRFTISADTSKNTAYLQMNSLRAEDT

AVYYCARRHWPGGFDYWGQGTLVTVSA,
or (b) the light chain sequences has at least 85%
sequence identity to the light chain sequence:
                              (SEQ ID NO: 21)
DIQMTQSPSSLSASVGDRVTITCRASQDVSTAVAWYQQKPGKAP

KLLIY SASFLYSGVPSRFSGSGSGTDFTLTISSLQPEDFATYY

CQQYLYHPATFGQGTKVEIKR.
```

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                              (SEQ ID NO: 4)
EVQLVESGGGLVQPGGSLRLSCAAS

HC-FR2
                              (SEQ ID NO: 5)
WVRQAPGKGLEWV
```

-continued

```
HC-FR3
                              (SEQ ID NO: 6)
RFTISADTSKNTAYLQMNSLRAEDTAVYYCAR

HC-FR4
                              (SEQ ID NO: 7)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                              (SEQ ID NO: 11)
DIQMTQSPSSLSASVGDRVTITC

LC-FR2
                              (SEQ ID NO: 12)
WYQQKPGKAPKLLIY

LC-FR3
                              (SEQ ID NO: 13)
GVPSRFSGSGSGTDFTLTISSLQPEDFATYYC

LC-FR4
                              (SEQ ID NO: 14)
FGQGTKVEIKR
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, the invention provides for compositions comprising any of the above described anti-PD-L1 antibodies in combination with at least one pharmaceutically-acceptable carrier.

In a still further embodiment, provided is an isolated nucleic acid encoding a light chain or a heavy chain variable region sequence of an anti-PD-L1 antibody, wherein:

(a) the heavy chain further comprises and HVR-H1, HVR-H2 and an HVR-H3 sequence having at least 85% sequence identity to GFTFSDSWIH (SEQ ID NO:15), AWISPYGGSTYYADSVKG (SEQ ID NO:16) and RHWPGGFDY (SEQ ID NO:3), respectively, and (b) the light chain further comprises an HVR-L1, HVR-L2 and an HVR-L3 sequence having at least 85% sequence identity to RASQDVSTAVA (SEQ ID NO:17), SASFLYS (SEQ ID NO:18) and QQYLYHPAT (SEQ ID NO:19), respectively.

In a specific aspect, the sequence identity is 86%, 87%, 88%, 89%, 90%, 91%, 92%, 93%, 94%, 95%, 96%, 97%, 98%, 99% or 100%. In aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                              (SEQ ID NO: 4)
EVQLVESGGGLVQPGGSLRLSCAAS

HC-FR2
                              (SEQ ID NO: 5)
WVRQAPGKGLEWV

HC-FR3
                              (SEQ ID NO: 6)
RFTISADTSKNTAYLQMNSLRAEDTAVYYCAR

HC-FR4
                              (SEQ ID NO: 7)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                              (SEQ ID NO: 11)
DIQMTQSPSSLSASVGDRVTITC

LC-FR2
                              (SEQ ID NO: 12)
WYQQKPGKAPKLLIY

LC-FR3
                              (SEQ ID NO: 13)
GVPSRFSGSGSGTDFTLTISSLQPEDFATYYC

LC-FR4
                              (SEQ ID NO: 14)
FGQGTKVEIKR
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further aspect, the effector-less Fc mutation is an N297A or D265A/N297A substitution in the constant region.

In a still further aspect, the nucleic acid further comprises a vector suitable for expression of the nucleic acid encoding any of the previously described anti-PD-L1 antibodies. In a still further specific aspect, the vector further comprises a host cell suitable for expression of the nucleic acid. In a still further specific aspect, the host cell is a eukaryotic cell or a prokaryotic cell. In a still further specific aspect, the eukaryotic cell is a mammalian cell, such as Chinese Hamster Ovary (CHO).

The anti-PD-L1 antibody or antigen binding fragment thereof, may be made using methods known in the art, for example, by a process comprising culturing a host cell containing nucleic acid encoding any of the previously described anti-PD-L1 antibodies or antigen-binding fragment in a form suitable for expression, under conditions suitable to produce such antibody or fragment, and recovering the antibody or fragment. In a still further embodiment, the invention provides for a composition comprising an anti-PD-L1 antibody or antigen binding fragment thereof as provided herein and at least one pharmaceutically acceptable carrier.

A. Antibodies

1. Antibody Affinity

In certain embodiments, an antibody provided herein has a dissociation constant (Kd) of $\leq 1$ µM. In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, NJ) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. *Nat. Med.* 9:129-134 (2003). For a review of scFv fragments, see, e.g., Pluckthún, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing Veloci-Mouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178:1-37 (O'Brien et al., ed., Human Press, Totowa, NJ, 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, NJ, 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g., a bispecific antibody. Multispecific antibodies are monoclonal antibodies that have binding specificities for at least two different sites. In certain embodiments, one of the binding specificities is for PD-L1 and the other is for any other antigen. In certain embodiments, bispecific antibodies may bind to two different epitopes of PD-L1. Bispecific antibodies may also be used to localize cytotoxic agents to cells which express PD-L1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g., Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g., US 2006/0025576A1).

The antibody or fragment herein also includes a "Dual Acting FAb" or "DAF" comprising an antigen binding site that binds to PD-L1 as well as another, different antigen.

7. Antibody Variants a) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al., Biotech. Bioeng. 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

b) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoetic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).) In certain embodiments, an antibody variant comprises an Fc region with one or more amino acid substitutions which improve ADCC, e.g., substitutions at positions 298, 333, and/or 334 of the Fc region (EU numbering of residues). In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, Nature 322:738-40 (1988); U.S. Pat. Nos. 5,648,260; 5,624,821; and WO 94/29351 concerning other examples of Fc region variants.

c) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

d) Immunoconjugates

Further provided herein are immunoconjugates comprising an anti-PD-L1 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $tc^{99}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A.).

C. Binding Polypeptides

Binding polypeptides are polypeptides that bind, preferably specifically, to PD-L1 as described herein. In some embodiments, the binding polypeptides are PD-L1 axis binding antagonist. Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such binding polypeptides that are capable of binding, preferably specifically, to a target, PD-L1, as described herein. Binding polypeptides may be identified without undue experimentation using well known techniques. In this regard, it is noted that techniques for screening polypeptide libraries for binding polypeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in Synthetic Peptides as Antigens, 130-149 (1986); Geysen et al., *J. Immunol. Meth.*, 102:259-274 (1987); Schoofs et al., *J. Immunol.*, 140:611-616 (1988), Cwirla, S. E. et al. (1990) *Proc. Natl. Acad. Sci. USA*, 87:6378; Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363, and Smith, G. P. (1991) *Current Opin. Biotechnol.*, 2:668).

In this regard, bacteriophage (phage) display is one well known technique which allows one to screen large polypeptide libraries to identify member(s) of those libraries which are capable of specifically binding to a target polypeptide, PD-L1. Phage display is a technique by which variant polypeptides are displayed as fusion proteins to the coat protein on the surface of bacteriophage particles (Scott, J. K. and Smith, G. P. (1990) *Science,* 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) *Proc. Natl. Acad. Sci. USA,* 87:6378) or protein (Lowman, H. B. et al. (1991) *Biochemistry,* 30:10832; Clackson, T. et al. (1991) *Nature,* 352: 624; Marks, J. D. et al. (1991), *J. Mol. Biol.,* 222:581; Kang, A. S. et al. (1991) *Proc. Natl. Acad. Sci. USA,* 88:8363) libraries on phage have been used for screening millions of polypeptides or oligopeptides for ones with specific binding properties (Smith, G. P. (1991) *Current Opin. Biotechnol.,* 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., *Gene,* 215: 439 (1998); Zhu et al., *Cancer Research,* 58(15): 3209-3214 (1998); Jiang et al., *Infection & Immunity,* 65(11): 4770-4777 (1997); Ren et al., *Gene,* 195(2): 303-311 (1997); Ren, *Protein Sci.,* 5: 1833 (1996); Efimov et al., *Virus Genes,* 10: 173 (1995)) and T7 phage display systems (Smith and Scott, *Methods in Enzymology,* 217: 228-257 (1993); U.S. Pat. No. 5,766,905) are also known.

Additional improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al. (1998) *Mol Biotech.,* 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

D. Binding Small Molecules

Provided herein are binding small molecules for use as a PD-L1 small molecule antagonist.

Binding small molecules are preferably organic molecules other than binding polypeptides or antibodies as defined herein that bind, preferably specifically, to PD-L1 as described herein. Binding organic small molecules may be identified and chemically synthesized using known methodology (see, e.g., PCT Publication Nos. WO00/00823 and WO00/39585). Binding organic small molecules are usually less than about 2000 daltons in size, alternatively less than about 1500, 750, 500, 250 or 200 daltons in size, wherein such organic small molecules that are capable of binding, preferably specifically, to a polypeptide as described herein may be identified without undue experimentation using well known techniques. In this regard, it is noted that techniques for screening organic small molecule libraries for molecules that are capable of binding to a polypeptide target are well known in the art (see, e.g., PCT Publication Nos. WO00/00823 and WO00/39585). Binding organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

E. Antagonist Polynucleotides

Provided herein are polynucleotide antagonists. The polynucleotide may be an antisense nucleic acid and/or a ribozyme. The antisense nucleic acids comprise a sequence complementary to at least a portion of an RNA transcript of a PD-L1 gene. However, absolute complementarity, although preferred, is not required.

A sequence "complementary to at least a portion of an RNA," referred to herein, means a sequence having sufficient complementarity to be able to hybridize with the RNA, forming a stable duplex; in the case of double stranded PD-L1 antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with an PD-L1 RNA it may contain and still form a stable duplex (or triplex as the case may be). One skilled in the art can ascertain a tolerable degree of mismatch by use of standard procedures to determine the melting point of the hybridized complex.

Polynucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333-335. Thus, oligonucleotides complementary to either the 5'- or 3'-non-translated, non-coding regions of the PD-L1 gene, could be used in an antisense approach to inhibit translation of endogenous PD-L1 mRNA. Polynucleotides complementary to the 5' untranslated region of the mRNA should include the complement of the AUG start codon. Antisense polynucleotides complementary to mRNA coding regions are less efficient inhibitors of translation but could be used in accordance with the invention. Whether designed to hybridize to the 5'-, 3'- or coding region of PD-L1 mRNA, antisense nucleic acids should be at least six nucleotides in length, and are preferably oligonucleotides ranging from 6 to about 50 nucleotides in length. In specific embodiments the oligonucleotide is at least 10 nucleotides, at least 17 nucleotides, at least 25 nucleotides or at least 50 nucleotides.

In one embodiment, the PD-L1 antisense nucleic acid is produced intracellularly by transcription from an exogenous sequence. For example, a vector or a portion thereof, is transcribed, producing an antisense nucleic acid (RNA) of the PD-L1 gene. Such a vector would contain a sequence encoding the PD-L1 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding PD-L1, or fragments thereof, can be by any promoter known in the art to act in vertebrate, preferably human cells. Such promoters can be inducible or constitutive. Such promoters include, but are not limited to, the SV40 early promoter region (Bernoist and Chambon, *Nature* 29:304-310 (1981), the promoter contained in the 3' long terminal repeat of Rous sarcoma virus (Yamamoto et al., *Cell* 22:787-797 (1980), the herpes thymidine promoter (Wagner et al., *Proc. Natl. Acad. Sci. U.S.A.* 78:1441-1445 (1981), the regulatory sequences of the metallothionein gene (Brinster, et al., *Nature* 296:39-42 (1982)), etc.

F. Antibody and Binding Polypeptide Variants

In certain embodiments, amino acid sequence variants of the antibodies and/or the binding polypeptides provided herein are contemplated. For example, it may be desirable to improve the binding affinity and/or other biological properties of the antibody and/or binding polypeptide. Amino acid sequence variants of an antibody and/or binding polypeptides may be prepared by introducing appropriate modifications into the nucleotide sequence encoding the antibody and/or binding polypeptide, or by peptide synthesis. Such modifications include, for example, deletions from, and/or insertions into and/or substitutions of residues within the amino acid sequences of the antibody and/or binding polypeptide. Any combination of deletion, insertion, and substitution can be made to arrive at the final construct, provided that the final construct possesses the desired characteristics, e.g., target-binding.

In certain embodiments, antibody variants and/or binding polypeptide variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody and/or binding polypeptide of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of the antibody and/or the binding polypeptide that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact Points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

G. Antibody and Binding Polypeptide Derivatives

In certain embodiments, an antibody and/or binding polypeptide provided herein may be further modified to contain additional nonproteinaceous moieties that are known in the art and readily available. The moieties suitable for derivatization of the antibody and/or binding polypeptide include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody and/or binding polypeptide may vary, and if more than one polymer are attached, they can be the same or different molecules. In general, the number and/or type of polymers used for derivatization can be determined based on considerations including, but not limited to, the particular properties or functions of the antibody and/or binding polypeptide to be improved, whether the antibody derivative and/or binding polypeptide derivative will be used in a therapy under defined conditions, etc.

In another embodiment, conjugates of an antibody and/or binding polypeptide to nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody and/or binding polypeptide-nonproteinaceous moiety are killed.

In some embodiments, the sample is a tissue sample. In some embodiments, the sample is a tumor tissue sample. In some embodiments, the tumor tissue sample comprises tumor cells, tumor infiltrating immune cells, intratumoral immune cells, peritumoral immune cells or any combinations thereof, tumor stroma cells (e.g. fibroblasts). In some embodiments, the sample is of a patient's cancer. In some embodiments, the sample is obtained prior to treatment with a PD-L1 axis binding antagonist. In some embodiments, the sample is formalin fixed and paraffin embedded.

In some embodiments, the disease or disorder is a proliferative disease or disorder. In some embodiments, the disease or disorder is an immune-related disease or disorder. In some embodiments, the disease or disorder is cancer. In some embodiments, the cancer is non-small cell lung cancer, renal cell cancer, ovarian cancer, pancreatic cancer, gastric carcinoma, bladder cancer, esophageal cancer, mesothelioma, melanoma, breast cancer, thyroid cancer, colorectal cancer, head and neck cancer, osteosarcoma, prostate cancer, or glioblastoma. In some embodiments, the cancer is non-small cell lung cancer (NSCLC). In some embodiments, the NSCLC is second-line or third-line locally advanced or metastatic NSCLC. In some embodiments, the NSCLC is adenocarcinoma. In some embodiments, the NSCLC is squamous cell carcinoma.

In some embodiments of any of the methods, the individual according to any of the above embodiments may be a human.

In a further embodiment, provided herein are methods for treating a cancer. In one embodiment, the method comprises administering to an individual having such cancer an effective amount of a PD-L1 axis binding antagonist. In one such embodiment, the method further comprises administering to the individual an effective amount of at least one additional therapeutic agent. In some embodiments, the individual may be a human.

PD-L1 axis binding antagonist described herein can be used either alone or in combination with other agents in a therapy. For instance, a PD-L1 axis binding antagonist described herein may be co-administered with at least one additional therapeutic agent. In certain embodiments, an additional therapeutic agent is a chemotherapeutic agent.

Such combination therapies noted above encompass combined administration (where two or more therapeutic agents are included in the same or separate formulations), and separate administration, in which case, administration of the antagonist can occur prior to, simultaneously, and/or following, administration of the additional therapeutic agent and/or adjuvant. PD-L1 axis binding antagonist described herein can also be used in combination with radiation therapy.

A PD-L1 axis binding antagonist (e.g., an antibody, binding polypeptide, and/or small molecule) described herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

PD-L1 axis binding antagonists (e.g., an antibody, binding polypeptide, and/or small molecule) described herein may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The PD-L1 axis antagonist need not be, but is optionally formulated with one or more agents currently used to prevent or treat the disorder in question. The effective amount of such other agents depends on the amount of the PD-L1 axis binding antagonist present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a PD-L1 axis binding antagonist described herein (when used alone or in combination with one or more other additional therapeutic agents) will depend on the type of disease to be treated, the severity and course of the disease, whether the PD-L1 axis binding antagonist is administered for preventive or therapeutic purposes, previous therapy, the patient's clinical history and response to the PD-L1 axis binding antagonist, and the discretion of the attending physician. The PD-L1 axis binding antagonist is suitably administered to the patient at one time or over a series of treatments. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g., every week or every three weeks (e.g., such that the patient receives from about two to about twenty, or e.g., about six doses of the PD-L1 axis binding antagonist). An initial higher loading dose, followed by one or more lower doses may be administered. An exemplary dosing regimen comprises administering. However, other dosage regimens may be useful. The progress of this therapy is easily monitored by conventional techniques and assays.

In some embodiments of any of the methods, the PD-L1 axis binding antagonist (e.g., anti-PD-L1 antibody) is administered at a dosage of about 0.3-30 mg/kg. In some embodiments, the PD-L1 axis binding antagonist (e.g., anti-PD-L1 antibody) is administered at a dosage of about any of 0.3 mg/kg, 0.5 mg/kg, 1 mg/kg, 2 mg/kg, 4 mg/kg, 8 mg/kg, 15 mg/kg, 20 mg/kg, or 30 mg/kg. In some embodiments, the PD-L1 axis binding antagonist (e.g., anti-PD-L1 antibody) is administered at a dosage of about any of 2 mg/kg, 4 mg/kg, 8 mg/kg, 15 mg/kg, or 30 mg/kg in 21-day cycles. It is understood that any of the above formulations or therapeutic methods may be carried out using an immunoconjugate in place of or in addition to the PD-L1 axis binding antagonist.

Pharmaceutical formulations of a PD-L1 axis binding antagonist as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. In some embodiments, the PD-L1 axis binding antagonist is a binding small molecule, an antibody, binding polypeptide, and/or polynucleotide. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one embodiment, a sHASEGP is combined with one or more additional glycosaminoglycanases such as chondroitinases.

Exemplary lyophilized formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacy-late) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semiper-meable matrices of solid hydrophobic polymers containing the PD-L1 axis binding antagonist, which matrices are in the form of shaped articles, e.g., films, or microcapsules.

The formulations to be used for in vivo administration are generally sterile. Sterility may be readily accomplished, e.g., by filtration through sterile filtration membranes.

It is understood that any of the above articles of manu-facture may include an immunoconjugate described herein in place of or in addition to a PD-L1 antagonist.

Identifying and Methods of Using Biomarkers

Provided herein are methods for identifying treatment-responsive biomarkers.

In some embodiments, pharmacodynamics biomarkers can be identified based on a correlation or the defined relationship between analyte expression levels and positive or negative changes in a subject's response relative to one or more pre-treatment baseline response. In some embodi-ments, analyte expression levels can be measured in samples collected from a subject prior to, during and following treatment or therapeutic intervention.

Pharmacodynamic biomarkers can be used for, without limitation, treatment monitoring and assessing treatment effectiveness. For example, pharmacodynamics biomarker levels can be provided to a clinician for use in establishing or altering a course of treatment for a subject. When a treatment is selected and treatment starts, the subject can be monitored periodically by collecting biological samples at two or more intervals, determining a clinical response cor-responding to a given time interval pre-, during, and post-treatment, and comparing clinical response over time. On the basis of these responses and any trends observed with respect to increasing, decreasing or stabilizing clinical responses or changes in pharmacodynamics biomarker lev-els, a clinician, therapist, or other health-care professional may choose to continue treatment as is, to discontinue treatment, or to adjust the treatment plan with the goal of seeing improvement over time.

Accordingly, provided herein are methods for assessing a treatment response of an individual with a PD-L1 axis binding antagonist, the method comprising: (a) determining the level(s) of one or more biomarkers in a biological sample derived from the individual at a time point during or after administration of the PD-L1 axis binding antagonist; and (b) maintaining, adjusting, or stopping the treatment of the individual based on a comparison of the level(s) of one or more biomarkers in the biological sample with reference levels, wherein a change in the level(s) of one or more biomarkers in the biological sample compared to the refer-ence levels is indicative of a response to treatment with the PD-L1 axis binding antagonist.

Further provided herein are methods for monitoring the response of an individual treated with a PD-L1 axis binding antagonist, said method comprising: (a) determining the level(s) of one or more biomarkers in a biological sample derived from the individual at a time point during or after administration of the PD-L1 axis binding antagonist; and (b) comparing the level(s) of one or more biomarkers in the biological sample with reference levels in order to monitor the response in the individuals undergoing treatment with the PD-L1 axis binding antagonist.

In some embodiments, the reference levels of the one or more biomarkers is selected from the group consisting of (1) the level of the one or more biomarkers from the individual prior to administration of the PD-L1 axis binding antagonist; (2) the level of the one or more biomarkers from a reference population; (3) a pre-assigned level for the one or more biomarkers; and (4) the level of the one or more biomarkers from the individual at a second time point prior to the first time point.

To correlate and compare an individual's biological sample with a reference population, it is necessary to obtain data on the clinical responses exhibited by a population of individuals who received the treatment, i.e., a clinical popu-lation, before and/or after treatment with the PD-L1 axis binding antagonist. This clinical data may be obtained by retrospective analysis of the results of a clinical trial(s). Alternatively, the clinical data may be obtained by designing and carrying out one or more new clinical trials. The analysis of clinical population data is useful to define a standard reference population which, in turn, is useful to classify subjects for selection of therapeutic treatment, and/or to classify subjects as exhibiting a positive response to treat-ment with a PD-L1 axis binding antagonist.

In some embodiments, the change in the level(s) of one or more biomarkers in the biological sample compared to the reference levels is an increase in the levels.

In some embodiments, the change in the level(s) of one or more biomarkers in the biological sample compared to the reference levels is a decrease in the levels.

In some embodiments, the one or more biomarkers is selected from the group consisting of PD-L1, PD-1, PD-L2 and any combinations thereof. In some embodiments, an increase in one or more biomarkers selected from the group consisting of PD-L1, PD-1, PD-L2 and any combinations thereof in the biological sample compared to the reference levels is indicative of a positive response to treatment.

In some embodiments, the one or more biomarkers is an immune related marker.

In some embodiments, the one or more biomarkers is a T-cell related marker.

In some embodiments, the one or more biomarkers is a T-cell activation marker.

In some embodiments, the T-cell activation marker is increased in the biological sample compared to the reference levels.

In some embodiments, the T-cell activation marker is selected from the group consisting of an CD8, IFN-g, Granzyme-A, TNF-a, perforin and any combinations thereof. In some embodiments, an increase in the T-cell activation marker selected from the group consisting of CD8, IFN-g, Granzyme-A, TNF-a, perforin and any com-binations thereof in the biological sample compared to the reference levels is indicative of a positive response to treatment.

In some embodiments, the one or more biomarkers is an activated proliferating T cell.

In some embodiments, the activated proliferating T cell is increased in the biological sample compared to the reference levels.

In some embodiments, the activated proliferating T cell is a CD8+/Ki67+ cell, CD8+/HLA-DR+/Ki67+ cell and any combinations thereof.

In some embodiments, the one or more biomarkers is IL-6.

In some embodiments, the IL-6 level is decreased in the biological sample compared to the reference levels. In some embodiments, a decrease in the IL-6 level in the biological sample compared to the reference levels is indicative of a positive response to treatment. In some embodiments, the IL-6 level is increased in the biological sample compared to the reference levels. In some embodiments, an increase in the IL-6 level in the biological sample compared to the reference levels indicates that there is no response to treatment.

In some embodiments, the biological sample derived from the individual is selected from the group consisting of a cell, a tissue, a tissue culture, a tumor, a biological fluid and combinations thereof.

In some embodiments, the biological fluid is selected from the group consisting of plasma, serum, whole blood, PBMCs and combinations thereof.

In some embodiments, the tissue is a tumor tissue.

In some embodiments, the tumor tissue is selected from the group consisting of tumor cells, tumor infiltrating cells, stromal cells and any combinations thereof.

In some embodiments, the cell is a circulating tumor cell (CTC).

In some embodiments, the individual suffers from a proliferative disease or disorder.

In some embodiments, the individual suffers from cancer or malignancy.

In some embodiments, the cancer or malignancy is selected from non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, merkel cell cancer, and other hematologic malignancies.

In some embodiments, the individual suffers from an immune-related disease or disorder.

In some embodiments, the PD-L1 axis binding antagonist is a PD-L1 binding antagonist.

In some embodiments, the PD-L1 binding antagonist inhibits the binding of PD-L1 to its ligand binding partners.

In some embodiments, the PD-L1 binding antagonist inhibits the binding of PD-L1 to PD-1.

In some embodiments, the PD-L1 binding antagonist inhibits the binding of PD-L1 to B7-1.

In some embodiments, the PD-L1 binding antagonist inhibits the binding of PD-L1 to both PD-1 and B7-1.

In some embodiments, the PD-L1 binding antagonist is an antibody.

In some embodiments, the antibody is a monoclonal antibody.

In some embodiments, the antibody is a human, humanized or chimeric antibody.

In some embodiments, the PD-L1 axis binding antagonist is a PD-1 binding antagonist.

In some embodiments, the PD-1 binding antagonist inhibits the binding of PD-1 to its ligand binding partners.

In some embodiments, the PD-1 binding antagonist inhibits the binding of PD-1 to PD-L1.

In some embodiments, the PD-1 binding antagonist inhibits the binding of PD-1 to PD-L2.

66

In some embodiments, the PD-1 binding antagonist inhibits the binding of PD-1 to both PD-L1 and PD-L2.

In some embodiments, the PD-1 binding antagonist is an antibody.

In some embodiments, the antibody is a monoclonal antibody.

In some embodiments, the antibody is a human, humanized or chimeric antibody.

Methods of Advertising

Further provided herein are methods for advertising a PD-L1 axis binding antagonist comprising promoting, to a target audience, the use of the PD-L1 axis binding antagonist for treating an individual with a disease or disorder based on presence and/or levels of a PD-L1 biomarker. In some embodiments, the use of the PD-L1 axis binding antagonist is based upon elevated levels of the PD-L1 biomarker.

Advertising is generally paid communication through a non-personal medium in which the sponsor is identified and the message is controlled. Advertising for purposes herein includes publicity, public relations, product placement, sponsorship, underwriting, and sales promotion. This term also includes sponsored informational public notices appearing in any of the print communications media designed to appeal to a mass audience to persuade, inform, promote, motivate, or otherwise modify behavior toward a favorable pattern of purchasing, supporting, or approving the invention herein.

The advertising and promotion of the diagnostic method herein may be accomplished by any means. Examples of advertising media used to deliver these messages include television, radio, movies, magazines, newspapers, the internet, and billboards, including commercials, which are messages appearing in the broadcast media. Advertisements also include those on the seats of grocery carts, on the walls of an airport walkway, and on the sides of buses, or heard in telephone hold messages or in-store PA systems, or anywhere a visual or audible communication can be placed.

More specific examples of promotion or advertising means include television, radio, movies, the internet such as webcasts and webinars, interactive computer networks intended to reach simultaneous users, fixed or electronic billboards and other public signs, posters, traditional or electronic literature such as magazines and newspapers, other media outlets, presentations or individual contacts by, e.g., e-mail, phone, instant message, postal, courier, mass, or carrier mail, in-person visits, etc.

The type of advertising used will depend on many factors, for example, on the nature of the target audience to be reached, e.g., hospitals, insurance companies, clinics, doctors, nurses, and patients, as well as cost considerations and the relevant jurisdictional laws and regulations governing advertising of medicaments and diagnostics. The advertising may be individualized or customized based on user characterizations defined by service interaction and/or other data such as user demographics and geographical location.

Diagnostic Kits, Assays and Articles of Manufacture

Provided herein are diagnostic kit comprising one or more reagent for determining the presence of a PD-L1 biomarker in a sample from an individual with a disease or disorder, wherein the presence of a PD-L1 biomarker means a higher likelihood of efficacy when the individual is treated with a PD-L1 axis binding antagonist, and wherein the absence of a PD-L1 biomarker means a less likelihood of efficacy when the individual with the disease is treated with the PD-L1 axis binding antagonist. Optionally, the kit further comprises instructions to use the kit to select a medicament (e.g. a PD-L1 axis binding antagonist, such as an anti-PD-L1 antibody) for treating the disease or disorder if the individual expresses the PD-L1 biomarker. In another embodiment, the instructions are to use the kit to select a medicament other than PD-L1 axis binding antagonist if the individual does not express the PD-L1 biomarker.

Provided herein are also assay for identifying an individual with a disease or disorder to receive a PD-L1 axis binding antagonist, the method comprising: determining the presence of a PD-L1 biomarker in a sample from the individual, and recommending a PD-L1 axis binding antagonist based on the presence of a PD-L1 biomarker.

Provided herein are also articles of manufacture comprising, packaged together, a PD-L1 axis binding antagonist (e.g., anti-PD-L1 antibodies) in a pharmaceutically acceptable carrier and a package insert indicating that the PD-L1 axis binding antagonist (e.g., anti-PD-L1 antibodies) is for treating a patient with a disease or disorder based on expression of a PD-L1 biomarker. Treatment methods include any of the treatment methods disclosed herein. Further provided are the invention concerns a method for manufacturing an article of manufacture comprising combining in a package a pharmaceutical composition comprising a PD-L1 axis binding antagonist (e.g., anti-PD-L1 antibodies) and a package insert indicating that the pharmaceutical composition is for treating a patient with a disease or disorder based on expression of PD-L1 biomarker.

The article of manufacture comprises a container and a label or package insert on or associated with the container. Suitable containers include, for example, bottles, vials, syringes, etc. The containers may be formed from a variety of materials such as glass or plastic. The container holds or contains a composition comprising the cancer medicament as the active agent and may have a sterile access port (for example the container may be an intravenous solution bag or a vial having a stopper pierceable by a hypodermic injection needle).

The article of manufacture may further comprise a second container comprising a pharmaceutically-acceptable diluent buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

The article of manufacture of the present invention also includes information, for example in the form of a package insert, indicating that the composition is used for treating cancer based on expression level of the biomarker(s) herein. The insert or label may take any form, such as paper or on electronic media such as a magnetically recorded medium (e.g., floppy disk) or a CD-ROM. The label or insert may also include other information concerning the pharmaceutical compositions and dosage forms in the kit or article of manufacture.

The invention also concerns a method for manufacturing an article of manufacture comprising combining in a package a pharmaceutical composition comprising a PD-L1 axis binding antagonist (e.g., an anti-PD-L1 antibody) and a package insert indicating that the pharmaceutical composition is for treating a patient with cancer (such as NSCLC) based on expression of a PD-L1 biomarker.

The article of manufacture may further comprise an additional container comprising a pharmaceutically acceptable diluent buffer, such as bacteriostatic water for injection (BWFI), phosphate-buffered saline, Ringer's solution, and/or dextrose solution. The article of manufacture may further include other materials desirable from a commercial and user standpoint, including other buffers, diluents, filters, needles, and syringes.

EXAMPLES

The following are examples of methods and compositions. It is understood that various other embodiments may be practiced, given the general description provided above.

Materials and Methods for Examples

Samples: Formalin-fixed paraffin-embedded (FFPE) sections of a tumor sample or cancer cell line were analyzed.

Immunohistochemistry (IHC): Formalin-fixed, paraffin-embedded tissue sections were deparaffinized prior to antigen retrieval, blocking and incubation with primary anti-PD-L1 antibodies. Following incubation with secondary antibody and enzymatic color development, sections were counterstained and dehydrated in series of alcohols and xylenes before coverslipping.

The following protocol was used for IHC. The Ventana Benchmark XT or Benchmark Ultra system was used to perform PD-L1IHC staining using the following reagents and materials:

Primary antibody: anti-PD-L1 Rabbit Monoclonal Primary Antibody

Specimen Type: Formalin-fixed paraffin embedded (FFPE) section of tissue samples and control cell pellets of varying staining intensities Procedure Species: Human Instrument: BenchMark XT or Benchmark Ultra Epitope Recovery Conditions: Cell Conditioning, standard 1 (CC1, Ventana, cat #950-124)

Primary Antibody Conditions: 1/100, 6.5 µg/ml/16 minutes at 36° C.

Diluent: Antibody dilution buffer (Tris-buffered saline containing carrier protein and Brig-35)

Negative control: Naive Rabbit IgG at 6.5 µg/ml (Cell Signaling) or diluent alone Detection: Optiview or Ultraview Universal DAB Detection kit (Ventana), and amplification kit (if applicable) were used according to manufacturer's instructions (Ventana).

Counterstain: Ventana Hematoxylin II (cat #790-2208)/ with Bluing reagent (Cat #760-2037) (4 minutes and 4 minutes, respectively)

The Benchmark Protocol was as follows:

1. paraffin (Selected)
2. Deparaffinization (Selected)
3. Cell Conditioning (Selected)
4. Conditioner #1 (Selected)
5. Standard CC1(Selected)
6. Ab Incubation Temperatures (Selected)
7. 36C Ab Inc. (Selected)
8. Titration (Selected)
9. Auto-dispense (Primary Antibody), and Incubate for (16 minutes)
10. Countstain (Selected)
11. Apply One Drop of (Hematoxylin II) (Countstain), Apply Coverslip, and Incubate for (4 minutes)
12. Post Counterstain (Selected)
13. Apply One Drop of (BLUING REAGENT) (Post Countstain), Apply Coverslip, and Incubate for (4 minutes)
14. Wash slides in soap water to remove oil
15. Rinse slides with water 16. Dehydrate slides through 95% Ethanol, 100% Ethanol to xylene (Leica autostainer program #9)

17. Cover slip.

Example 1—Scoring PD-L1 Expression by IHC

The presence or absence of PD-L1 expression in tumor specimens was evaluated using anti-PD-L1-specific antibody that can detect PD-L1 in human formalin-fixed, paraffin-embedded (FFPE) tissues by IHC. To measure and quantify relative expression of PD-L1 in tumor samples, a PD-L1 IHC scoring system was developed to measure PD-L1 specific signal in tumor cells and tumor infiltrating immune cells. Immune cells are defined as cells with lymphoid and/or macrophage/histiocyte morphology.

Tumor cell staining is expressed as the percent of all tumor cells showing membranous staining of any intensity. Infiltrating immune cell staining is defined as the percent of the total tumor area occupied by immune cells that show staining of any intensity. The total tumor area encompasses the malignant cells as well as tumor-associated stroma, including areas of immune infiltrates immediately adjacent to and contiguous with the main tumor mass. In addition, infiltrating immune cell staining is defined as the percent of all tumor infiltrating immune cells.

There was a wide dynamic range of PD-L1 staining intensities in tumor tissues. Irrespective of subcellular localization, the signal was also classified as strong, moderate, weak, or negative staining.

Figure 2:
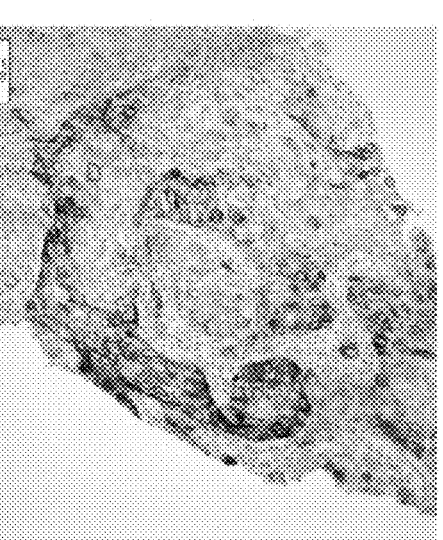
FIG. 2 shows exemplary PD-L1 positive IHC staining of tumor samples from (A) Triple-Negative Breast Cancer; (B) Malignant Melanoma; (C) NSCLC, adenocarcinoma.

As shown in FIG. 1, negative signal intensity is characterized by an absence of any detectable signal, as illustrated using HEK-293 cells. In contrast, positive signal intensity is characterized by a golden to dark brown, membrane staining, as illustrated using HEK-293 cells transfected with recombinant human PD-L1. Finally, positive signal intensity is also illustrated by staining of placental trophoblasts and strong staining in the area of tonsilar crypts and often in membranous pattern that is characterized by a golden to dark brown staining. In tumor tissues, PD-L1 negative samples are qualified as having no detectable signal or only weak cytoplasmic background staining when evaluated using a 20× objective. In contrast, PD-L1 positive samples demonstrate primarily membranous staining in tumor cells and/or infiltrating immune cells. PD-L1 staining is observed with variable intensity from weak with fine, light-brown membranes to strong with dark-brown thick membranes easily recognized at low magnification. As illustrated in FIG. 2, three representative PD-L1 positive tumor samples are shown: (A) Triple-Negative Breast Cancer, in which most tumor cells are strongly positive for PD-L1 showing a combination of membranous and cytoplasmic staining (100× magnification); (B) Malignant Melanoma, in which a cluster of immune cells, some of them with membranous staining for PD-L1, is shown; rare tumor cells (arrows) with membranous staining for PD-L1 (400× magnification); (C) NSCLC, adenocarcinoma, in which a cluster of immune cells with strong staining for PD-L1 is shown; several tumor cells (arrows) with membranous and/or cytoplasmic staining for PD-L1 (400× magnification).

The staining in positive cases tends to be focal with respect to spatial distribution and intensity. The percentages of tumor or immune cells showing staining of any intensity were visually estimated and used to determine PD-L1 status. An isotype negative control was used to evaluate the presence of background in test samples.

Staining required one serial tissue section for H&E, a second serial tissue section for anti-PD-L1, and a third serial tissue section for the isotype negative control. The PD-L1-transfected HEK-293 cell line control or tonsil slides were used as run controls and a reference for assay specificity.

| PDL-1 Status Criteria | |
| --- | --- |
| PD-L1 Status | Staining criteria |
| Negative | 0% membrane staining or cytoplasmic staining or combinations of both at ANY staining intensity |
| Positive | >0% membrane staining or cytoplasmic staining or combinations of both at ANY staining intensity $\geq$1% membrane staining or cytoplasmic staining or combinations of both at ANY staining intensity $\geq$5% membrane staining or cytoplasmic staining or combinations of both at ANY staining intensity $\geq$10% membrane staining or cytoplasmic staining or combinations of both at ANY staining intensity |

In some cases, the PD-L1 positive status may comprise the presence of discernible PD-L1 staining of any intensity in either tumor cells or tumor infiltrating immune cells in up to 50% of tumor area occupied by tumor cells, associated intratumoral, and contiguous peri-tumoral desmoplastic stroma. Thus, PD-L1 positive staining includes as high as 50% of tumor cells or tumor infiltrating immune cells showing staining of any intensity.

Evaluable slides stained with anti-PD-L1 were evaluated as described above. Negative staining intensity was characterized by an absence of any detectable signal or a signal that was characterized as pale gray to blue (rather than brown or tan) and absence of membrane enhancement. The case was negative if there were no (e.g., absent) membrane staining.

Example 2—Treatment Using Anti-PD-L1 Antibody

A Phase I study design specifically evaluated the correlation between PD-L1 tumor status as assessed by (a) an Anti-PD-L1 IHC reagent (b) PD-L1 gene expression as measured by a PD-L1 qPCR reagent (c) Immune gene signature as measured by a multiplex qPCR "immunochip" and clinical benefit of monotherapy inhibition of the PD-L1/PD-1 pathway as measured by (i) RECIST 1.1 based responses (ii) immune-related Response Criteria (iii) PFS (iv) OS (v) complete response rate (vi) durability of response (vii) PD at 6 weeks. Patients in the expansion cohorts were required to provide tumor tissue for assessment of PD-L1 tumor status, and were enrolled into either expansion cohorts either regardless of PD-L1 tumor status, or enrolled into expansion cohorts which prospectively selected patients based on PD-L1 tumor status as measured by an IHC assay for PD-L1. Tumor types enrolled specifically included NSCLC (squamous and non-squamous histology), melanoma, RCC, CRC, gastric cancer, breast cancer, SCCHN, pancreatic cancer, bladder cancer and hematologic malignancies. Additionally, patients with lymphoma, myeloma, sarcoma, ovarian cancer, prostate cancer, esophageal cancer, small cell lung cancer, mycoses fungoides, merkel cell cancer, cervical cancer, HPV or EBV+ SCCHN, and thymic carcinoma are/have also been enrolled.

In addition to assessing the correlation with baseline PD-L1 tumor status with clinical benefit from monotherapy inhibition of the PD-L1/PD-1 pathway, the study also evaluated the benefit of: (a) Measuring PD-L1 status in archival tumor samples vs fresh or recent tumor biopsy samples (b) evaluating CD8+ T cell infiltration in tumors with an anti- CD8 IHC reagent (c) evaluating PD-L1 staining in different cell types %, compartments or strength of staining (d) impact of peritumoral vs intratumoral staining of PD-L1 or CD8 (e) impact of amplification of PD-L1 staining (f) impact of macrodissection of tumor prior to qPCR or immunochip assessment (g) impact of tissue sample age and fixation on PD-L1 status assessment and correlation with benefit (h) value of on-treatment tumor biopsy for assessing clinical benefit or toxicity using the above described tumor characterization methods (i) value of FDG PET imaging and CT contrast enhancement for assessing on-treatment benefit or for patient selection (j) value of tumor mutational/oncogene status (e.g., KRAS, bRAF, PI3K pathway mutation status, Met status, Her2neu status, PTEN status) in predicting benefit for the above treatment (k) CTC number and PD-L1 characterization (1) circulating cell type, subset and number (m) circulating plasma/serum biomarkers (n) ethnic differences (o) smoking status (p) FcgRIII polymorphism status (q) immune-related polymorphism status.

Study design. This study was a Phase I multicenter trial designed to evaluate the preliminary activity and safety of treatment with PD-L1/PD-1 pathway inhibition using an anti-PD-L1 antibody (MPDL3280A) in solid and liquid tumors. Over 250 patients were enrolled across more than 17 multinational sites. Treatment with MPDL3280A was continued until progression of disease, unacceptable toxicity depending on clinical status of the patient (i.e., patients with evidence of disease progression were allowed to continue on study treatment if they maintained their ECOG PS and there was potential for clinical benefit as assessed by the investigator. An interim analysis of data from this study was performed at multiple times after initiation of the study, including on Jan. 10, 2013, for patients enrolled on study, including patients that were enrolled prior to Jul. 1, 2012 (n=122). This data suggests that patients whose tumors expressed lower levels of PD-L1 did derive minimal benefit from PD-L1/PD-1 pathway inhibition but that patients that had higher levels of PD-L1 in their tumor, particularly as measured on tumor immune infiltrating cells, derived the majority of benefit, as measured by durable responses, on study.

During the study, data on tumor measurement and survival status were collected for evaluation of PFS, overall survival (OS) and overall response rate (ORR) and other measures as noted above. CT scans were obtained at baseline and approximately every 6 weeks. Imaging in some patients included FDG-PET imaging. Blood biomarkers were assessed at baseline and on study for blood based and cell subset based biomarkers. Correlating these and other tumor biomarkers with clinical outcomes will assist in identifying predictive biomarkers, e.g., markers in circulation that may reflect drug activity or response to therapy. Blood for serum and plasma was drawn from consenting patients at pre-specified times and evaluated for levels of these exploratory markers.

Figure 3:
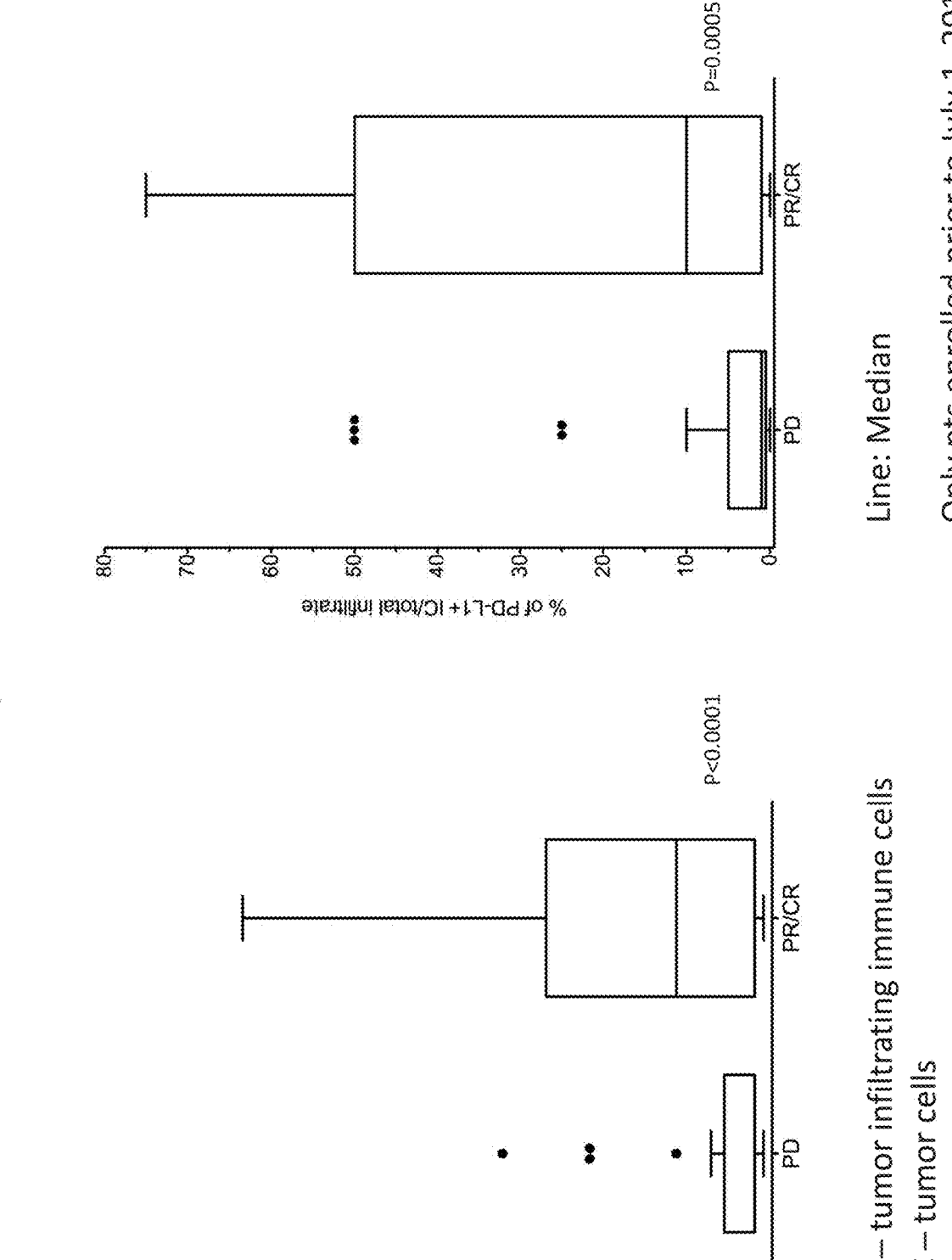
FIG. 3 shows the correlation of PD-L1 expression in tumor infiltrating immune cells with either PD or PR/CR response to anti-PD-L1 treatment in cancer patients. PD=progressive disease; PR=partial response; CR=complete response. (A) % of PD-L1+ tumor infiltrating immune cells within a tumor sample area, using PD-L1 IHC analysis. (B) % of PD-L1+IC within the total immune infiltrates within a tumor sample, using PD-L1 IHC analysis.

Example 3—Scoring by IHC of Samples from Individuals Treated with Anti-PD-L1 Antibody Shows Correlation Between PD-L1 Expression with Response to Treatment As illustrated in FIG. 3A, tumor samples were analyzed for PD-L1 expression from Phase I patients treated with the anti-PD-L1 antibody MPDL3280A. The data set includes patients enrolled prior to Jul. 1, 2012. Staining for PD-L1 status in tumor samples was performed using the IHC protocol described above.

The preliminary results show that there is a correlation between PD-L1 expression in tumor infiltrating cells (IC) and the patients' clinical response to anti-PD-L1 treatment. In particular, patients that displayed either a partial response (PR) or complete response (CR) to anti-PD-L1 treatment correlated with staining of PD-L1 expressing tumor infiltrating cells within the tumor sample area, as detected by IHC. The tumor sample area encompasses the malignant cells as well as tumor-associated stroma, including areas of immune infiltrates immediately adjacent to and contiguous with the main tumor mass. In contrast, tumors of patients that displayed no clinical response to anti-PD-L1 treatment (e.g., exhibiting progressive disease (PD)) exhibited lower PD-L1 expression in tumor infiltrating immune cells within the tumor sample area. $p<0.0001$.

A correlation between the patients' clinical response to anti-PD-L1 treatment and the staining of PD-L1 expressing tumor infiltrating immune cells (IC) within total immune cells was also observed. As shown in FIG. 3B, patients that exhibited responsiveness to treatment with anti-PD-L1 treatment correlated with staining of PD-L1 expressing tumor infiltrating cells within the total immune infiltrates within a tumor sample. The total number of immune infiltrates within a tumor sample was determined by H&E staining. Patients displayed either a partial response (PR) or complete response (CR) to anti-PD-L1 treatment correlated with staining of PD-L1 expressing tumor infiltrating cells within total immune infiltrates. In contrast, tumors of patients that displayed no clinical response to anti-PD-L1 treatment (e.g., exhibiting progressive disease (PD)) exhibited lower PD-L1 expression in tumor infiltrating immune cells within the tumor sample area. $p<0.0005$.

The preliminary data suggests that PD-L1 tumor status may be a predictive marker to identify patients who are more likely to respond to cancer therapy which involves inhibition of the PD-L1/PD-1 pathway using an anti-PD-L1 antibody treatment. The initial clinical benefit observed thus far includes PR and/or CR, but continued monitoring may reflect additional benefits including durability of response, evaluation of PFS, overall survival (OS) and overall response rate (ORR). This preliminary data provides support that PD-L1 expression in tumor samples, including expression on tumor infiltrating immune cells (IC), may predict responsiveness of a patient to cancer therapy which involves inhibition of the PD-L1/PD-1 pathway using an anti-PD-L1 antibody treatment. The data further supports that PD-L1 tumor status may determine likelihood that a patient will exhibit benefit from treatment with an anti-PD-L1 antibody.

Example 4—Scoring by qPCR of Samples from Individuals Treated with Anti-PD-L1 Antibody Shows Correlation Between PD-L1 Expression with Response to Treatment To evaluate whether PD-L1 gene expression status correlated with patient response to anti-PD-L1 treatment, the gene expression level of PD-L1 in tumor samples was determined by qPCR. Tissue from Phase 1 patients were macro-dissected to enrich for tumor content. RNA was isolated from the FFPE sections and PD-L1 gene expression was measured using PCR-based methodology (Fluidigm). PD-L1 expression was normalized to house-keeping gene (GusB).

FFPE RNA Isolation

H&E sides from FFPE tumor specimens were verified by a pathologist for tissue diagnostic and tumor content assessment. If overall tumor content was less than 70-75%, RNA was isolated from macro-dissected tissue to enrich for tumor content.

FFPE tissue section was deparaffinized using Envirene reagent (Hardy Diagnostics, Santa Maria, CA, USA) before tissue lysate was prepared. RNA isolation was performed using the LC Pertuzumab FFPET RNA kit (Roche Diagnostic part #06474 969 001). RNA concentration and 260/280 ratio was determined by NanoDrop® ND-2000/8000 UV-Vis Spectrophotometer. For each sample, 20 ng-200 ng RNA (2 µL in volume) was used for Gene expression analysis using the BioMark Real-Time PCR Platform (Immune Fluidigm panel). 110 ng-115 ng RNA was used for PDL1 qPCR assay.

PD-L1 qPCR Assay

PD-L1 qPCR was performed using PDL1 mRNA qRT-PCR assay developed by Roche Molecular Science (RMS). PDL1 and reference genes (GusB or TMEM55B) mRNA was reverse-transcribed, amplified and detected using reaction mix and Oligo Mix provided by RMS and according to the manufacturer instructions. The thermal cycling conditions were as follows: 1 cycle of 50° C. for 5 min, 1 cycle of 95° C. for 1 min, 1 cycle of 61° C. for 30 min, then 2 cycles of 95° C. for 15 sec and 61° C. for 30 sec, then 53 cycles of 92° C. for 15 sec and 61° C. for 30 sec, followed by 1 cycle of 40° C. for 30 sec and 25° C. for 10 sec. The reaction was performed in Cobas z480 Analyzer (Roche). PD-L1 expression levels were determined using the delta Ct (dCt) method as follows: Ct(PD-L1)-Ct(Reference Gene). The data set includes patients with samples available before Nov. 1, 2012.

Figure 4:
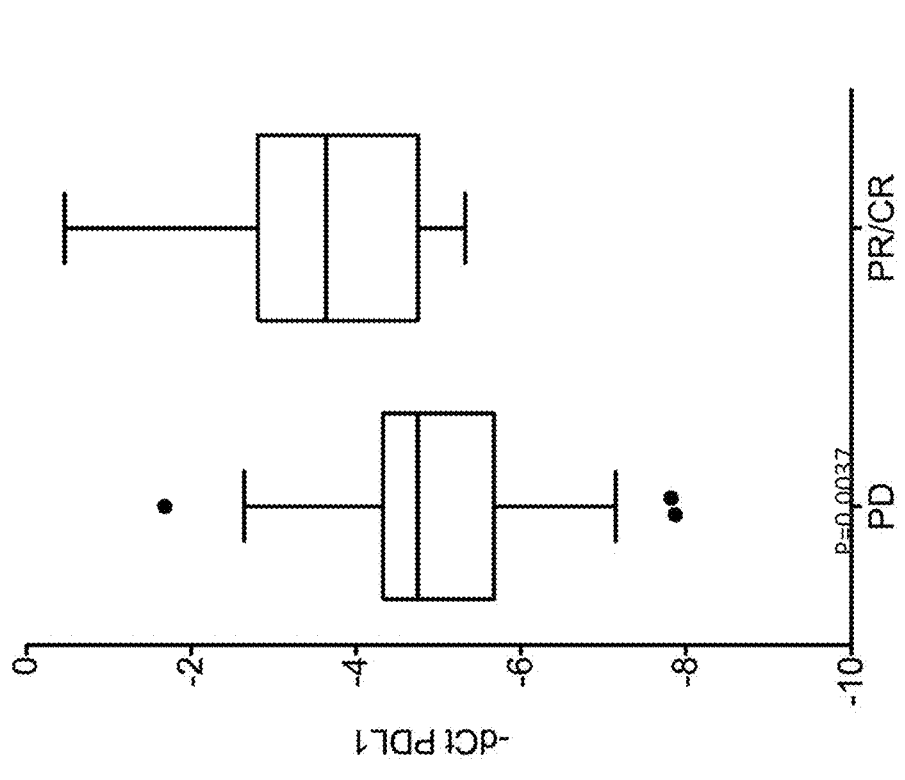
FIG. 4 shows the correlation of PD-L1 gene expression in tumor samples with either PD or PR/CR response to anti-PD-L1 treatment in cancer patients, using PD-L1 qPCR analysis. PD=progressive disease; PR=partial response; CR=complete response.

As illustrated in FIG. 4, the preliminary results show that there is a correlation between elevated PD-L1 gene expression in tumor samples and the patients' clinical response to anti-PD-L1 treatment. Patients that displayed either a partial response (PR) or complete response (CR) to anti-PD-L1 treatment correlated with PD-L1 gene expression within the tumor sample. In contrast, tumors of patients that displayed no clinical response to anti-PD-L1 treatment (e.g., displaying progressive disease (PD)) exhibited lower PD-L1 gene expression within the tumor sample. p=0.0037.

This preliminary data suggests that PD-L1 tumor gene expression status may be a useful biomarker to predict responsiveness of a patient to cancer therapy which involves inhibition of the PD-L1/PD-1 pathway using an anti-PD-L1 antibody. The PD-L1 tumor gene expression profile may be derived from the tumor cells, tumor infiltrating cells or a combination of both.

Figure 5:
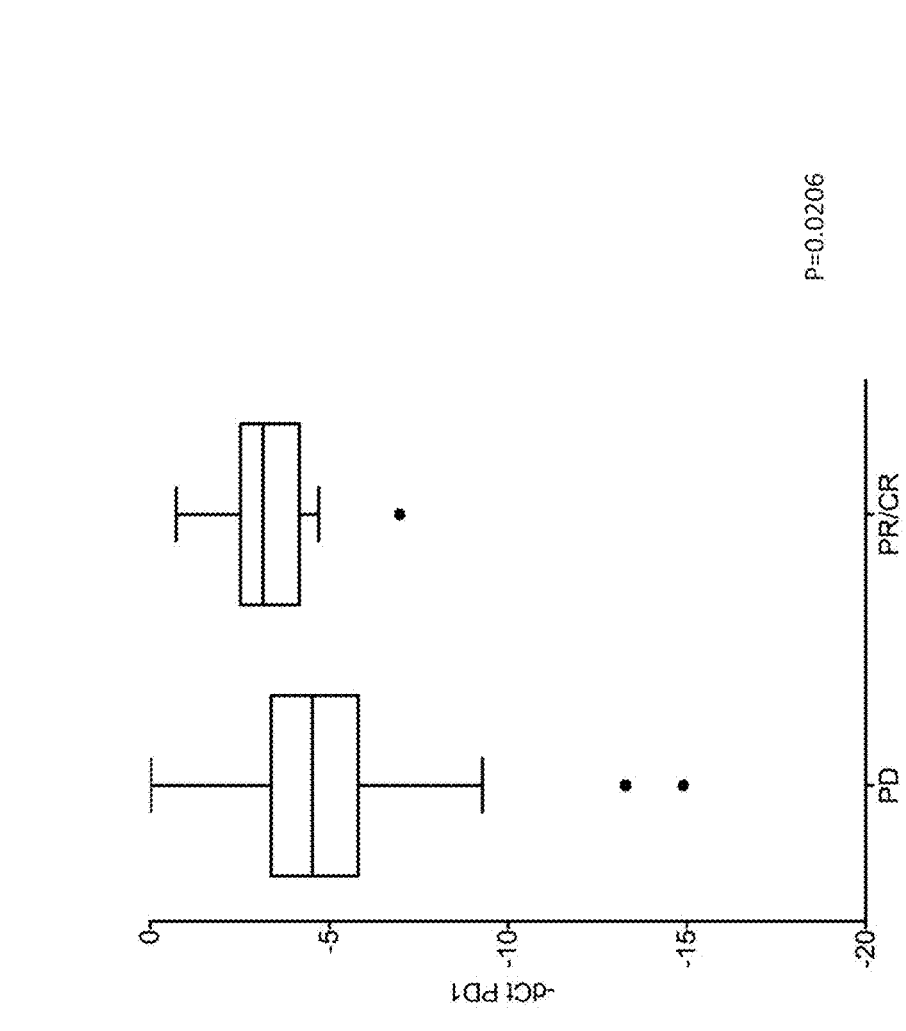
FIG. 5 shows the correlation of PD-1 gene expression in tumor samples with either PD or PR/CR response to anti-PD-L1 treatment in cancer patients. PD=progressive disease; PR=partial response; CR=complete response.

Example 5—Scoring by qPCR of Samples from Individuals Treated with Anti-PD-L1 Antibody Shows Correlation Between PD-1 Expression with Response to Treatment In addition to the correlation observed between PD-L1 gene expression in tumor samples and the patient clinical response, PD-1 gene expression status also shown to correlate with clinical response. As shown in FIG. 5, a correlation between PD-1 gene expression in tumor samples and the patients' clinical response to anti-PD-L1 treatment was observed. Patients that displayed a partial response (PR) to anti-PD-L1 treatment correlated with PD-1 gene expression within the tumor sample. In contrast, there was less correlation of PD-1 gene expression status with patients that displayed no clinical response to anti-PD-L1 treatment (e.g., PD). p=0.0206. The data set includes patients with samples available before Nov. 1, 2012.

This preliminary data suggests that PD-1 tumor status may be another predictive marker to identify patients who are more likely to respond to cancer therapy which involves inhibition of the PD-L1/PD-1 pathway using an anti-PD-L1 antibody treatment. PD-1 gene expression in tumor samples, including expression in tumor infiltrating immune cells (IC), tumor cells or a combination of the two, may predict responsiveness of a patient to cancer therapy which involves inhibition of the PD-L1/PD-1 pathway using an anti-PD-L1 antibody treatment.

This preliminary data suggests that PD-1 tumor status may be another predictive marker to identify patients who are more likely to respond to cancer therapy which involves inhibition of the PD-L1/PD-1 pathway using an anti-PD-L1 antibody treatment. PD-1 gene expression in tumor samples, including expression in tumor infiltrating immune cells (IC), tumor cells or a combination of the two, may predict responsiveness of a patient to cancer therapy which involves inhibition of the PD-L1/PD-1 pathway using an anti-PD-L1 antibody treatment.

Example 6—Tumor Immune Gene Signature of Samples from Individuals Treated with Anti-PD-L1 Antibody Shows Correlation with Response to Treatment To determine whether a correlation exists between certain immune gene signatures and a patients' responsive to treatment with anti-PD-L1 antibody, the following protocol was performed.

Fluidigm Gene Expression Analysis

Gene expression analysis was performed using the Bio-Mark Real-Time PCR Platform (Immune Fluidigm). 2 µl of total RNA was reverse-transcribed to cDNA and pre-amplified in a single reaction using Superscript III/Platinum Taq and 2× reaction mix (Invitrogen). 96 Taqman primer/probe sets were included in the pre-amplification reaction at a final dilution of 0.2× Taqman assay concentration (Applied Biosystems). The thermal cycling conditions were as follows: 1 cycle of 50° C. for 15 min, 1 cycle of 70° C. for 2 min, then 18 cycles of 95° C. for 15 sec and 60° C. for 4 min.

Pre-amplified cDNA was diluted 1.94-fold and then amplified using Taqman Universal PCR MasterMix (Applied Biosystems) on the BioMark BMK-M-96.96 platform (Fluidigm) according to the manufacturer's instructions. All samples were assayed in triplicate. All Taqman assays in the expression panel were FAM-MGB and ordered through Life Technologies either made-to-order or custom-designed, including five reference genes, GusB, SDHA, SP2, TMEM55B and VPS-33B. A median of the Ct values for the reference genes was calculated for each sample, and expression levels were determined using the delta Ct (dCt) method as follows: Ct(Target Gene)-Median Ct(Reference Genes). Alternatively, whenever indicated, the expression levels were determined after normalizing Ct values of each target gene to the median Ct value of all genes.

Figure 6:
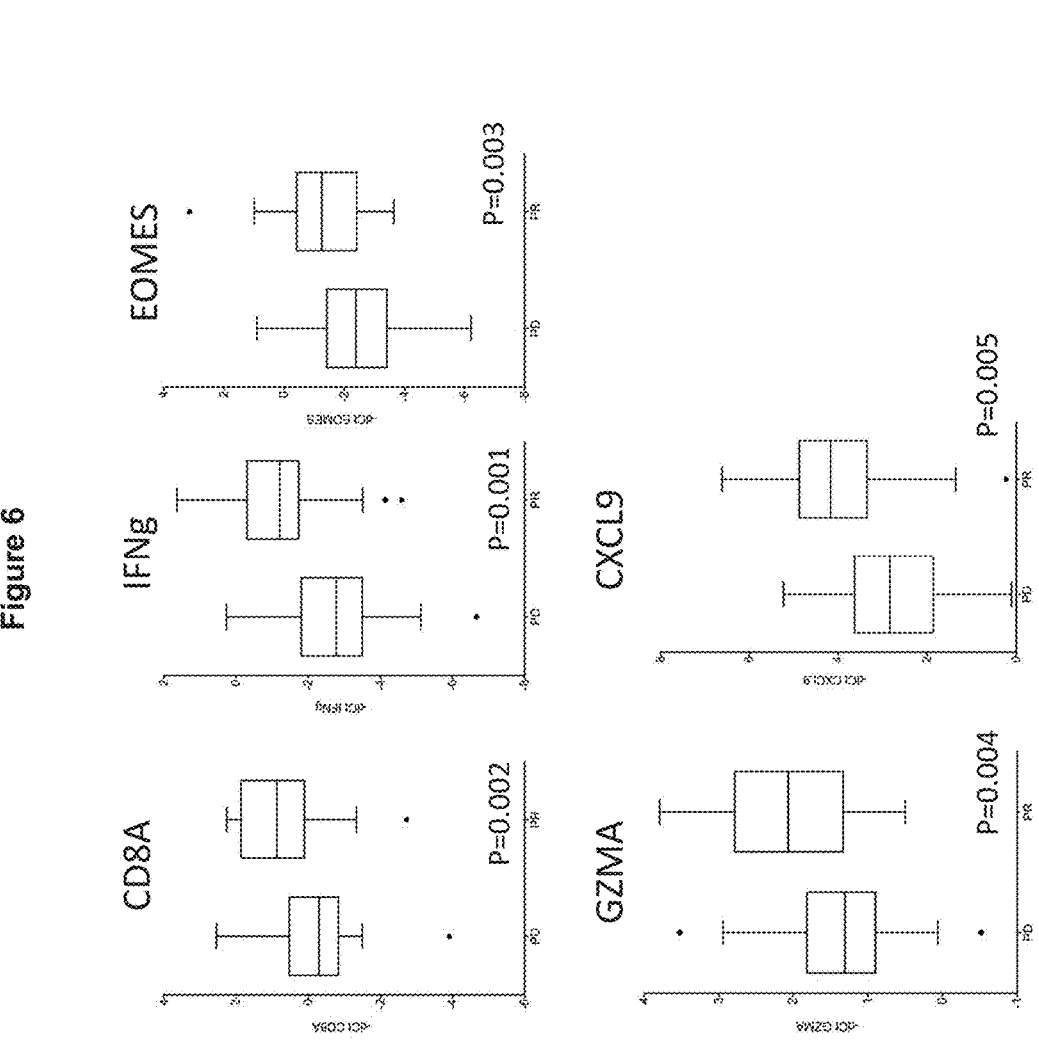
FIG. 6 shows the correlation of various immune gene expressions in tumor samples with either PD or PR response to anti-PD-L1 treatment in cancer patients. PD=progressive disease; PR=partial response.

As illustrated in FIG. 6, a correlation exists between certain immune gene signatures and the response of patients to treatment with anti-PD-L1 antibody. The results show that the expression of certain immune genes was correlated with patient response to treatment with anti-PD-L1 antibody. For example, the T cell activation immune genes, including IFN-g, CD8A, EOMES, Granzyme A and CXCL9, were found to correlate with patient partial response to treatment with anti-PD-L1. The data set includes patients with samples available before Nov. 1, 2012.

This preliminary data suggests that additional predictive biomarkers have been identified which may help to identify patients who are more likely to respond to cancer therapy which involves inhibition of the PD-L1/PD-1 pathway using an anti-PD-L1 antibody treatment. The immune gene signature includes, but is not limited to, IFN-g, CD8A, EOMES, Granzyme A and CXCL9, and is associated with immune cell activation.

Example 7—Correlation of PD-L1 and PD-L2 Expression with Response to Anti-PD-L1 Antibody Treatment Clinical activity, safety and biomarkers of patients with locally advanced or metastatic tumors treated with a PD-L1 axis binding antagonist, such as an anti-PD-L1 antibody.

PD-L1 and PD-L2 have been reported to regulate Th1 and Th2 immune responses. Tumor-expressed PD-L1, when bound to PD-1 or B7.1 on activated T cells, can mediate cancer immune evasion. Inhibiting the binding of PD-L1 to its receptors represents an attractive strategy to restore tumor-specific T-cell immunity. However, PD-L2 expressed in the tumor microenvironment may also bind PD-1-expressing T cells, dampening their function. MPDL3280A (anti-PD-L1 antibody), a human monoclonal antibody containing an engineered Fc-domain designed to promote a Th1-driven response to optimize efficacy and safety, is described here along with Phase I results.

Materials and Methods: A study was conducted with MPDL3280A administered IV q3w in patients with locally advanced or metastatic solid tumors, including 3+3 dose-escalation and expansion cohorts. ORR was assessed by RECIST v1.1 and includes u/cCR and u/cPR. PD-L1 was measured by IHC (pos vs. neg), and PD-L2 was measured by qPCR (high vs low) in archival tumor specimens.

Results: As of Feb. 1, 2013, 171 patients were evaluable for safety. Administered doses include ≤1 (n=9), 3 (n=3), 10 (n=35), 15 (n=57) and 20 mg/kg (n=67). Patients in the dose-escalation cohorts did not experience dose limiting toxicities (DLTs). No maximum tolerated dose (MTD) was identified. Patients had received MPDL3280A for a median duration of 147 days (range 1-450). 41% of patients reported G3/4 AEs, regardless of attribution. No acute pneumonitis was observed. 122 patients enrolled prior to Jul. 1, 2012 were evaluable for efficacy. RECIST responses were observed in multiple tumor types including NSCLC (9/37), RCC (5/39), melanoma (9/35), CRC (1/4) and gastric cancer (1/1). An ORR of 21% (25/122) was observed in non-selected solid tumors with a duration of response range of 1+ to 253+ days. Other patients had delayed responses after apparent radiographic progression (not included in the ORR). The 24-week PFS was 42%. 94 patients had tumors evaluable for PD-L1 status, and 81 patients had tumors evaluable for PD-L2. Median PD-L2 expression was ≈2× higher in PD-L1-positive tumors versus PD-L1-negative tumors. The ORR was 39% (13/33) for patients with PD-L1-positive tumors versus 13% (8/61) for patients with PD-L1-negative tumors. Patients with PD-L2High tumors showed an ORR of 27% (11/41), versus 13% (5/40) for patients with PD-L2Low tumors.

MPDL3280A was well tolerated, with no pneumonitis-related deaths. Durable responses were observed in a variety of tumors. PD-L1 and PD-L2 tumor status appears to correlate with responses to MPDL3280A. This preliminary data provides additional support that PD-L1 as well as PD-L2 expression in tumor samples, including expression on tumor cells, tumor infiltrating immune cells (IC), and/or within the tumor microenvironment such as stromal cell and any combinations thereof, may predict responsiveness of a patient to cancer therapy which involves inhibition of the PD-L1/PD-1 pathway. The data further supports that PD-L1 and PD-L2 tumor status may determine likelihood that a patient will exhibit benefit from treatment with a PD-L1 axis binding antagonist such as an anti-PD-L1 antibody.

Example 8—Anti-PD-L1 Antibody Treatment Leads to Increased T-Cell Activation in PD-L1+ Patients Responding to Treatment The value of on-treatment tumor biopsy for assessing clinical benefit to patients responding to anti-PD-L1 antibody and the identification of pharmacodynamic (PD) biomarkers associated with treatment effectiveness was evaluated.

Figure 7:
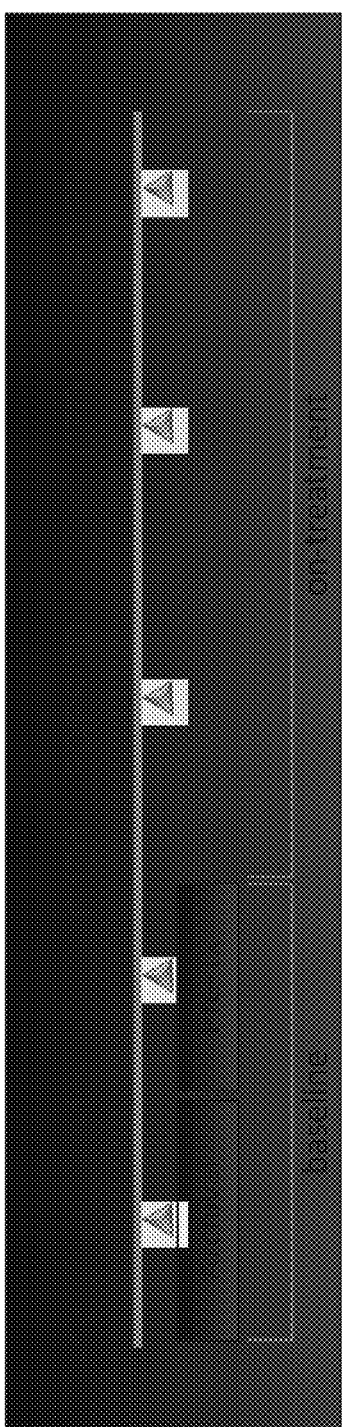
FIG. 7 shows a schematic of serial pre-/on-treatment tumor biopsies from patients treated with anti-PD-L1 antibody. Paired baseline (which includes either pre-treatment or archival tumor tissue) and on-treatment tumor biopsies from patients treated with anti-PD-L1 antibody (n=26) suffering from various indications including melanoma, renal cell carcinoma (RCC), non-small cell lung cancer (NSCLC), head and neck cancer (H&N), colorectal cancer (CRC), gastric, and breast cancer were evaluated.

As illustrated in FIG. 7, serial pre-/on-treatment tumor biopsies from patients treated with anti-PD-L1 antibody from the ongoing Phase I study were assessed. Paired baseline (which includes either pre-treatment or archival tumor tissue) and on-treatment tumor biopsies from patients treated with anti-PD-L1 antibody (n=26) suffering from various indications including melanoma, RCC, NSCLC, H&N, CRC, gastric, and breast cancer, were analyzed for CD8+ T cell infiltration using an anti-CD8 IHC reagent as well as pharmacodynamic biomarkers via gene expression analysis.

Figure 8:
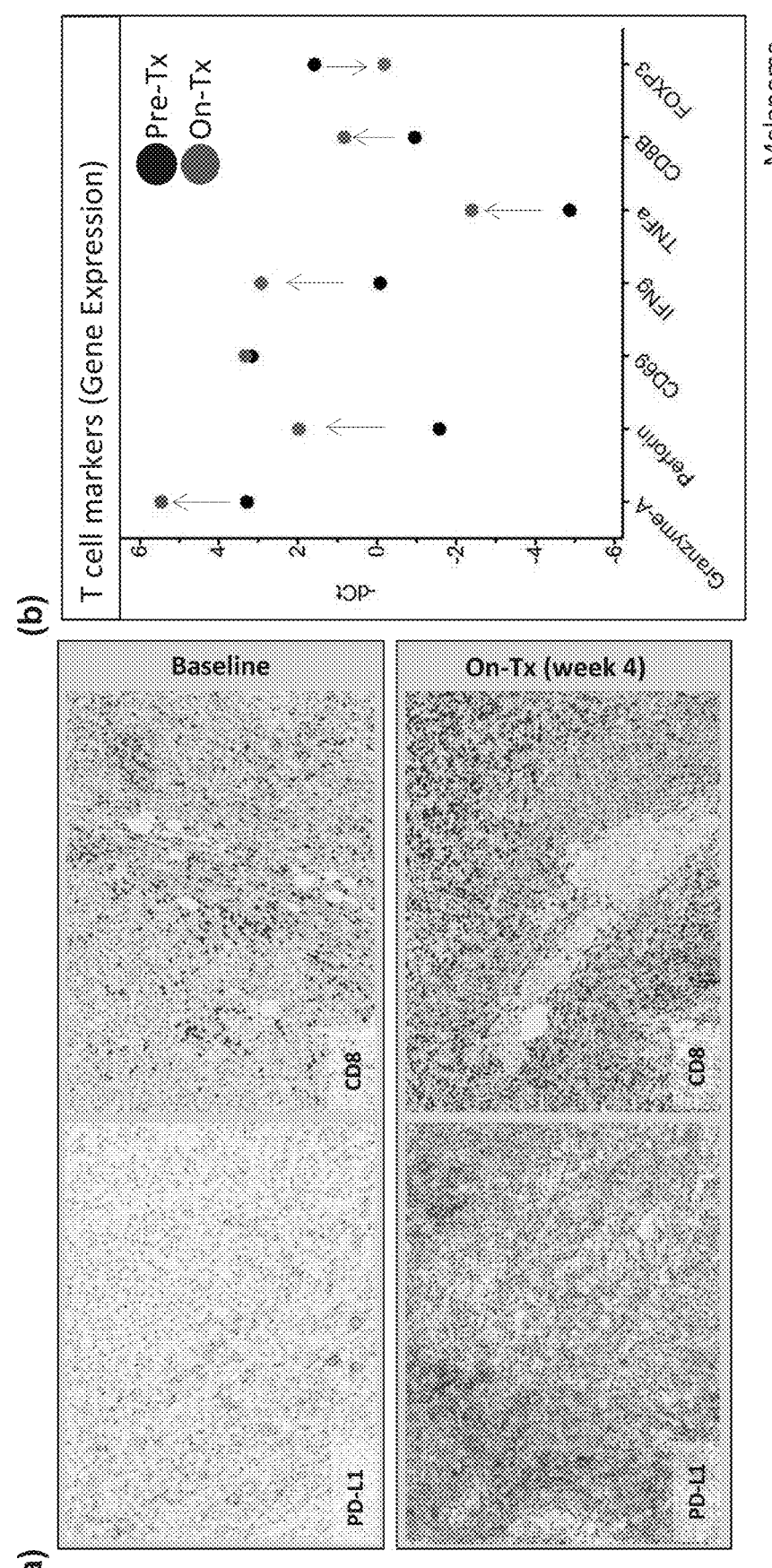
FIG. 8 shows (a) an increase in CD8+ T cell infiltration was associated with an increase in PD-L1 expression in tumor samples from patients responding to treatment with anti-PD-L1 antibody; and (b) an increase in T cell activation markers, including Granzyme A, Perforin, IFN-g, TNFa and CD8, following treatment with anti-PD-L1 antibody in patients responding to treatment with anti-PD-L1 antibody.

As illustrated in FIG. 8(a), an increase in CD8+ T cell infiltration was associated with an increase in PD-L1 expression in tumor samples from patients responding to treatment with anti-PD-L1 antibody. Under baseline conditions, T-cells and PD-L1+ tumor cells may co-localize and focal PD-L1 expression may represent an interface between cancer cells and immune cells (anti-tumor T-cell attack may be controlled by tumor or immune cell PD-L1 expression). At week 4 post Cycle 1 Day 1 (C1D1) treatment with anti-PD-L1 antibody, an increase in PD-L1 expression within the tumor sample was detected along with dense lymphocytic infiltration, in particular CD8+ T cell infiltration. This increase in CD8+ T cells may lead to T-cell mediated killing of tumor cells which in turn may lead to T-cell proliferation and activation. Such activated T-cells may release IFN-g and may also induce PD-L1 expression in neighboring tumor cells and/or immune cells.

As illustrated in FIG. 8(b), a number of T-cell activation markers were found to be increased in patients responding to anti-PD-L1 antibody treatment. The gene expression levels of T cell activation markers, including Granzyme A, Perforin, IFN-g, TNFa and CD8, were found to be increased following treatment with anti-PD-L1 antibody in patients responding to treatment with anti-PD-L1 antibody compared to baseline levels pre-treatment.

This data suggests that an increase in CD8+ T cell infiltration correlated with an increase in PDL-1 expression in tumor samples from patients responding to anti-PD-L1 antibody treatment. Furthermore, the expression of a number of T cell activation markers, including but not limited to, Granzyme A, Perforin, IFN-g, TNFa and CD8, were found to be increased in tumor samples from patients responding to anti-PD-L1 antibody treatment. These markers may be useful pharmacodynamic biomarkers to assess clinical benefit and efficacy of therapy that involves inhibition of the PD-L1/PD-1 pathway which includes using an anti-PD-L1 antibody.

Example 9—Adaptive Increase in PD-L1
Expression is Prominent in Patients Responding to
Treatment In addition to the increase in CD8+ T cell infiltration and expression of T cell activation markers in tumor samples from patients responding to anti-PD-L1 antibody treatment, an increase in tumor PD-L1 expression was also observed in patients responding to anti-PD-L1 antibody treatment.

As illustrated in FIG. 9, a summary of responses to anti-PD-L1 antibody in paired tumor biopsies is presented. In all instances (4/4 patients; 100%) where there was >30% reduction in the sum of the longest diameter of the target lesions (SLD) in patients responding to anti-PD-L1 antibody treatment, there was also an increase in the tumor PD-L1 expression as measured by PD-L1 IHC. Even with a 0-30% reduction in SLD in patients responding to anti-PD-L1 antibody treatment, 33% of the patients (2/6 patients) displayed an increase in the tumor PD-L1 expression following treatment.

In contrast, in patients that did not respond to anti-PD-L1 antibody treatment and that displayed a 0-20% increase in SLD, only 1/10 patients displayed an increase in tumor PD-L1 expression. Furthermore, for patients that displayed >20% increase in SLD, none (0/4 patients) displayed any measurable increase in tumor PD-L1 expression.

This preliminary data suggests that PD-L1 expression in tumors may increase in patients responding to treatment with anti-PD-L1 antibody and that such an increase may be an adaptive increase that may serve as pharmacodynamic biomarkers, an indicator of local tumor infiltrating leukocytes (TILs) attacking the tumor and also as a marker to assess clinical benefit and efficacy of therapy that involves inhibition of the PD-L1/PD-1 pathway which includes using an anti-PD-L1 antibody.

Example 10—Anti-PD-L1 Antibody Treatment
Leads to Increased Frequency of Activated T-Cells
in Blood The identification of pharmacodynamic (PD) biomarkers of anti-PD-L1 antibody treatment in the blood was also evaluated.

Flow Cytometry (FACS) Analysis:

Whole blood was collected in sodium heparin (NaHep) blood collection tubes. Blood was mixed by slowly inverting the collection tube. The cells were stained with the appropriate antibody combinations and incubated at room temperature for 30 minutes in the dark. After incubation, FACS-Lyse was added to all tubes. The tubes were vortexed and incubated at room temperature in the dark for 10 minutes. The cells were washed with PBS with 1% BSA. After washing, FACSPerm2 was added to all tubes and incubated at room temperature in the dark for 10 minutes. After incubation, the cells were washed with PBS with 1% BSA and incubated with antibody, if applicable. After the incubation, cells were washed with PBS with 1% BSA and resuspended in 1% Paraformaldehyde. The tubes were stored at 2-8° C. until they were acquired on the FACSCantoII flow cytometer.

Figure 10:
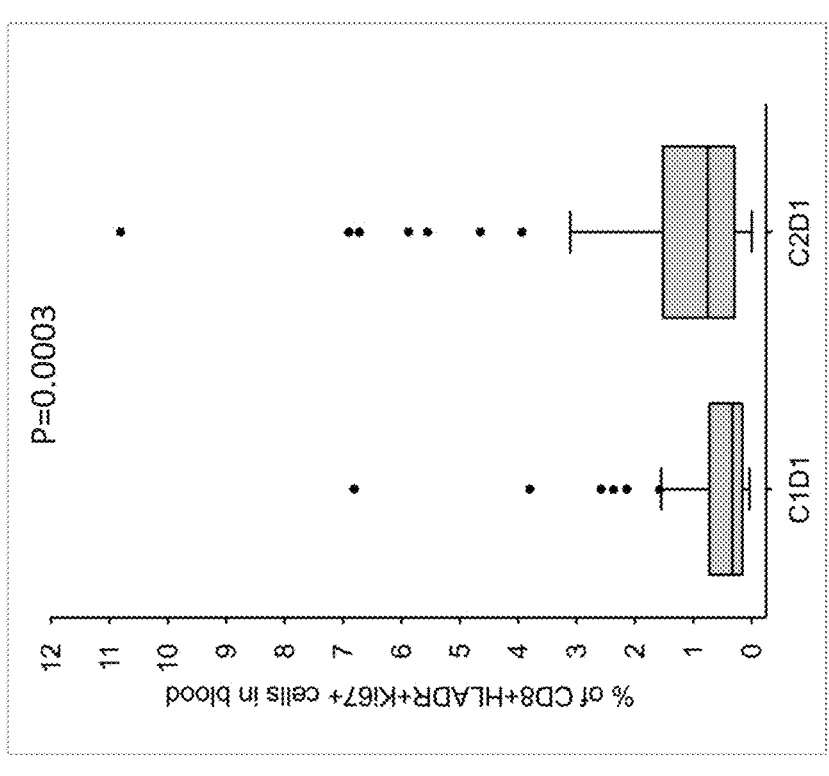
FIG. 10 shows (a) an increased frequency of proliferating T-cells in blood, identified as being CD8+/Ki67+ cells; and (b) an increased frequency of activated proliferating T-cells, identified as being CD8+/HLA-DR+/Ki67+ cells, in patients undergoing treatment with anti-PD-L1 antibody.

As illustrated in FIG. 10(*a*), proliferating T-cells in blood, identified as being CD8+/Ki67+, increase during the course of anti-PD-L1 antibody treatment with a ~2-fold increase at C2D1 (Cycle 2 Day 1) compared to C1D1 (Cycle 1 Day 1). Furthermore, as illustrated in FIG. 10(*b*), proliferating T-cells that are also activated in blood, identified as being CD8+/HLA-DR+/Ki67+, increase during the course of anti-PD-L1 treatment and are more frequent at C2D1 (~2-fold increase).

This preliminary data suggests that activated T-cell proliferation in blood may increase during the course of anti-PD-L1 antibody treatment and may serve as a pharmacodynamic biomarker of therapy that involves inhibition of the PD-L1/PD-1 pathway which includes using an anti-PD-L1 antibody.

Example 11—a Decrease in IL-6 Expression in
Plasma May be Associated with Patients
Responding to Treatment The identification of pharmacodynamic (PD) biomarkers of anti-PD-L1 antibody treatment in the plasma was also evaluated.

Plasma Analysis

Blood was collected into Sodium Heparin collection tubes. Tube was mixed thoroughly by slowly inverting the collection tube. Subsequently, collection tubes were centrifuged in a refrigerated centrifuge at a minimum of 1500-2000×g for 15 minutes. Plasma was transferred to polypropylene cryovials and kept frozen until analysis. Plasma was analyzed for IL-6 and other cytokines using modified ELISA according to manufacturer recommendations.

Figure 11:
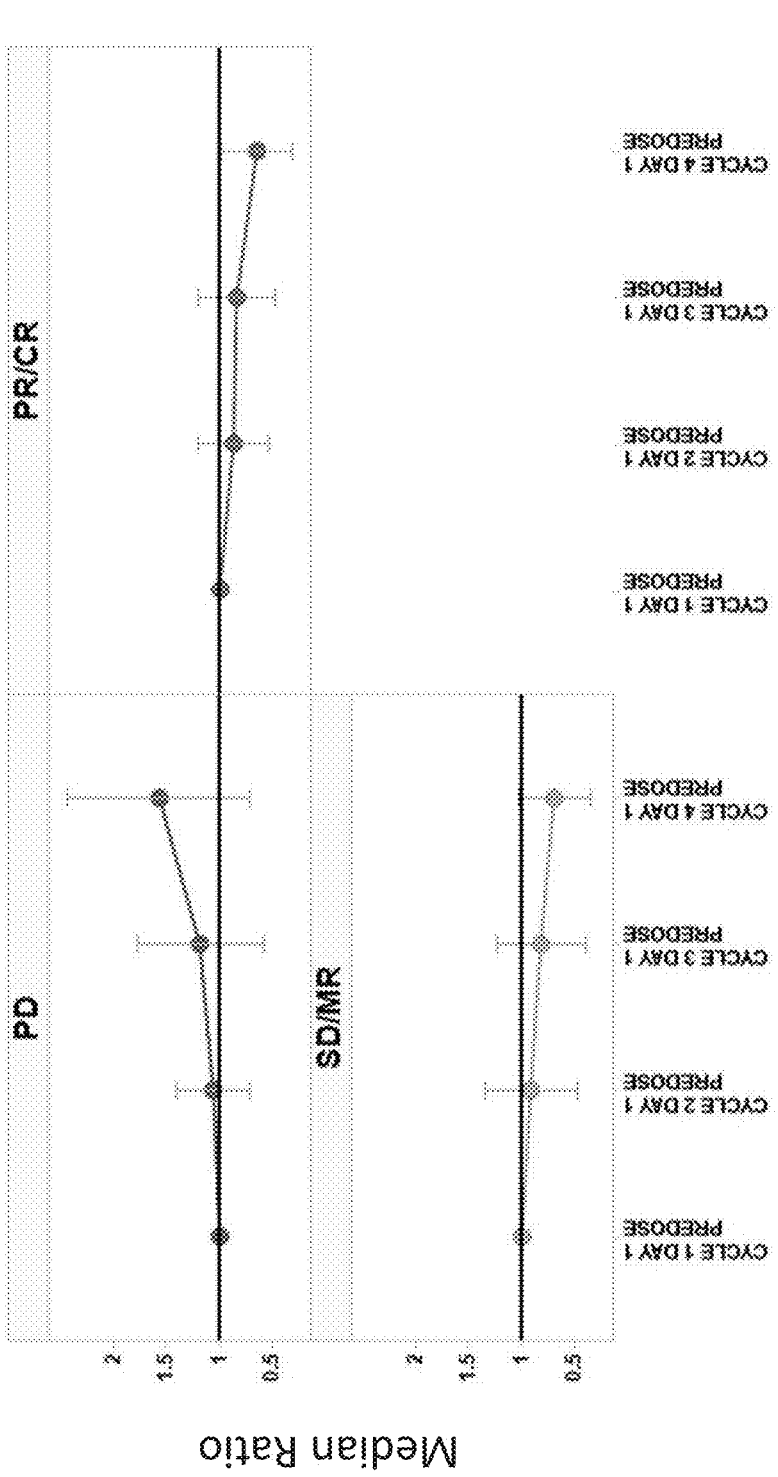
FIG. 11 shows that a decrease in IL-6 levels in the plasma was associated with patients responding to the anti-PD-L1 antibody treatment and that an increase in IL-6 levels in the plasma was associated with patients progressing upon the anti-PD-L1 antibody treatment.

As illustrated in FIG. 11, a decrease in IL-6 levels in the plasma was associated with patients responding to the anti-PD-L1 antibody treatment. Specifically, patients that exhibited beneficial PR/CR responses (partial response/complete response) over the course of treatment also exhibited a measurable decrease in the IL-6 levels.

In contrast, patients that did not benefit from treatment with anti-PD-L1 antibody was associated with an increase in IL-6 levels in the plasma over the course of treatment. As illustrated in FIG. 11, patients that exhibited PD responses (progressive disease) over the course of treatment exhibited a measurable increase in the IL-6 levels.

This preliminary data suggests that IL-6 levels in plasma may serve as a pharmacodynamic biomarker to assess clinical benefit and efficacy of therapy that involves inhibition of the PD-L1/PD-1 pathway which includes using an anti-PD-L1 antibody.

Example 12—Tumor Immune Gene Expression in
Samples from Individuals Treated with Anti-PD-L1
Antibody Shows Correlation with Response to
Treatment To further evaluate additional immune gene signatures and a patients' responsiveness to treatment with protocol, gene expression analysis was performed as previously described in Example 6 using Fluidigm gene expression analysis.

Figure 12:
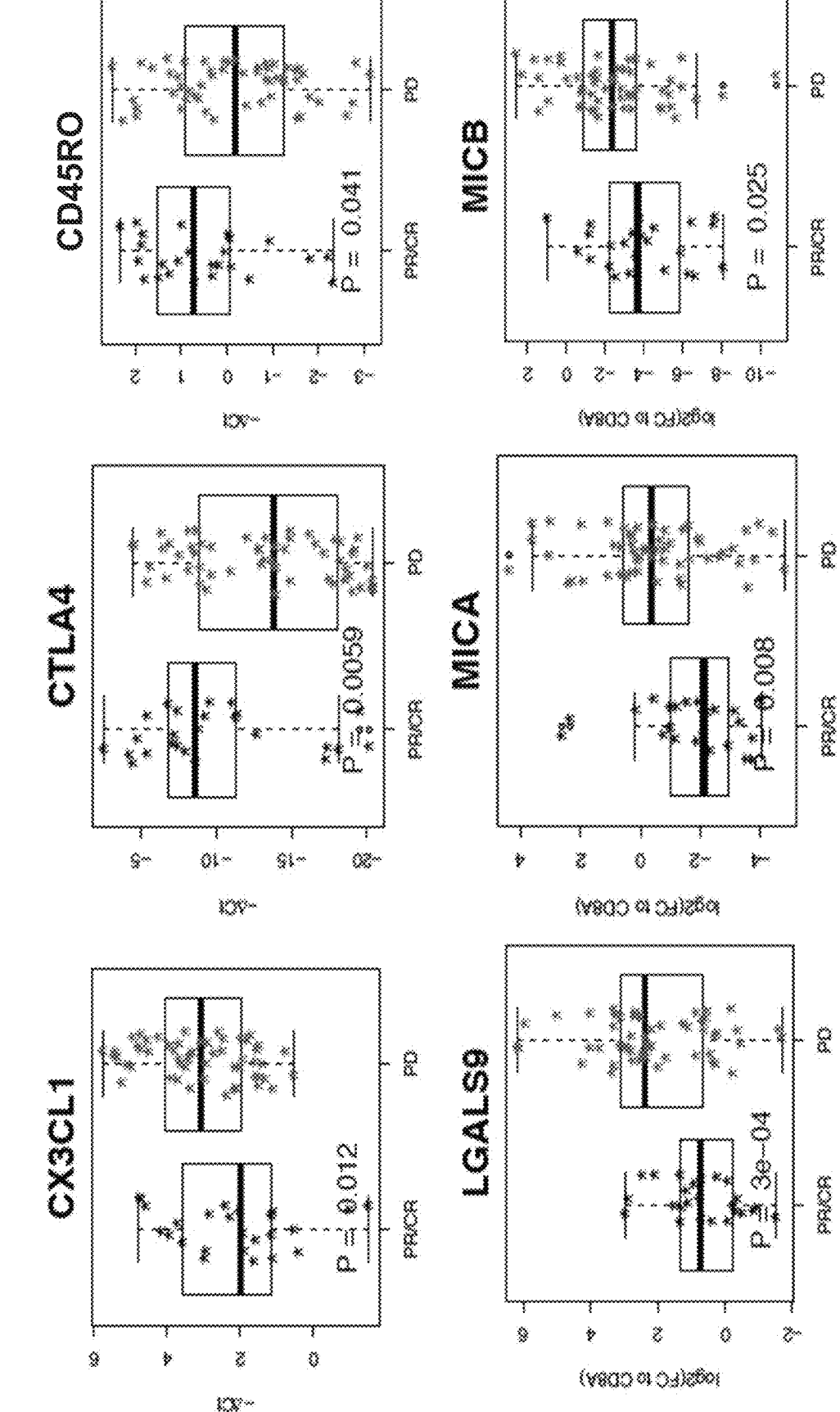
FIG. 12 shows the correlation of various immune gene expressions in tumor samples with either PD or PR/CR response to anti-PD-L1 treatment in cancer patients. PD=progressive disease; PR=partial response; CR=complete response.

As illustrated in FIG. 12, a correlation exists between a number of additional immune related genes and the response of patients to treatment with anti-PD-L1 antibody. Specifically, the gene expression levels of CTLA4 and CD45RO were observed to be higher in patients that either displayed partial response (PR) or complete response (CR) following treatment with anti-PD-L1 antibody, as compared to patients with progressive disease (PD). FIG. 12 also illustrates that the gene expression levels of CX3CL1 (a chemokine), LGLS9 (Galectin-9), MIC-A and MIC-B were observed to be lower in patients responding to treatment with anti-PD-L1 antibody (PR/CR), as compared to patients with PD. HK. This data represents pooled gene expression levels from samples collected from patients suffering from the following cancer indications: melanoma, RCC, NSCLC, CRC, gastric cancer, bladder cancer, ovarian cancer, breast cancer, head & neck cancer, pancreatic cancer, sarcoma, esophageal cancer, SCLC, multiple myeloma, NHL, and endometrial cancer.

Interestingly, certain immune related genes display different correlation patterns with the patients' response to treatment with anti-PD-L1 antibody depending on the disease indication. As illustrated in FIG. 13, the gene expression level of IDO1 (Indoleamine-pyrrole 2,3-dioxygenase) was higher in melanoma patients that either displayed partial response (PR) or complete response (CR) following treatment with anti-PD-L1 antibody, as compared to patients with progressive disease (PD). However, in NSCLC patients, the gene expression level of IDO1 was lower in patients that either displayed PR or CR following treatment with anti-PD-L1 antibody, as compared to patients with PD. Thus, it is possible that these biomarkers may show differing correlation profiles depending on the disease indication.

These results suggest that additional predictive biomarkers have been identified which may help to identify patients who are more likely to respond to cancer therapy which involves inhibition of the PD-L1/PD-1 pathway, such as using an anti-PD-L1 antibody.

Example 13—PD-L1 Expression on Circulating T Cells in Blood Correlates with Response to Treatment with Anti-PD-L1 Antibody To evaluate whether PD-L1 expression on circulating T cells correlated with patient response to treatment with anti-PD-L1 antibody, blood samples were collected within 60 days prior to treatment and FACs analysis was performed to determine the level of PD-L1 expression on T cells in the sample.

Briefly, blood samples from pre-treatment patients were collected in tubes containing anti-coagulant (e.g. sodium heparin, EDTA, or citrate). The collected blood was mixed in the collection tubes thoroughly by slowly inverting the collection tube at least 3 times. Approximately 100 µL of an anticoagulated whole blood was pipetted into appropriately labeled test tubes. The blood was stained with the following primary antibodies and incubated at room temperature for 30 minutes in the dark: anti-CD3 antibody, anti-CD8 antibody and anti-PD-L1 antibody. Following primary antibody staining, the red blood cells were then lysed using for example ammonium chloride lysing solution, and then cells were washed with 2 mL PBS with 1% BSA. The blood cells were then stained with secondary antibody or an appropriate amount of streptavidin-(dye) (if biotinylated primary antibody were used) for 20 minutes in the dark at room temperature. Cells were then washed again with PBS containing 1% BSA, resuspended in 1% paraformaldehyde and stored at 2-8° C. until they were acquired on the flow cytometer.

As shown in FIG. 14, there is a correlation between elevated PD-L1 expression on circulating T cells (CD3+/CD8+) and the patients' clinical response to anti-PD-L1 treatment. Patients that displayed wither a partial response (PR) or complete response (CR) following anti-PD-L1 treatment correlated with elevated levels of PD-L1 expression on their circulating T cells. In contrast, patients that displayed no clinical response to anti-PD-L1 treatment (e.g., having progressive disease (PD)) exhibited lower PD-L1 expression on their circulating T cells.

These results suggest that PD-L1 expression on circulating T cells may be a valuable and useful biomarker for predicting responsiveness of a patient to cancer therapy which involves inhibition of the PD-L1/PD-1 pathway using, for example, an anti-PD-L1 antibody.

Example 14—a Phase Ia Study of Individuals Treated with Anti-PD-L1 Antibody and the Correlation with Response to Treatment in Diagnostic Selected Individuals Study PCD4989g is an ongoing Phase Ia trial in patients with advanced solid tumors and hematologic malignancies to evaluate the safety and tolerability of an anti-PD-L1 antibody (MPDL3280A) administered by intravenous infusion every 3 weeks. The study contains a large cohort of NSCLC patients (n=79, including 53 with a minimum of 6 months of follow-up).

These preliminary results from Study PCD4989g suggest that PD-L1 expression in tumor-infiltrating immune cells is associated with response to MPDL3280A. PD-L1 positivity in NSCLC is defined as discernible PD-L1 staining of any intensity in tumor-infiltrating immune cells covering ≥5% of tumor area occupied by tumor cells, associated intratumoral, and contiguous peri-tumoral desmoplastic stroma. The proposed criteria for PD-L1 diagnostic assessment in NSCLC is provided below:

| PD-L1 Diagnostic Assessment | IHC Scores |
| --- | --- |
| Absence of any discernible PD-L1 staining OR Presence of discernible PD-L1 staining of any intensity in tumor-infiltrating immune cells covering <1% of tumor area occupied by tumor cells, associated intratumoral, and contiguous peri-tumoral desmoplastic stroma | IHC 0 |
| Presence of discernible PD-L1 staining of any intensity in tumor-infiltrating immune cells covering ≥1% to <5% of tumor area occupied by tumor cells, associated intratumoral, and contiguous peri-tumoral desmoplastic stroma | IHC 1 |
| Presence of discernible PD-L1 staining of any intensity in tumor infiltrating immune cells covering ≥5% to <10% of tumor area occupied by tumor cells, associated intratumoral, and contiguous peri-tumoral desmoplastic stroma | IHC 2 |
| Presence of discernible PD-L1 staining of any intensity in tumor infiltrating immune cells covering ≥10% of tumor area occupied by tumor cells, associated intratumoral, and contiguous peri-tumoral desmoplastic stroma | IHC 3 |

As of the data cutoff of 30 Apr. 2013, there were 53 patients with locally advanced or metastatic NSCLC dosed prior to 1 Oct. 2012 with a minimum of 6 months of follow-up. The median age of this group was 62 years (range, 24-84 years), and the group represented a heavily pre-treated patient population: 84.9% had ≥2 prior systemic therapies and 52.8% had ≥4 prior systemic therapies. Dramatic responses have been observed in NSCLC, including in patients who failed multiple systemic therapies and/or who had been symptomatic prior to starting treatment. The median time to response is 11.7 weeks, with approximately 90% of responses observed by 24 weeks (6 months). The objective response rate (ORR) in all NSCLC patients with a minimum of 6 months of follow-up is 22.6% (95% CI: 12.3%-35.1%).

PD-L1 positivity of tumor-infiltrating immune cells appeared to predict a higher response in NSCLC patients treated with MPDL3280A. NSCLC patients with 5% PD-L1-positive tumor-infiltrating immune cells (IHC 2/3) had an ORR of 46.2% (95% CI: 22.4%-74.0%) compared with the 18.2% (95% CI: 8.2%-33.8%) in patients with diagnostic profiles of IHC 0/1. When a higher diagnostic threshold of 10% PD-L1-positive tumor-infiltrating immune cells (IHC 3) was used, PD-L1-positive patients had an ORR of 83.3% (95% CI: 40.2%-99.1%) compared with the 17.5% (95% CI: 7.8%-31.5%) in patients with diagnostic profiles of IHC 0/1. Preliminary experience shows that the diagnostic cutoff of IHC 2/3 is associated with significant clinical benefit for NSCLC patients treated with MPDL3280A. Patients who responded appeared to have developed durable anti-tumor immunity, with all NSCLC responses continuing with 170 to 534 days on study at the time of data cutoff.

Example 15—Tumor Immune Gene Signature of Samples from Individuals Treated with Anti-PD-L1 Antibody Shows Correlation with Response to Treatment Immunologic pharmacodynamics effects were evaluated in tumors and bloods from patients treated with MPDL3280A. On treatment, responding tumors showed increase in expression of tumor cell and tumor infiltrating immune cell PD-L1 expression, infiltration of CD8+ T-cells and a Th1-dominant immune infiltrate, providing evidence for adaptive PD-L1 up-regulation. Non-responders showed minimal tumor CD8+ T-cell infiltration and an absence of T-cell activation (measured by Granzymes, Perforin and EOMES expression).

Figure 15:
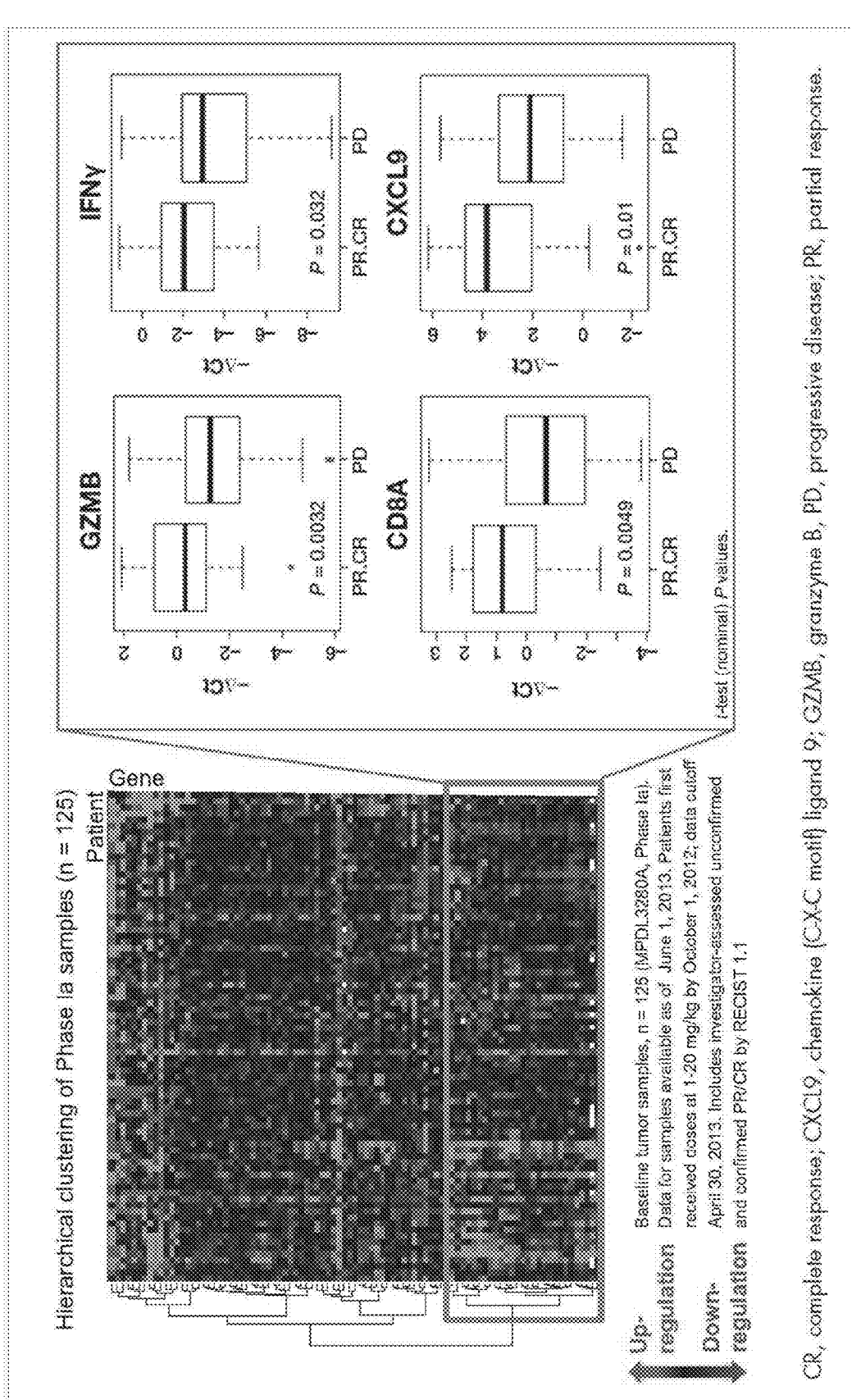
FIG. 15 shows correlation of gene expression of cytotoxic Th1 cells, IFN-g and T-cell trafficking markers in tumor samples with either PD or PR/CR response to anti-PD-L1 treatment in cancer patients. PD=progressive disease; PR=partial response; CR=complete response.

As illustrated in FIG. 15, anti-tumor response to MPDL3280A was associated with markers related to T-cell biology. Specifically, higher gene expression of cytotoxic T h1 cells, IFN-g and T-cell trafficking markers were detected in tumor tissue at baseline and this was associated with MPDL3280A activity. For example, the T cell activation immune genes, including IFN-g, CD8A, Granzyme B and CXCL9, were found to correlate with patient partial response/complete response to treatment with MPDL3280A. The data set includes patients with samples available as of Jun. 1, 2013.

Figure 16:
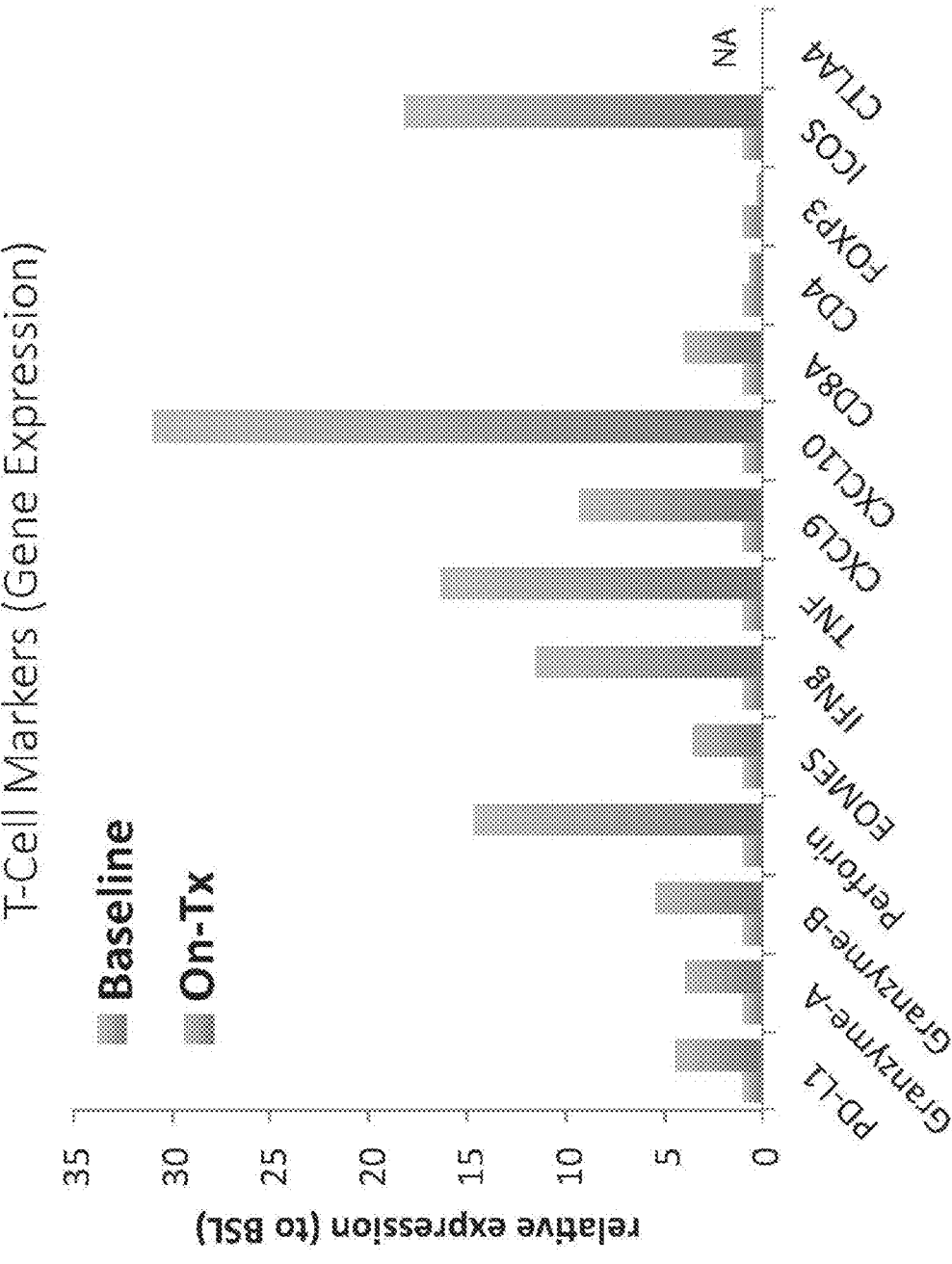
FIG. 16 shows an increase in T cell activation markers in a melanoma patient responding to treatment with anti-PD-L1 antibody.

As illustrated in FIG. 16, MPDL3280A leads to increased T cell activation in a patient with melanoma responding to treatment. Specifically, a number of T-cell activation markers were found to be increased in patients responding MPDL3280A including Granzyme A, Granzyme B, Perforin, EOMES, IFN-g, TNF, CXCL9, CXCL10, CD8A and ICOS.

Figure 17:
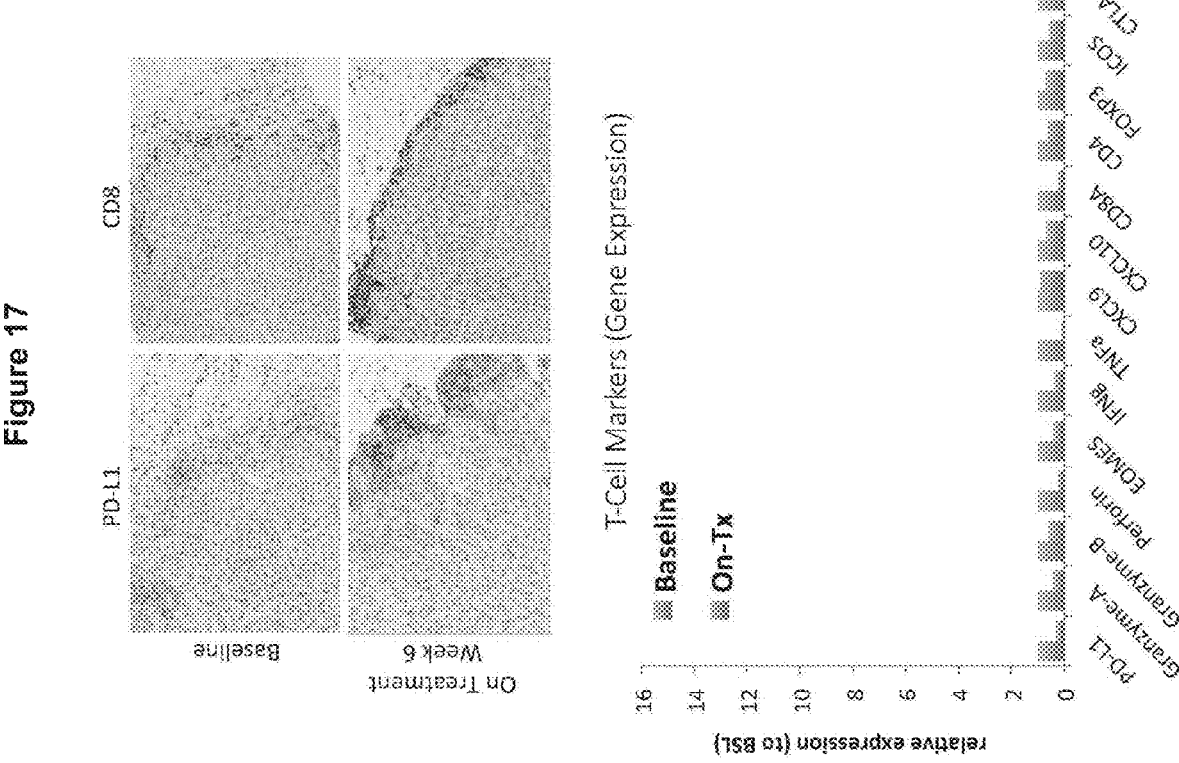
FIG. 17 shows a low frequency of intratumoral T cells and lack of T cell activation in T cell activation markers in a melanoma patient not responding to treatment with anti-PD-L1 antibody.

In contrast, in a patient with melanoma not responding to MPDL3280A exhibited low frequency of intratumoral T cells and lacks T cell activation, as illustrated in FIG. 17.

Figure 18:
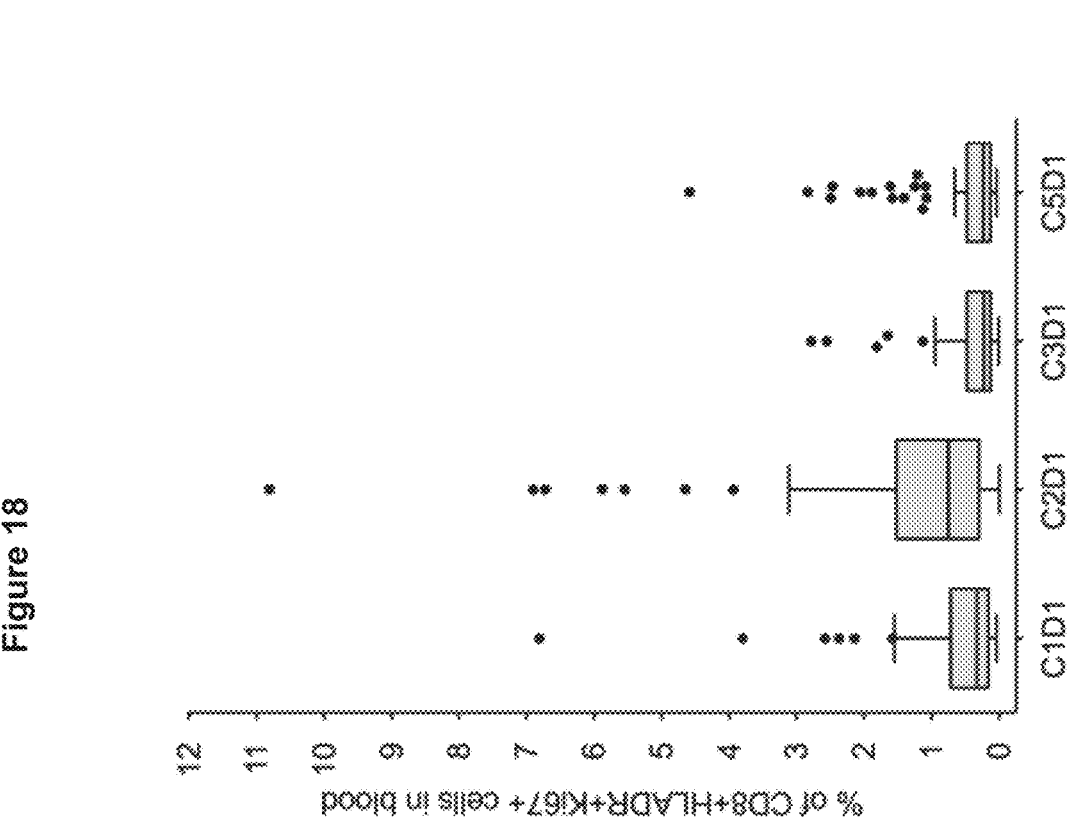
FIG. 18 shows a transient increase in the frequency of CD8+/HLA-DR+/Ki-67+ activated T cells in the blood of patients responding to treatment with anti-PD-L1 antibody.

Circulating biomarkers for their association with clinical outcomes was also evaluated. The frequency of CD8+ HLA-DR+Ki67+ T-cells in the blood increased shortly following the first dose of MPDL3280A and returned to baseline levels by the end of cycle 2 when assessed in all patients, representing a transient pharmacodynamic measurement of PD-L1 inhibition. As illustrated in FIG. 18, MPDL3280A leads to transient increase in the frequency of activated T cells in blood and suggests that CD8+ HLA-DR+Ki67+ T-cells may be a potential pharmacodynamics biomarker of MPDL3280A treatment.

Figure 19:
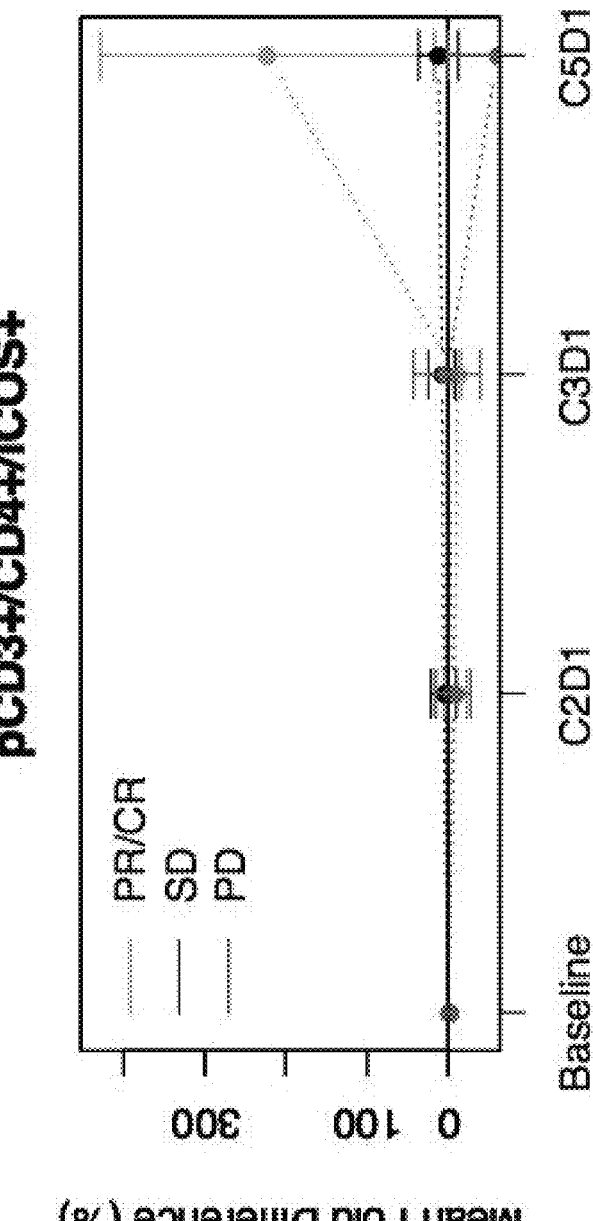
FIG. 19 shows fluctuations in CD4+/ICOS+ T cells, with delayed increases in this T cell population correlating with response and decreases with disease progression (occurring after cycle 3).

Significant fluctuations in CD4+/ICOS+ T cells were observed, with delayed increases in this T cell population correlating with response and decreases with disease progression (occurring after cycle 3), as illustrated in FIG. 19. The increase in CD4+/ICOS+ T cells might reflect the ancillary activation of T helper cell responses in patients who mount strong CD8+ anti-tumor T cell responses following treatment with to MPDL3280A.

Furthermore, an adaptive increase in PD-L1 expression was prominent in patients responding to MPDL3280A. As illustrated in FIG. 20, a summary of responses to MPDL3280A in paired tumor biopsies is presented. In patients responding to MPDL3280A, there was an increase in both the tumor cell PD-L1 expression as well as an increase in the tumor infiltrating immune cell PDL-1 expression, as measured by a PD-L1 IHC assay.

Figure 21:
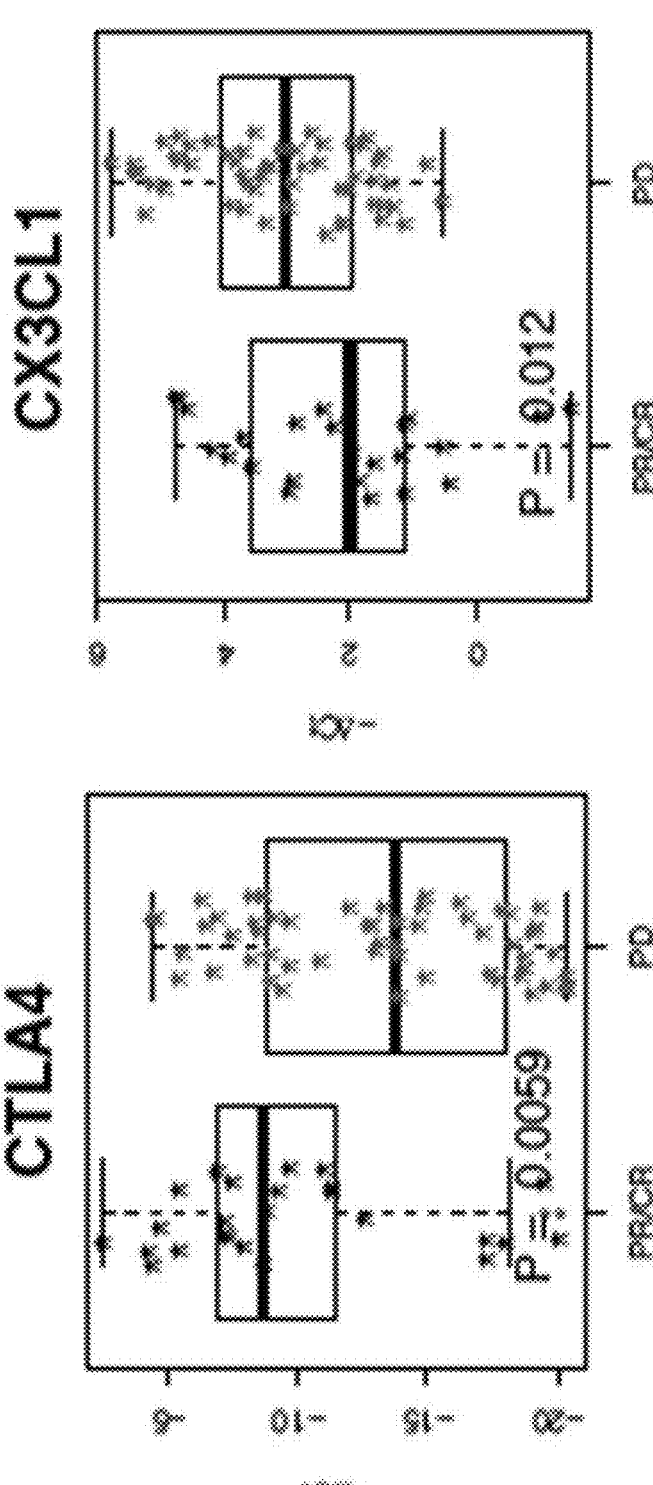
FIG. 21 shows the correlation of CTLA4 expression with response to treatment with anti-PD-L1 antibody while the expression of fractalkine/CX3CL1 correlated with progression.

Example 16—CTLA4 and Fractalkine Expression Correlation with Response or Progression Following Anti-PD-L1 Antibody Treatment Across multiple cancer types, pre-treatment tumors exhibiting the presence of Th1-related gene expression, CTLA4, and the absence of fractalkine/CX3CL1, were associated with activity. Specifically, the expression of CTLA4 strongly correlated with response to MPDL3280A. while the expression of fractalkine/CX3CL1 in pre-treatment tumors strongly correlated with progression to MPDL3280A, as illustrated in FIG. 21.

The role of CTLA4 is well established as a factor expressed by T cells that can lead to inhibiting further T cell activation. The correlation of higher pre-treatment CTLA4 expression in patients that responded to MPDL3280A across the different tumor types suggests that CTLA4 serves as an important feedback mechanism in the anti-cancer immune response, and represents a marker of active T cell immunity and inflammation. In the periphery, however, the functional role of CTLA4 as a negative regulator appears less important than that of PD-L1.

The correlation of higher pre-treatment fractalkine (CX3CL1) expression in patients that experienced progression of disease to MPDL3280A was also unexpected, since this chemokine is generally associated with driving T cell infiltration. However, in its uncleaved form, fractalkine induces lymphocyte adhesion to endothelial cells and therefore may actually restrict T cell entry into the tumor bed. The association of fractalkine expression in tumors and progressive disease for patients treated with MPDL3280A suggests that fractalkine expression could also represent a feedback mechanism for tumors lacking an active immune response or represent an active tumor immune response suppressive factor.

These results suggest that CTLA4 and fractalkine may be valuable predictive biomarkers to help to identify patients who are more likely to respond to cancer therapy which involves inhibition of the PD-L1/PD-1 pathway, such as using an anti-PD-L1 antibody.

Example 17—Tumor Infiltrating Lymphocyte Signatures Across Six Cancer Types and their Association with Disease Prognostic Factors To further evaluate and understand the complexity of factors that may modulate or inhibit anti-tumor immunity and thus contribute to response or resistance to immune modulatory therapy, a number of highly sensitive immune gene expression assays (iCHIP) using the Fluidigm Biomark platform were used to interrogate the quality of the immune response across six cancer indications including CRC (n=48), BC (n=126), NSCLC (n=51), Melanoma (n=35), RCC (n=48), and bladder cancer (n=42). The iCHIP platform consists of 96 genes that represent signatures associated with IFNg pathway, cytotoxic T-cells, Th2 cells, T-effector cells, T-effector cells, T-regulatory cells, Th17 cells, myeloid cells, dendritic cells, NK cells, B-cells and immune checkpoint markers.

RNA was extracted from formalin-fixed paraffin embedded archival tissues that were derived from clinical collections or collected in the ongoing Phase I study of MPDL3280A (anti-PD-L1 antibody). Appropriate patient informed consents were obtained from the institutional review boards for the exploratory evaluation of biomarkers.

As shown in FIG. 22, the gene signatures associated with Teff (T-effector cells), Treg (T-regulatory cells), and Th17 is shown. Teff cells are defined by the gene cluster: CD8A, GZMB, IFNg, EOMES, GZMA, Perforin; Treg cells are defined by the gene cluster: FOXP3; and Th17 cells are defined by the gene cluster: RORC, IL17F, IL17A.

Immune gene expression analysis showed a unique pattern of immunosuppressive and immunoresponsive factors and cell types across indications. While indications, including triple-negative breast cancer (TNBC), NSCLC and bladder cancer represent the highest prevalence of IFN-g signatures, CRC and hormone receptor-positive breast cancer constitute diseases with the lowest expression. In addition to a high IFN-g signature in TNBC, this subtype of breast cancer also consists of a high Treg signature when compared to melanoma, which represents the highest ratio of IFN-g: Treg gene expression. Th17 gene signatures are most prevalent in CRC compared to all other indications. Association of these gene signatures with disease stage, outcomes (where available) and other disease specific known prognostic factors including molecular subtypes and mutations in KRAS, BRAF, PIK3CA and EGFR is currently ongoing.

In particular, in a cohort of RCC patients, a trend toward higher tumor gene expression of IL17F in patients who do not respond to anti-PD-L1 treatment was observed as illustrated in FIG. 23, despite the tumor gene expression of PD-L1 (CD274) being higher in responders to anti-PD-L1 treatment.

Figure 24:
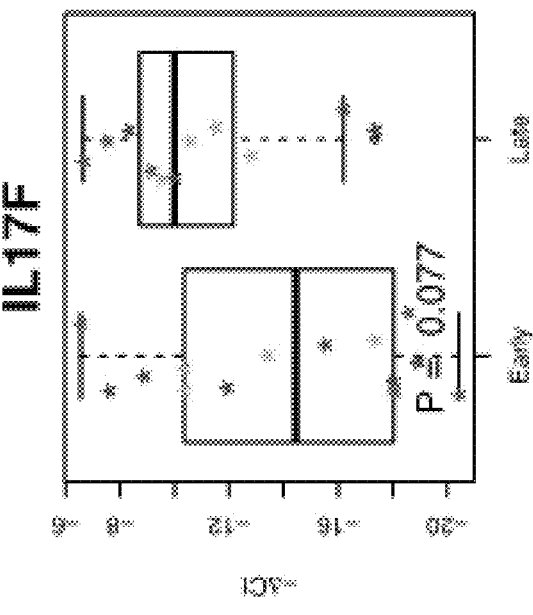
FIG. 24 shows tumor gene expression of IL-17F is higher in patients with a late response to anti-PD-L1 treatment.

Furthermore, tumor gene expression of IL-17F is higher in patients with a late response to anti-PD-L1 (respond after 6 months of therapy) across indications (melanoma, lung cancer, RCC), as illustrated in FIG. 24.

Thus, it is possible that certain biomarkers may show differing correlation profiles depending on the disease stage and timing of therapy involving inhibition of the PD-L1/PD-1 pathway.

Example 18—Inhibition of PD-L1 by MPDL3280A Leads to Clinical Activity in Patient with Metastatic Urothelial Bladder Cancer (UBC)

Metastatic UBC is associated with a poor prognosis and limited treatment options. PD-L1 expression is prevalent in this disease and may protect cancer cells from immune-mediated destruction by binding to its receptors PD-1 and B7.1.

In a Phase I study, UBC patients received MPDL3280A 15 mg/kg IV q3w for up to 1 year. Objective response rate (ORR; including unconfirmed responses) was assessed by RECIST v1.1. In parallel, tumor and circulating biomarkers were evaluated to study MPDL3280A immune correlates.

As of Sep. 19, 2013, 31 PD-L1+ UBC patients were treated with MPDL3280A. Patients were 84% male, had a median age of 66 y (42-86), 57% were ECOG PS 1 and 68% had visceral metastases. 71% received ≥2 prior therapies; 97% received prior platinum-based chemotherapy. Patients had received MPDL3280A for a median duration of 43 d (1-153) as of the data cutoff. The G1-4 treatment-related AEs occurring in ≥2 patients were pyrexia, anemia, decreased appetite, fatigue and nausea. Related G3-4 AEs occurred in 3.2% of patients. There were no immune-related AEs. 20 patients were evaluable for efficacy at time of analysis with a median follow up of 2.8 m (1.4-5). The ORR was 50% (1 CR and 9 PRs) with a median time to response of 43 d (39-82), corresponding to the first radiographic assessment and including patients with CNS, lung and bone metastases at baseline. All responders were still responding at the time of clinical cutoff.

Associations have been observed between PD-L1 status on tumor infiltrating immune cells and response to anti-PD-L1 treatment and further evaluations are ongoing to determine the association of PD-L1 status on tumor cells and response to anti-PD-L1 treatment.

Treatment resulted in transient increases in circulating Ki-67+CD8+ T cells, representing a potential pharmacodynamic (PD) biomarker of activity to therapy in patients with UBC with an inhibitor of the PD-1/PD-L1 pathway. As illustrated in FIG. 25, circulating Ki-67+CD8+ T cells demonstrated a transient rise during treatment with MPDL3280A.

Figure 26:
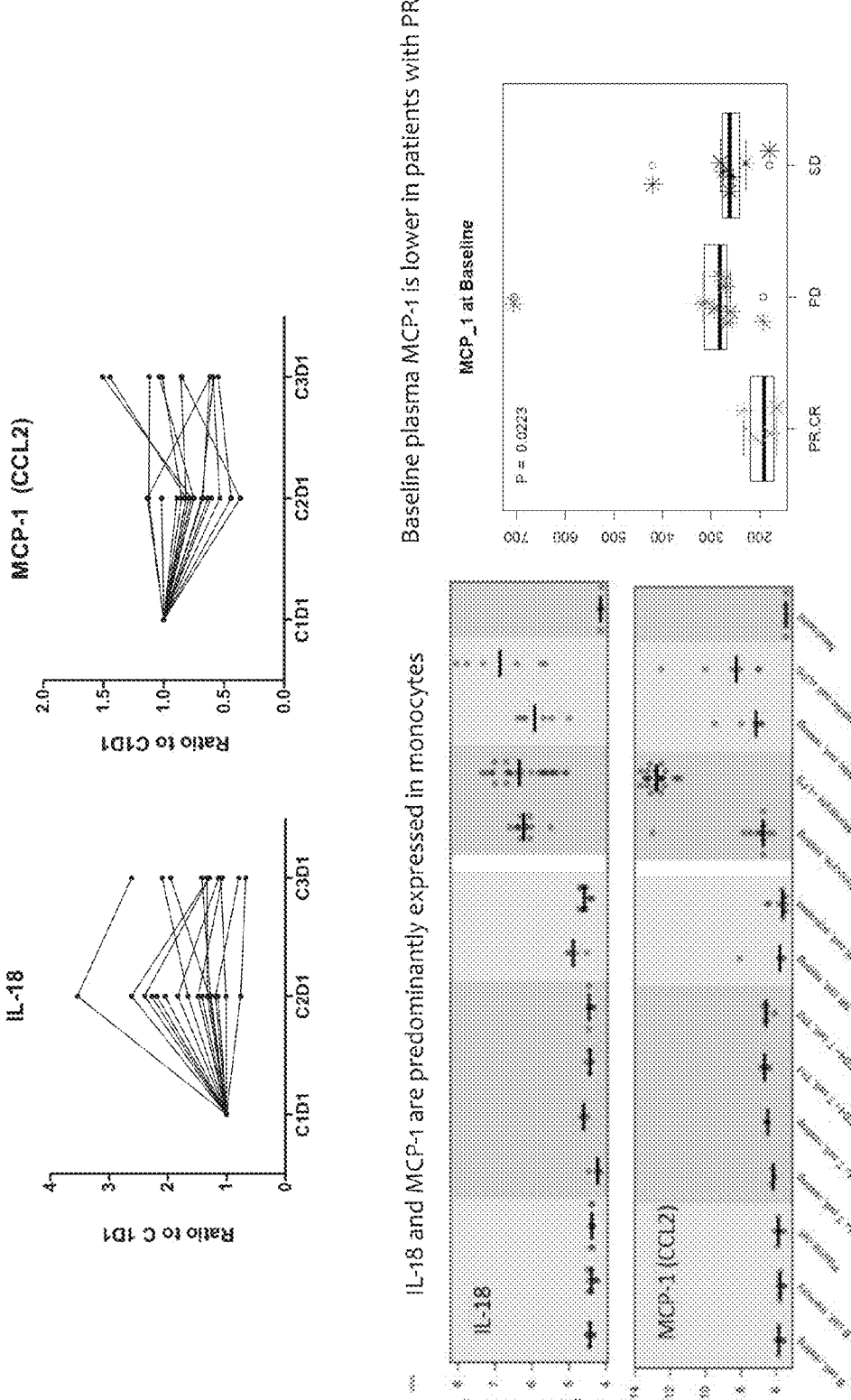
FIG. 26 shows transient increase in plasma IL-18 in patients undergoing treatment with anti-PD-L1 antibody. Furthermore, baseline plasma MCP-1 was lower in patients with partial response/complete response (PR/CR) to anti-PD-L1 treatment. Both IL-18 and MCP-1 were also predominantly expressed in monocytes.

Treatment also resulted in transient increase in plasma proteins, such as IL-18, which is upstream of IFN-g signaling, representing another PD biomarkers of activity, as illustrated in FIG. 26. Furthermore, baseline plasma MCP-1 was lower in patients with partial response/complete response (PR/CR). Both IL-18 and MCP-1 were predominantly expressed in monocytes, a component of the myeloid cells (see FIG. 26).

Figure 27:
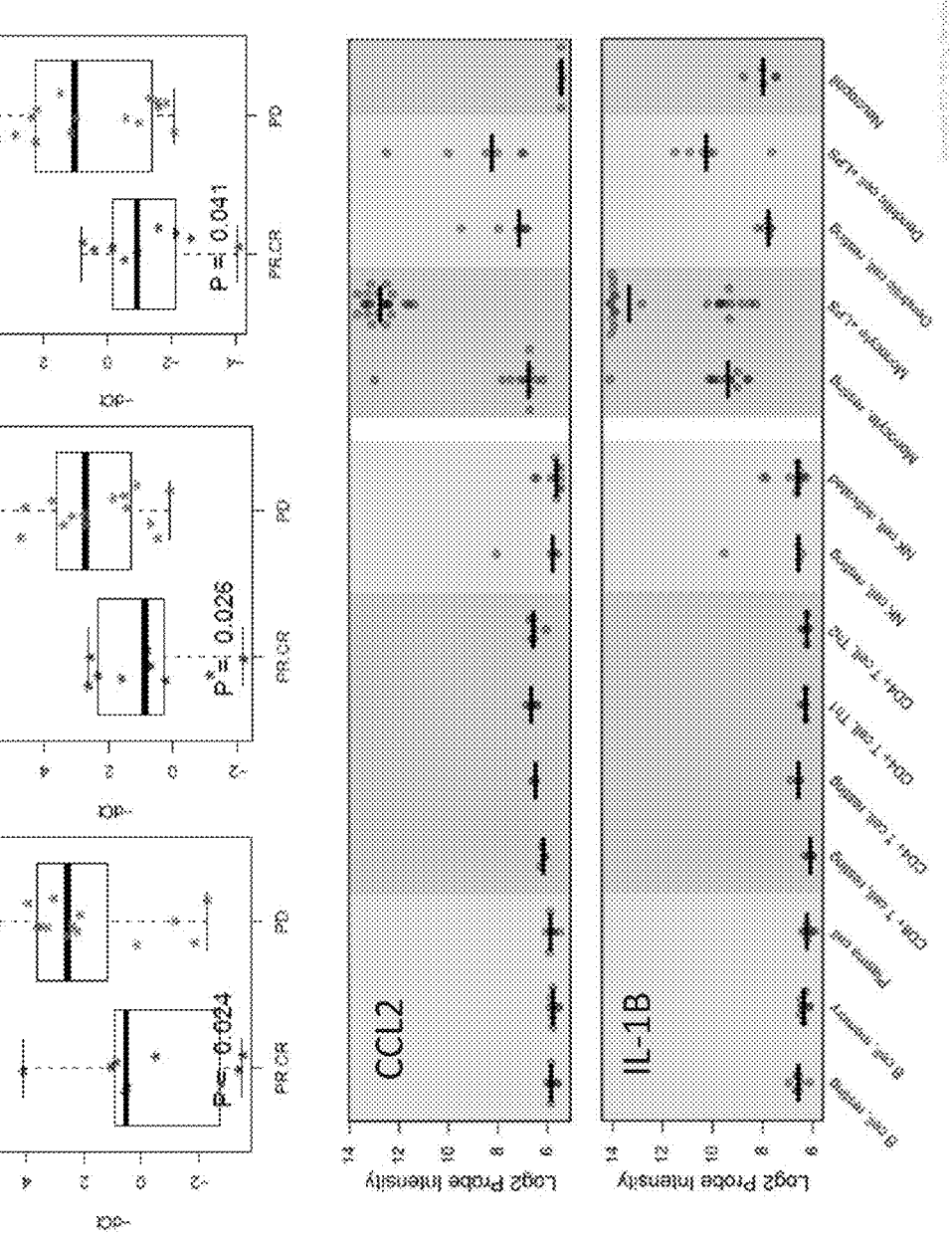
FIG. 27 shows that pretreatment tumors from patients that progressed following treatment with anti-PD-L1 antibody displayed a proportionally higher myeloid gene signature (IL-8, CCL2, and IL1B) that were predominantly expressed in myeloid cells (e.g., monocytes, dendritic cells)

Gene expression data from pretreatment tumors showed that patients who progressed had a proportionally higher myeloid gene signature. As illustrated in FIG. 27, patients that had progressive disease (PD) displayed elevated levels of IL-8, CCL2, and IL1B and these were associated with being present predominantly in myeloid type cells (e.g., monocytes, dendritic cells).

MPDL3280A was well tolerated in this pretreated PD-L1+ UBC population. 50% of patients treated responded to treatment. Responses were rapid and on-going. Biomarker analysis revealed PD markers, as well as markers of potential mechanisms of resistance to therapy.

Example 19—Elevated Levels of Soluble PD-L1 is Prominent in Patients Responding to Treatment Elevated baseline plasma levels of soluble PD-L1 was also observed in blood samples from patients responding to anti-PD-L1 antibody treatment in the ongoing Phase 1 study.

Blood was collected into Sodium Heparin collection tubes. Tube was mixed thoroughly by slowly inverting the collection tube. Subsequently, collection tubes were centrifuged in a refrigerated centrifuge at a minimum of 1500-2000×g for 15 minutes. Plasma was transferred to polypropylene cryovials and kept frozen until analysis. Plasma was analyzed for IL-6 and other cytokines using modified ELISA according to manufacturer recommendations.

Figure 28:
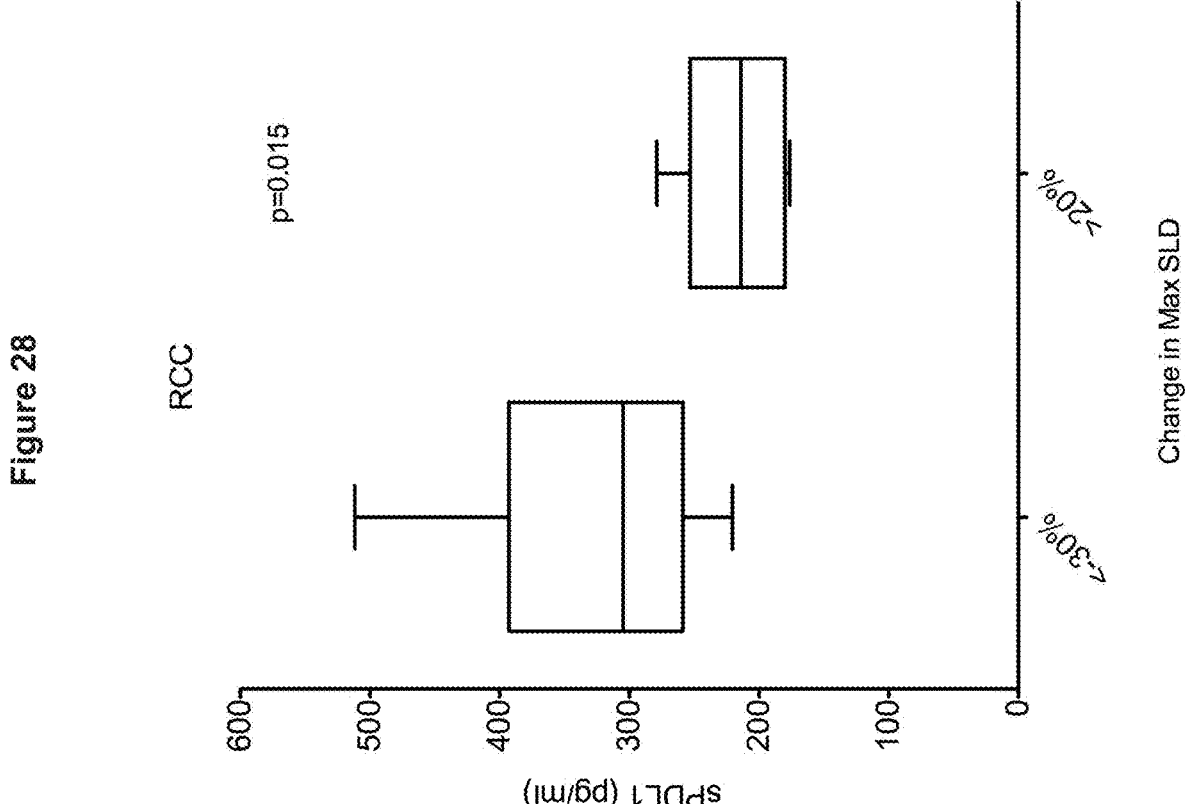
FIG. 28 shows the correlation of soluble PD-L1 in the blood of patients responding to treatment with anti-PD-L1 antibody.

As illustrated in FIG. 28, patients with RCC that responded to anti-PD-L1 antibody treatment with a >=30% reduction in the sum of the longest diameter of the target lesions (SLD) was found to correlate with a higher level of soluble PD-L1 (sPDL1) in their plasma samples than patients that only displayed a >=20% reduction in the SLD.

This preliminary data suggests that soluble PD-L1 expression in the plasma may be a valuable and useful biomarker for predicting responsiveness of a patient to cancer therapy which involves inhibition of the PD-L1/PD-1 pathway.

Figure 30:
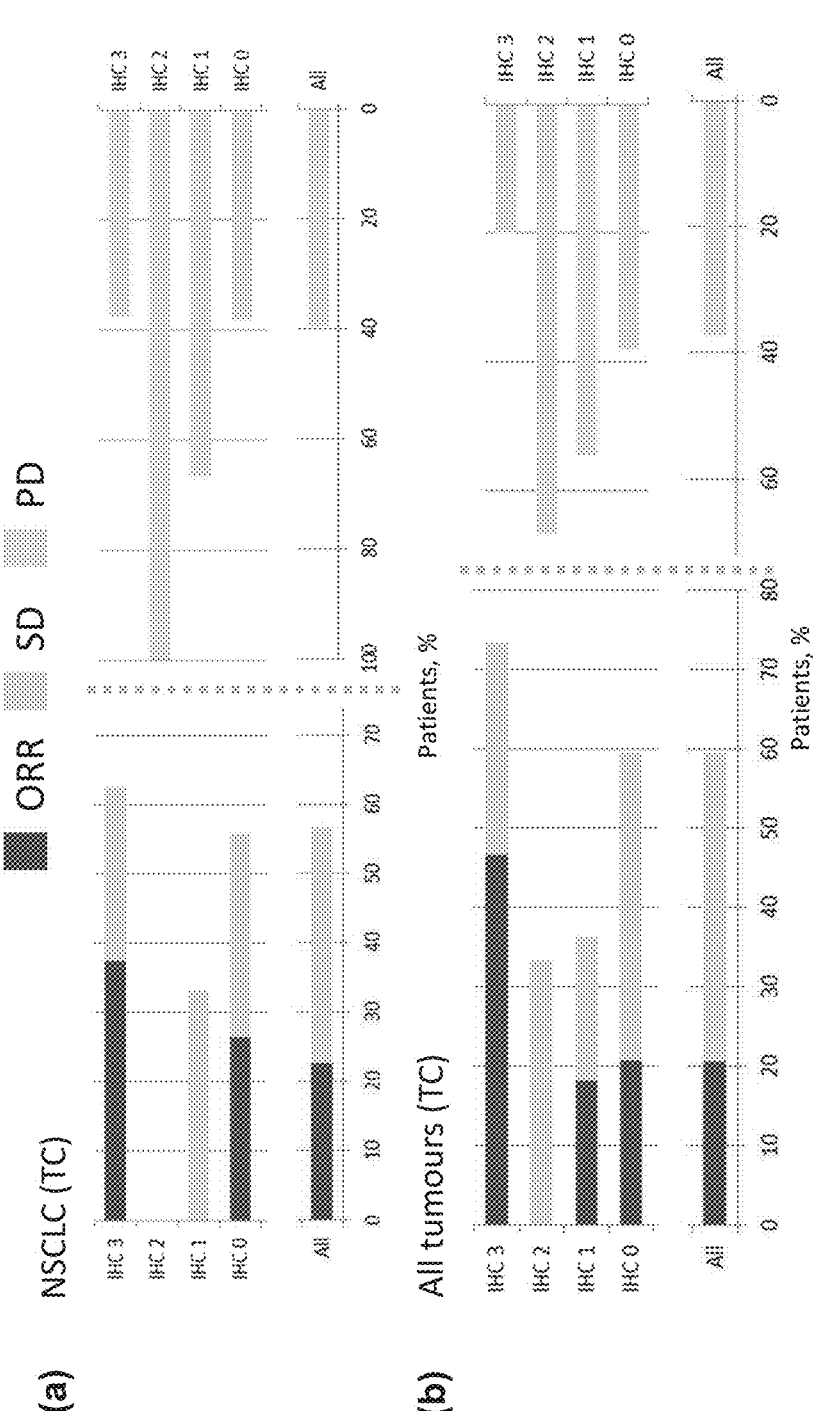
FIG. 30 shows the association between of PD-L1 expression in tumor cells and response to anti-PD-L1 treatment. (a) in NSCLC, (b) in all tumors.

Example 20—Association of PD-L1 Expression on Tumor Infiltrating Immune Cells and Tumor Cell with Response to Anti-PD-L1 Treatment In the ongoing Phase 1 study, a clear association of response to anti-PD-L1 treatment with PD-L1 expression in both tumor infiltrating immune cells (IC) and tumor cells was observed. As illustrated in FIG. 29, the association between PD-L1 expression in tumor infiltrating immune cells (IC) and response to anti-PD-L1 treatment was observed in patients with NSCLC (FIG. 29(a)) as well as in all patients (FIG. 29(b)). Similarly, the association between PD-L1 expression in tumor cells (TC) and response to anti-PD-L1 treatment was observed in patients with NSCLC (FIG. 30(a)) as well as in all patients (FIG. 30(b)).

Although the foregoing invention has been described in some detail by way of illustration and example for purposes of clarity of understanding, the descriptions and examples should not be construed as limiting the scope. The disclosures of all patent and scientific literature cited herein are expressly incorporated in their entirety by reference.

---

What is claimed is:

1. A method for treating a non-small cell lung cancer (NSCLC) in an individual who is likely to have an increased clinical benefit from treatment with an anti-PD-L1 antibody, the method comprising administering an effective amount of an anti-PD-L1 antibody to the individual, wherein the tumor tissue sample from the individual is obtained prior to treatment with the anti-PD-L1 antibody, wherein the anti-PD-L1 antibody comprises the following hypervariable regions (HVRs):

```
    (i) an HVR-H1 sequence of
                        (SEQ ID NO: 15)
    GFTFSDSWIH;

(ii) an HVR-H2 sequence of
                        (SEQ ID NO: 16)
    AWISPYGGSTYYADSVKG;

(iii) an HVR-H3 sequence of
                        (SEQ ID NO: 3)
    RHWPGGFDY;

(iv) an HVR-L1 sequence of
                        (SEQ ID NO: 17)
    RASQDVSTAVA;

(v) an HVR-L2 sequence of
                        (SEQ ID NO: 18)
    SASFLYS;
    and (vi) an HVR-L3 sequence of
                        (SEQ ID NO: 19)
    QQYLYHPAT.
``` and
  wherein the individual has been determined as likely to have an increased clinical benefit from treatment with the anti-PD-L1 antibody based on a detectable expression level of PD-L1 protein in tumor-infiltrating immune cells covering ≥10% of tumor area in the tumor tissue sample, and wherein the tumor-infiltrating immune cells include T lymphocytes.

2. The method of claim 1, wherein the anti-PD-L1 antibody comprises a heavy chain variable region (VH) having the amino acid sequence of SEQ ID NO: 20 and a light chain variable region (VL) having the amino acid sequence of SEQ ID NO: 21.

3. The method of claim 1, wherein the tumor tissue sample:
  (a) further comprises tumor cells, stromal cells, or a combination thereof; and/or
  (b) is formalin-fixed and paraffin-embedded, archival, or fresh.

4. The method of claim 1, wherein the increased clinical benefit comprises a relative increase in one or more of the following: objective response rate (ORR), overall survival (OS), progression free survival (PFS), complete response (CR), partial response (PR), or a combination thereof.

5. The method of claim 1, wherein PD-L1 protein has been detected in the tumor tissue sample using immunohistochemistry (IHC).

6. The method of claim 5, wherein PD-L1 protein has been detected:
  (a) using an anti-PD-L1 diagnostic antibody; and/or
  (b) as a weak staining intensity by IHC, as a moderate staining intensity by IHC, or as a strong staining intensity by IHC.

7. The method of claim 6, wherein staining is membrane staining, cytoplasmic staining, or a combination thereof.

8. The method of claim 1, wherein the presence or level of:
  (a) PD-1, PD-L2, or both PD-1 and PD-L2;
  (b) one or more T cell related markers, wherein the one or more T cell related markers is CD8A, IFN-g, EOMES, Granzyme-A, Granzyme-B, CXCL9, or a combination thereof; and/or (c) CX3CL1, CD45RO, IDO1, Galectin 9, MIC-A, MIC-B, CTLA-4, or a combination thereof, has been detected in the tumor tissue sample obtained from the individual.

9. The method of claim 8, wherein:

(a) PD-1, PD-L2, or a combination thereof has been detected in the tumor tissue sample using quantitative polymerase chain reaction (qPCR), reverse transcription qPCR (RT-qPCR), multiplex qPCR or RT-qPCR, or a combination thereof;

(b) the one or more T cell related markers have been detected in the tumor tissue sample using qPCR, RT-qPCR, multiplex qPCR, RT-qPCR, RNA-seq, or a combination thereof; and/or (c) CX3CL1, CD45RO, IDO1, Galectin 9, MIC-A, MIC-B, CTLA-4, or a combination thereof has been detected in the tumor tissue sample using qPCR, RT-qPCR, multiplex qPCR, RT-qPCR, RNA-seq, or a combination thereof.

10. The method of claim 9, wherein an increased level of the one or more T-cell related markers in the tumor tissue sample compared to the level of the one or more T-cell related markers in a reference sample indicates that the individual is likely to have an increased clinical benefit from treatment with the anti-PD-L1 antibody.

11. The method of claim 10, wherein the reference sample is a tissue sample, a plasma sample, or a serum sample from (i) one or more healthy individuals who is not the individual undergoing treatment; or (ii) the individual undergoing treatment.

12. The method of claim 1, wherein the anti-PD-L1 antibody is atezolizumab (MPDL3280A).

13. The method of claim 1, further comprising administering an effective amount of a second therapeutic agent to the individual, wherein the second therapeutic agent is a cytotoxic agent, a chemotherapeutic agent, a growth inhibitory agent, a radiation therapy agent, anti-angiogenic agent, or a combination thereof.

14. A method for treating an NSCLC in an individual who is likely to have an increased clinical benefit from treatment with an anti-PD-L1 antibody, the method comprising administering an effective amount of an anti-PD-L1 antibody to the individual, wherein the tumor tissue sample from the individual is obtained prior to treatment with the anti-PD-L1 antibody, wherein the anti-PD-L1 antibody is atezolizumab (MPDL3280A), wherein the increased clinical benefit comprises a relative increase in ORR, wherein the individual has been determined as likely to have an increased clinical benefit from treatment with the anti-PD-L1 antibody based on a detectable expression level of PD-L1 protein in tumor-infiltrating immune cells covering ≥10% of tumor area in the tumor tissue sample, wherein the tumor-infiltrating immune cells include T lymphocytes, and wherein the PD-L1 protein has been detected using IHC.

15. The method of claim 14, wherein the IHC has been performed using the Ventana Benchmark XT or Benchmark Ultra system.

* * * * *

```
                       SEQUENCE LISTING

<160> NUMBER OF SEQ ID NOS: 21

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Asp or Gly

<400> SEQUENCE: 1

Gly Phe Thr Phe Ser Xaa Ser Trp Ile His
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Leu
<220> FEATURE:
<221> NAME/KEY: MOD_RES
<222> LOCATION: (10)..(10)
<223> OTHER INFORMATION: Thr or Ser

<400> SEQUENCE: 2

Ala Trp Ile Xaa Pro Tyr Gly Gly Ser Xaa Tyr Tyr Ala Asp Ser Val
1               5                   10                  15

Lys Gly

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg His Trp Pro Gly Gly Phe Asp Tyr
1               5

<210> SEQ ID NO 4
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Val Arg Gln Ala Pro Gly Lys Gly Leu Glu Trp Val
1               5                   10

<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Gly Gln Gly Thr Leu Val Thr Val Ser Ala
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asp or Val
<220> FEATURE:
<221> NAME/KEY: MOD_RES
<222> LOCATION: (6)..(6)
<223> OTHER INFORMATION: Val or Ile
<220> FEATURE:
<221> NAME/KEY: MOD_RES
<222> LOCATION: (7)..(7)
<223> OTHER INFORMATION: Ser or Asn
<220> FEATURE:
<221> NAME/KEY: MOD_RES
```

-continued

```
<222> LOCATION: (9)..(9)
<223> OTHER INFORMATION: Ala or Phe
<220> FEATURE:
<221> NAME/KEY: MOD_RES
<222> LOCATION: (10)..(10)
<223> OTHER INFORMATION: Val or Leu

<400> SEQUENCE: 8

Arg Ala Ser Gln Xaa Xaa Xaa Thr Xaa Xaa Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phe or Thr
<220> FEATURE:
<221> NAME/KEY: MOD_RES
<222> LOCATION: (6)..(6)
<223> OTHER INFORMATION: Tyr or Ala

<400> SEQUENCE: 9

Ser Ala Ser Xaa Leu Xaa Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Gly, Phe or Ser
<220> FEATURE:
<221> NAME/KEY: MOD_RES
<222> LOCATION: (4)..(4)
<223> OTHER INFORMATION: Leu, Tyr, Phe or Trp
<220> FEATURE:
<221> NAME/KEY: MOD_RES
<222> LOCATION: (5)..(5)
<223> OTHER INFORMATION: Tyr, Asn, Ala, Thr, Gly, Phe or Ile
<220> FEATURE:
<221> NAME/KEY: MOD_RES
<222> LOCATION: (6)..(6)
<223> OTHER INFORMATION: His, Val, Pro, Thr or Ile
<220> FEATURE:
<221> NAME/KEY: MOD_RES
<222> LOCATION: (8)..(8)
<223> OTHER INFORMATION: Ala, Trp, Arg, Pro or Thr

<400> SEQUENCE: 10

Gln Gln Xaa Xaa Xaa Xaa Pro Xaa Thr
1               5

<210> SEQ ID NO 11
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

-continued

```
Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Tyr Gln Gln Lys Pro Gly Lys Ala Pro Lys Leu Leu Ile Tyr
1               5                   10                  15

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Gly Gln Gly Thr Lys Val Glu Ile Lys Arg
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Phe Thr Phe Ser Asp Ser Trp Ile His
1               5                   10

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Trp Ile Ser Pro Tyr Gly Gly Ser Thr Tyr Tyr Ala Asp Ser Val
1               5                   10                  15
```

-continued

```
Lys Gly

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ala Ser Gln Asp Val Ser Thr Ala Val Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Ala Ser Phe Leu Tyr Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Gln Tyr Leu Tyr His Pro Ala Thr
1               5

<210> SEQ ID NO 20
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115
```

-continued

```
<210> SEQ ID NO 21
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
                100                 105
```